US009410898B2

(12) United States Patent
Ikushima

(10) Patent No.: US 9,410,898 B2
(45) Date of Patent: Aug. 9, 2016

(54) APPEARANCE INSPECTION DEVICE, APPEARANCE INSPECTION METHOD, AND PROGRAM

(71) Applicant: Keyence Corporation, Osaka (JP)

(72) Inventor: Yasuhisa Ikushima, Osaka (JP)

(73) Assignee: Keyence Corporation, Osaka (JP)

( * ) Notice: Subject to any disclaimer, the term of this patent is extended or adjusted under 35 U.S.C. 154(b) by 272 days.

(21) Appl. No.: 13/971,867

(22) Filed: Aug. 21, 2013

(65) Prior Publication Data

US 2014/0078498 A1 Mar. 20, 2014

(30) Foreign Application Priority Data

Sep. 14, 2012 (JP) ................................ 2012-202271

(51) Int. Cl.

*G01N 21/88* (2006.01)
*G06K 9/03* (2006.01)
*G06T 7/00* (2006.01)

(52) U.S. Cl.

CPC ................ *G01N 21/88* (2013.01); *G06K 9/033* (2013.01); *G06T 7/001* (2013.01); *G06K 2209/19* (2013.01); *G06T 2207/20092* (2013.01); *G06T 2207/30148* (2013.01)

(58) Field of Classification Search

None
See application file for complete search history.

(56) References Cited

U.S. PATENT DOCUMENTS 6,816,609 B1 * 11/2004 Shimizu ............... G01B 11/024 348/86
8,155,770 B2 * 4/2012 Barlovic .......... G05B 19/41865 483/21
8,988,521 B2 * 3/2015 Yoon ......................... G06T 7/60 348/80
2003/0095710 A1 * 5/2003 Tessadro ....................... 382/199
2003/0101013 A1 * 5/2003 Solecky .................. G06T 7/001 702/85
2006/0023937 A1 * 2/2006 Tessadro .............. G06K 9/4604 382/152
2006/0093205 A1 * 5/2006 Bryll et al. .................... 382/152
2011/0274362 A1 * 11/2011 Isomae et al. ................. 382/224
2012/0081546 A1 * 4/2012 Matsumoto .......... G02B 21/367 348/142
2012/0106824 A1 * 5/2012 Archie .................. G06T 7/0006 382/141
2013/0108147 A1 * 5/2013 Harada ................... H01L 22/12 382/149
2015/0009319 A1 * 1/2015 Toyoda ................... H01L 22/12 348/126
2015/0139531 A1 * 5/2015 Hirai ....................... H01L 22/12 382/149

FOREIGN PATENT DOCUMENTS

| | | |
|---|---|---|
| JP | 06-167321 | 6/1994 |
| JP | 09-251536 | 9/1997 |
| JP | 2000-227316 | 8/2000 |
| JP | 2000-234915 | 8/2000 |
| JP | 2000-241117 | 9/2000 |
| JP | 2003-108996 | 4/2003 |

* cited by examiner

*Primary Examiner* — Stephen R Koziol
*Assistant Examiner* — Pinalben Patel
(74) *Attorney, Agent, or Firm* — Kilyk & Bowersox, P.L.L.C.

(57) ABSTRACT

A burden on a user is reduced by referring to a measurement region set for a certain measurement tool among a plurality of measurement tools to be used by an appearance inspection device as a measurement region of another measurement tool. A reference point or a search region serving as a reference of measurement for a first measurement tool such as a connector dimension inspection tool is set for a basic image acquired by imaging a non-defective product. Next, a second measurement tool such as an area measurement tool that performs measurement separate from the first measurement tool is selected by the user. For coordinate data of a measurement region, which is a region to be measured by the second measurement tool, coordinate data of the reference point or the search region set for the first measurement tool is adjusted if necessary and referred to.

14 Claims, 62 Drawing Sheets

APPEARANCE INSPECTION DEVICE, APPEARANCE INSPECTION METHOD, AND PROGRAM

CROSS-REFERENCE TO RELATED APPLICATIONS

The present application claims foreign priority based on Japanese Patent Application No. 2012-202271, filed Sep. 14, 2012, the contents of which is incorporated herein by reference.

BACKGROUND OF THE INVENTION

1. Field of the Invention

The present invention relates to an appearance inspection device, an appearance inspection method, and a program for inspecting an appearance of a product by imaging the product.

2. Description of Related Art

A so-called product appearance inspection is performed by imaging an appearance of a product such as a connector or a semiconductor element and performing pattern matching (image recognition). The product may not be within an imaging range of a camera depending on a size of the product, and an image representing the entire product is created by connecting a plurality of images for such a product to perform an appearance inspection (Japanese Unexamined Patent Publication Nos. H06-167321 and H09-251536).

In order to determine quality of a product (inspection object) serving as an object of the appearance inspection, it is necessary to preset an end portion or a corner portion of a terminal of the inspection object as a reference point, or set a straight line connecting a plurality of terminals as a reference line. Further, a parameter for measurement or a quality determination for each of 100 pins in a connector having the 100 pins should be set. Consequently, a user's workload is also increased in proportion to the number of pins.

A plurality of different types of measurement tools, which measure a position of a pin, measure a height of the pin, or measure a distance or area between pins, are included in a measurement tool for performing the appearance inspection. In the related art, the setting work tends to increase in proportion to the number of measurement tools because a detection point or an inspection region and a search region are set for each measurement tool.

On the other hand, a plurality of pins arranged in a connector are usually arranged at equal intervals in the same shape. It is necessary for the user to set a measurement region by displaying an individual connector pin on a monitor in conjunction with a position of each connector pin, or set a measurement region in conjunction with a position of one connector pin, move the region at a specific interval, and copy the region. In the former case, complex repetitive work occurs and a burden on the user is heavy. In the latter case, work of manually correcting a measurement region copied at an equal interval occurs since an interval between connector pins is not fixed when there is variation in positions of the connector pins. Such work occurs for each measurement tool.

On the other hand, if a measurement region for a connector-pin position measurement tool among a plurality of measurement tools can be set in any one method described above and setting results of the position measurement tool can be referred to for another measurement tool, the user's workload will generally be reduced in the plurality of measurement tools. For example, if a measurement region of each pin is set for a pin detection tool that detects a tip end position of a pin and a measurement region of each pin set for the pin detection tool is subjected to offset layout for an area measurement tool which measures an area between pins, the measurement region of the area measurement tool will be set through a simple task.

SUMMARY OF THE INVENTION

Accordingly, an object of the present invention is to provide a device and method which reduce a burden on a user by referring to a measurement region set for a certain measurement tool among a plurality of measurement tools to be used by an appearance inspection device as a measurement region of another measurement tool.

According to the present invention, there is provided an appearance inspection device including:

a basic image storage section which stores a basic image obtained by imaging an inspection object having a plurality of characteristic portions arrayed in a specific (or fixed) direction;

a display section which displays the basic image;

a position detection region setting section which sets, to the basic image displayed on the display section, a position detection region for detecting positions of the plurality of characteristic portions of the inspection object according to each of the characteristic portions;

a measurement tool selection section which selects, from a plurality of measurement tools for performing different measurement, a measurement tool to measure the inspection object;

a measurement region setting section which sets a measurement region, which is a region to be measured by the measurement tool selected by the measurement tool selection section, based on the position detection region set by the position detection region setting section; and a quality determination section which performs measurement according to the measurement region set by the measurement region setting section and determines whether the inspection object is good or defective based on a measurement result, wherein the display section displays the measurement region set by the measurement region setting section along with the basic image.

According to the present invention, a burden on a user can be reduced by referring to a measurement region set for a certain measurement tool among a plurality of measurement tools to be used by an appearance inspection device as a measurement region of another measurement tool.

DETAILED DESCRIPTION OF PREFERRED EMBODIMENTS

Embodiments of the present invention will be described below. Each embodiment described below will help understanding of various concepts such as the generic concept, intermediate concept, and subordinate concept of the present invention. Also, the technical scope of the present invention is settled by the scope of the claims, and is not limited to each embodiment described below.

Figure 1:
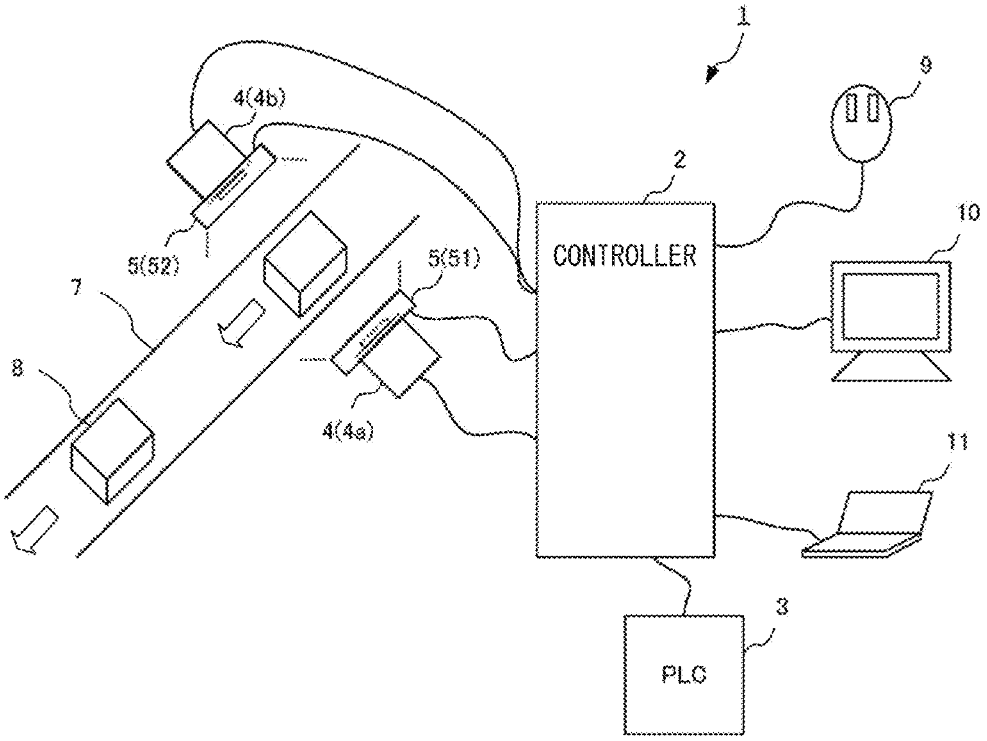
FIG. 1 is a schematic diagram illustrating an outline of an appearance inspection device.

FIG. 1 is a schematic diagram illustrating an outline of an appearance inspection device 1. The appearance inspection device 1 includes a controller 2, a programmable logic controller (PLC) 3, cameras 4, illuminating devices 5 (a front light 51 and a back light 52), a mouse 9, a monitor 10, and a program creation support device 11. An inspection object 8 is conveyed by a conveyor device 7 such as a belt conveyor to be controlled by the PLC 3, and the inspection object 8 illuminated by the illuminating device such as the front light 51 or the back light 52 is imaged by the camera 4. According to a command from the PLC 3, the controller 2 switches the illuminating device for illuminating the inspection object 8 or causes the camera 4 to perform imaging, for example. As the cameras 4, a front camera 4*a* is installed on the left side in a conveying direction of the inspection object 8 and a back camera 4*b* is installed on the right side. The back camera 4*b* is used when the right side in the conveying direction of the inspection object 8 is inspected. Hereinafter, unless particularly described, the front camera 4*a* will be described as the camera 4. Here, although two cameras are used as an example, the number of cameras may be 3, 4, or more. Of course, one camera may be used. The number of cameras is determined according to a type of inspection object or appearance inspection. For example, two cameras are used to observe a floating pin from a ground surface (coplanarity) of a plurality of pins installed on both sides of the connector because it is necessary to image pins from both sides of the connector. Further, a third camera is necessary to image an upper surface of the connector.

The controller 2 executes various types of measurement processing such as edge detection or area calculation from the image of the inspection object (workpiece) 8. Image processing is performed using image data obtained from the camera 4 and a determination signal is output as a signal indicating a determination result of quality or the like of the inspection object 8 to a control device such as the externally connected PLC 3.

The camera 4 includes a camera module having an image sensor which images the inspection object 8. As the image sensor, for example, a complementary metal-oxide-semiconductor (CMOS) or a charge coupled device (CCD) can be used. The inspection object 8 is imaged based on a control signal input from the PLC 3, for example, an imaging trigger signal defining a timing at which image data is received from the camera 4.

The monitor 10 is a display device such as a liquid crystal panel or a self-light-emitting panel. An image obtained by imaging the inspection object 8 or a result of measurement processing using image data thereof is displayed. The monitor 10 may display an image acquired from a non-defective product such as a reference image to be used to create comparative data (a model image) for pattern matching.

The mouse 9 is an input device for allowing the user to perform various operations on the monitor 10 (this can be omitted if the monitor 10 is a touch panel). The mouse 9 selects each menu item or set a parameter value on the monitor 10. The mouse 9 is an example of a pointing device. By viewing the monitor 10, the user can check an operation state while the controller 2 is in operation. In addition, the user can perform various settings or various edits if necessary by operating the mouse 9 while viewing the monitor 10.

The illuminating device 5 is a device which illuminates the inspection object 8. In FIG. 1, the front light 51 and the back light 52 are illustrated. In addition, as the illuminating device 5, there may be adopted illuminating devices which perform various illuminations such as coaxial epi-illumination for highlighting gloss, low-angle illumination for highlighting a scratch or dent edge, black-light illumination for radiating black light, surface illumination to be used as the back light 52 (transillumination for providing illumination from a side opposite to the front light 51 and observing transmitted light or shadow of the inspection object), dome illumination for radiating diffused light in all directions, and the like. In particular, the coaxial epi-illumination is an illumination technique of substantially uniformly illuminating an overall field of view, and has an advantage in that substantially the same effect as that of an illumination technique of receiving regular reflection light from the inspection object 8 is obtained by arranging the camera 4 and the illuminating device 5 in a V-shape. In addition, the low-angle illumination is an illumination technique of arranging floodlight elements such as light emitting diodes (LEDs), for example, in a ring shape and radiating light to the surface of the inspection object 8 in all circumference directions at a shallow angle. The light radiated to the surface of the inspection object 8 is not reflected in a direction of the camera 4, and only light reflected by an edge portion of a dent or scratch is received. That is, because an irradiation angle is a very shallow angle, reflection is weak in a gloss surface, strong reflection can be obtained only in a slight scratch or edge on the inspection object 8, and clear contrast can be obtained. In other words, the front light 51 is illumination light for extracting a characteristic (a texture, an edge, or the like) of a surface of the inspection object 8, and the back light 52 is illumination light for extracting a contour (or an edge portion) of the inspection object 8.

The program creation support device 11 is a computer (personal computer (PC)) for creating a control program to be executed by the controller 2. The control program has a plurality of measurement processing modules, each of which performs different measurement related to an appearance inspection as will be described below. The controller 2 calls and executes various measurement processing modules in the set order. The program creation support device 11 and the controller 2 are connected via a communication network. A control program or setting information such as parameter values generated on the program creation support device 11 is transmitted to the controller 2. In addition, on the other hand, a control program or setting information such as parameter values can be received from the controller 2 and edited on the program creation support device 11.

In a factory, a plurality of inspection objects 8 flow on a line of the conveyor device 7 such as a conveyor. The camera 4 installed above (or beside or below) the inspection object 8 images the inspection object 8, and the controller 2 compares the captured image to a reference image (for example, an image obtained by imaging a non-defective product) or a model image created from the reference image, and determines whether there is a scratch or defect in the inspection object 8. When a scratch, a defect, or the like is determined to be present in the inspection object 8, an NG determination is made. On the other hand, when no scratch, defect, or the like is determined to be present in the inspection object 8, an OK determination is made. Thus, the appearance inspection device 1 performs a quality determination of the appearance of the inspection object 8 using an image obtained by imaging the inspection object 8.

When the appearance of the inspection object 8 is inspected, it is necessary to set contents (parameter values and the like) of various parameters to be used in the inspection. For example, the parameters include an imaging parameter defining an imaging condition such as a shutter speed, an illumination parameter defining an illumination condition such as an intensity of illumination, a measurement processing parameter (so-called inspection parameter) defining an inspection condition indicating a type of inspection to be performed, and the like. In the appearance inspection device 1, contents of various parameters are set before a quality determination is made.

The appearance inspection device 1 has a mode in which the appearance inspection of the inspection object 8 that continuously flows on the line of the conveyor device 7 is actually performed, that is, an operation mode (Run mode) in which a quality determination of the inspection object 8 is actually performed, and a setting mode (non-Run mode) in which contents of various parameters to be used in the inspection are set, and a mode switching device for performing switching between the modes. Before the quality determination is repeatedly performed for the plurality of inspection objects 8 that are flowing on the line of the conveyor device 7 in the operation mode, the user sets (adjusts) optimum parameter values for various parameters in the setting mode. Basically, default values are set for various parameters and it is not necessary to particularly adjust the parameter values when the default values are determined to be optimum as the parameter values. However, actually, there is a case in which it is difficult for the user to obtain a desired determination result in the default values due to a difference in a peripheral illumination environment, an attachment position of the camera 4, a posture deviation of the camera 4, and pint adjustment or the like. Accordingly, switching from the operation mode to the setting mode is performed on the monitor 10 of the controller 2 or the program creation support device 11 and contents of various parameters are configured to be edited in the setting mode.

<Hardware Configuration of Appearance Inspection Device 1>

Figure 2:
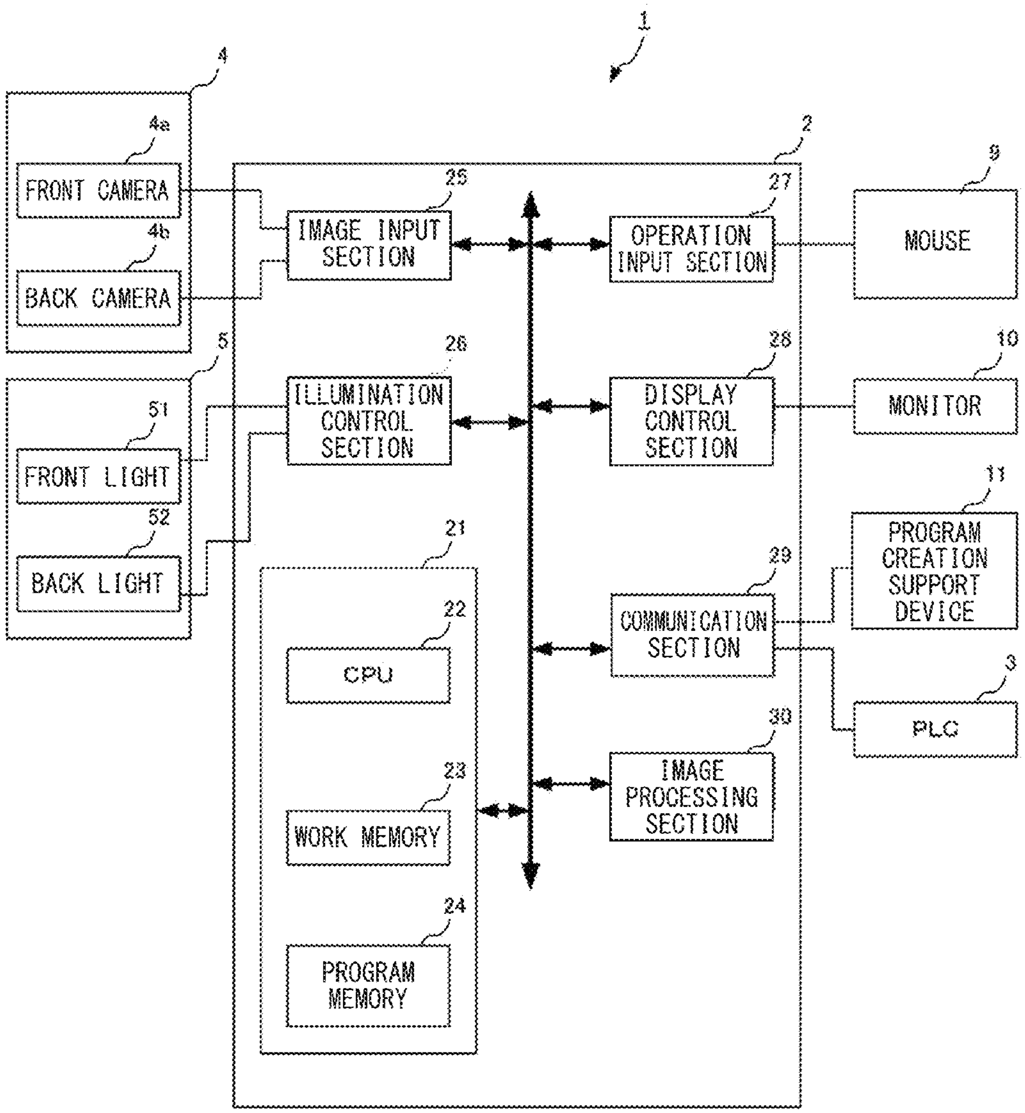
FIG. 2 is a diagram illustrating an example of a hardware configuration of the appearance inspection device.

FIG. 2 is a diagram illustrating an example of the hardware configuration of the appearance inspection device 1.

A main control section 21 performs numerical calculation or information processing based on various programs and controls the respective sections of hardware. For example, the main control section 21 has a central processing unit (CPU) 22 serving as an intermediate arithmetic processing device, a work memory 23 such as a random access memory (RAM) functioning as a work area when the main control section 21 executes various programs, and a program memory 24 such as a read only memory (ROM), a flash ROM, or an electronically erasable and programmable ROM (EEPROM) in which a start-up program, an initialization program, or the like is stored.

Based on a command from the CPU 22 of the main control section 21 or the PLC 3, an illumination control section 26 transmits an illumination control signal to the front light 51, the back light 52, or the like.

An image input section 25 includes an application specific integrated circuit (ASIC), which receives image data obtained by capturing an image in the camera 4, and the like. A frame buffer for buffering the image data may be included in the image input section 25. Specifically, the image input section 25 transmits an image data reception signal to the camera 4 upon receiving an imaging command of the camera 4 from the CPU 22. Accordingly, the image input section 25 receives image data obtained by capturing an image after imaging has been performed by the camera 4. The received image data is temporarily buffered (cached).

An operation input section 27 receives an operation signal input from the mouse 9. The operation input section 27 functions as an interface (I/F) that receives an operation signal from the mouse 9 based on the user's operation.

Operation contents of the user using the mouse 9 are displayed on the monitor 10. Specifically, by operating the mouse 9, the user can perform various operations when a control program of image processing is edited, when a parameter value of each measurement processing module is edited, when an imaging condition of the camera 4 is set, when a characteristic portion in a reference image is registered as a model image, or when a region consistent with a model image is set as an inspection region by performing a search within a search region on the monitor 10.

A display control section 28 includes a display digital signal processor (DSP) which causes the monitor 10 to display an image. A video memory such as a video RAM (VRAM) that temporarily stores image data when an image is displayed may be included in the display control section 28. Based on a display command transmitted from the CPU, a control signal for displaying a predetermined image (video) is transmitted to the monitor 10. For example, in order to display image data before or after measurement processing, a control signal is transmitted to the monitor 10. In addition, the display control section 28 also transmits a control signal for causing the monitor 10 to display operation contents of the user using the mouse 9.

A communication section 29 is connected to be communicable with the external PLC 3, the program creation support device 11, or the like. For example, the communication section 29 is installed on a manufacturing line for recognizing an arrival timing of the inspection object 8, and functions as an I/F which receives an imaging trigger signal from the PLC 3 when there is a trigger input from a sensor (photoelectric sensor or the like (not illustrated)) connected to the PLC 3. In addition, the communication section 29 functions as an I/F which receives a control program of the controller 2 transmitted from the program creation support device 11 or the like.

An image processing section 30 includes an arithmetic DSP or the like which executes measurement processing such as edge detection or area calculation. A memory that stores image data for measurement processing may be included in the image processing section 30. The image processing section 30 executes measurement processing on image data. Specifically, the image processing section 30 first performs internal transmission to the memory within the image processing section 30 by reading image data from a frame buffer of the image input section 25. Accordingly, the image processing section 30 performs measurement processing by reading image data stored in the memory.

The program memory 24 stores a control program for controlling each section of the illumination control section 26, the image input section 25, the operation input section 27, the display control section 28, the communication section 29, and the image processing section 30 according to a command of the CPU 22 or the like. In addition, the control program transmitted from the program creation support device 11 is stored in the program memory 24.

Upon receiving an imaging trigger signal from the PLC 3 via the communication section 29, the CPU 22 transmits an imaging command to the image input section 25. In addition, based on the control program, the CPU 22 transmits a command indicating image processing to be performed to the image processing section 30. A trigger input sensor such as a photoelectric sensor rather than the PLC 3 may be directly connected to the communication section 29 as a device which generates an imaging trigger signal.

Each piece of hardware thereof is connected to be communicable via an electrical communication path (wiring) such as a bus.

<Measurement Module (Image Processing Tool)>

Here, a measurement module that performs an appearance inspection is referred to as an image processing tool. There are various image processing tools. There are an edge position measurement tool, an edge angle measurement tool, an edge width measurement tool, an edge pitch measurement tool, an area measurement tool, a blob measurement tool, a pattern search measurement tool, a scratch measurement tool, and the like as major image processing tools.

Edge position measurement tool: A window for an inspection region from which an edge position is desired to be detected on a screen on which an image of the inspection object 8 is displayed is set and thus a plurality of edges (a position at which brightness switches to darkness or a position at which darkness switches to brightness) are detected by performing a scan operation in an arbitrary direction within a set inspection region. One edge is designated from a plurality of detected edges and a position of the designated edge is measured.

Edge angle measurement tool: Two segments are set within a set inspection region, and an inclined angle of the inspection object 8 from an edge detected by each segment is measured. For the inclined angle, a clockwise direction can be set to be positive, for example.

Edge width measurement tool: A plurality of edges are detected by performing a scan operation in an arbitrary direction within a set inspection region and widths between a plurality of detected edges are measured.

Edge pitch measurement tool: A plurality of edges are detected by performing a scan operation in an arbitrary direction within a set inspection region. A maximum value/minimum value or an average value of distances (angles) among the plurality of detected edges is measured.

Area measurement tool: An area of a white or black region is measured by performing binarization processing on an image of the inspection object 8 imaged by the camera 4. For example, a white or black region serving as a target to be measured is designated as a parameter and thus an area of the white or black region is measured.

Blob measurement tool: A number, an area, a center position, and the like are measured as parameters for a set (blob) of pixels having the same luminance value (255 or 0) by binarizing the image of the inspection object 8 imaged by the camera 4.

Pattern search measurement tool: A position, an inclined angle, and a correlation value of an image pattern are measured by pre-storing an image pattern (model image) to be compared in a storage device and detecting a portion similar to the stored image pattern from images of the imaged inspection object 8.

Scratch measurement tool: An average density value of pixel values is calculated by moving a small region (segment) within a set inspection region, and a scratch is determined to be present at a position having a density difference of a threshold value or more.

In addition, there are also an optical character recognition (OCR) tool that recognizes a character string by clipping character information within an inspection region and comparing the clipped character information to dictionary data or the like, a trend edge tool having a function of repeatedly performing detection of an edge at a position of each window while shifting a window (region) set on an image, a grayscale tool having a function of measuring an average, a deviation, and the like of grayscales within a set window, a density tool having a function of measuring an average, a deviation, and the like in density within the set window, and the like. The user can select a necessary image processing tool according to inspection contents. Note that these image processing tools only show representative examples of typical functions and methods of implementing the same. Image processing tools corresponding to all image processing can be a target of the present invention of this application.

<Basic Flow of Appearance Inspection>

Figure 3:
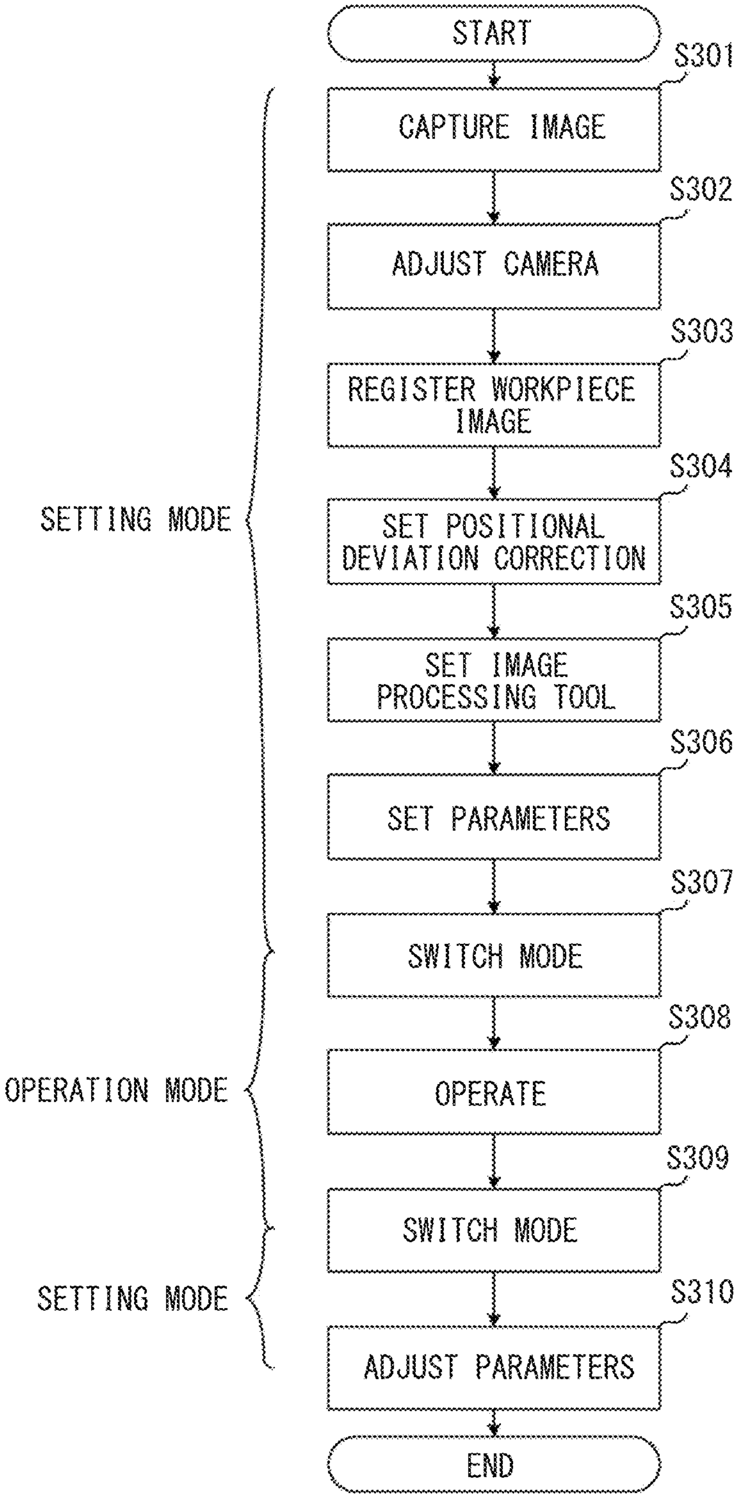
FIG. 3 is a flowchart illustrating a basic flow of appearance inspection processing.

FIG. 3 is a flowchart illustrating a basic flow of appearance inspection processing. The appearance inspection processing is divided into a setting mode in which a model image, an inspection region, a search region, a detection point (hereinafter referred to as a reference point), a reference line, and a threshold value of a tolerance or the like necessary to determine quality of the inspection object 8 are set and an operation mode in which quality is determined by actually imaging the inspection object 8 and performing pattern matching. It is general to repeatedly perform the setting mode and the operation mode in order to appropriately set an inspection parameter. Appearance inspection processing may be performed by dimension measurement, an area tool, a scratch tool, and the like.

In S301, the CPU 22 causes the camera 4 to perform imaging by transmitting an imaging command to the camera 4 through the image input section 25. The CPU 22 causes the monitor 10 to display image data acquired by the camera 4 through the display control section 28. The user checks a posture of the camera 4 and an illumination state of the illuminating device 5 by viewing an image displayed on the monitor 10.

In S302, the CPU 22 adjusts an exposure condition such as a shutter speed of the camera 4 based on an instruction input with the mouse 9. The user may manually adjust the posture of the camera 4.

In S303, the CPU 22 transmits an imaging command to the camera 4 so as to receive an image of the inspection object 8 arranged at an imaging position of the conveyor device 7 as a workpiece image. The workpiece image (basic image) may be a reference image to be stored in a non-volatile memory and repeatedly used or an image captured every time a model image is created in order to create the model image. Here, the workpiece image is stored in the work memory 23. The model image may be created from a reference image.

In S304, the CPU 22 executes positional deviation correction setting processing. In an image acquired by the camera 4, a position of the image of the inspection object 8 may be deviated from an ideal position. Accordingly, the CPU 22 corrects a positional deviation by rotating or shifting the image of the inspection object 8. The positional deviation correction may be performed by the image processing section 30.

In S305, the CPU 22 sets various image processing tools described above. For example, a type of measurement to be performed in the appearance inspection and a search region, an inspection region, a reference point, and the like necessary to execute measurement are set.

In S306, the CPU 22 sets a parameter (e.g., an inspection threshold value such as a tolerance) necessary in an appearance inspection based on an instruction input with the mouse 9. In S307, the CPU 22 performs switching from the setting mode to the operation mode.

In S308, the CPU 22 images the inspection object 8 using the camera 4 according to an instruction from the PLC 3, causes the image processing section 30 to execute pattern matching, determines quality based on an execution result, and outputs a determination result to the PLC 3 or the monitor 10.

In S309, the CPU 22 performs switching from the operation mode to the setting mode when a mode switching instruction is input from the mouse 9. In S310, the CPU 22 resets a parameter based on the instruction input with the mouse 9.

<Setting of Parameters>

Figure 4:
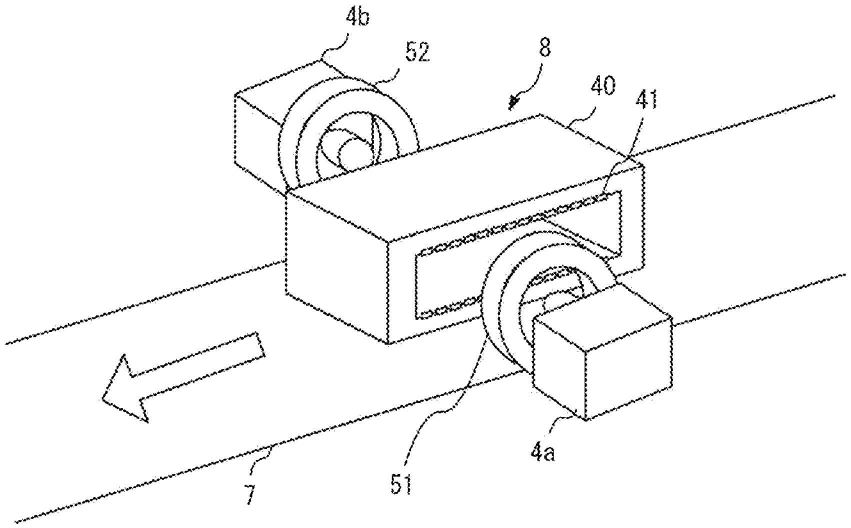
FIG. 4 is a diagram illustrating a positional relationship among an inspection object, a camera, and an illuminating device when parameters are set.

FIG. 4 illustrates a positional relationship among the inspection object 8, the camera 4, and the illuminating device 5 when the parameters are set. Although the inspection object 8 may be an integrated circuit (IC) having a plurality of pins, a ball grid array (BGA) having a plurality of solder balls, or the like, the inspection object 8 is assumed to be a connector having a housing 40 formed of a resin and a plurality of pins 41 for convenience of description.

The back light 52, which is the illuminating device 5, is arranged to face the camera 4 across the conveyor device 7, and illuminates the inspection object 8 from the rear side of the inspection object 8. The front light 51 is a ring illumination device and is arranged on the same side as the camera 4 when viewed from the conveyor device 7, and performs illumination from the front side of the inspection object 8.

In the operation mode, the PLC 3 controls the conveyor device 7 and when the inspection object 8 reaches an imaging position of the camera 4, stops the conveyor device 7 and commands the camera 4 to capture an image via the controller 2. In this case, the PLC 3 commands the illuminating device 5 to perform illumination via the controller 2. In addition, the camera 4 performs imaging in a state in which the front light 51 (for extracting a characteristic of the surface of the housing 40) illuminates a pin 41 or the housing 40 of the connector. The camera 4 performs imaging in a state in which the contour of the housing 40 of the connector is highlighted by the back light 52 (for extracting the contour of the housing 40).

On the other hand, in the setting mode, the conveyor device 7 is basically stopped, the controller 2 directly controls the camera 4 or the illuminating device 5, and a workpiece image of the inspection object 8 is captured. The inspection object 8 imaged in the setting mode is a workpiece (product) determined as a non-defective product by the user. In general, one workpiece image is acquired. However, the inspection object 8 may be long in a conveying direction of the conveyor device 7, and it may be difficult to image the entire inspection object 8 in a single imaging operation. In this case, the controller 2 controls the camera 4 to divide the inspection object 8 and image the inspection object 8 a plurality of times. When a plurality of workpiece images have been acquired in the setting mode, the number of images equal to that of the workpiece images are also acquired in the operation mode, and the workpiece images are compared with the model image.

In both the setting mode and the operation mode, the camera 4 performs imaging in a state in which the pin 41 or the housing 40 of the connector is illuminated by the front light 51. In addition, the camera 4 performs imaging in a state in which the contour of the housing 40 of the connector is highlighted by the back light 52. When the inspection object 8 is divided and imaged a plurality of times, the PLC 3 may perform a plurality of imaging operations by moving either the inspection object 8 or the camera 4. The inspection object 8 or the camera 4 may be manually moved. When the inspection object 8 is divided into three or more divisions and imaged, the camera 4 performs imaging by illuminating the inspection object 8 using the front light 51 at a first imaging position (the left end of the drawing) in the conveying direction and a final imaging position (the right end of the drawing) in the conveying direction. Thereafter, the camera 4 performs imaging by illuminating the inspection object 8 using the back light 52. On the other hand, the camera 4 performs imaging by illuminating the inspection object 8 using the front light 51 and an imaging operation using the back light 52 is omitted at one or more intermediate imaging positions between the first imaging position and the final imaging position. This is because the contour of the intermediate portion of the inspection object 8 is not important in the appearance inspection. It is possible to improve work efficiency of the appearance inspection by omitting the imaging operation using the back light 52 for the intermediate portion.

Figure 5:
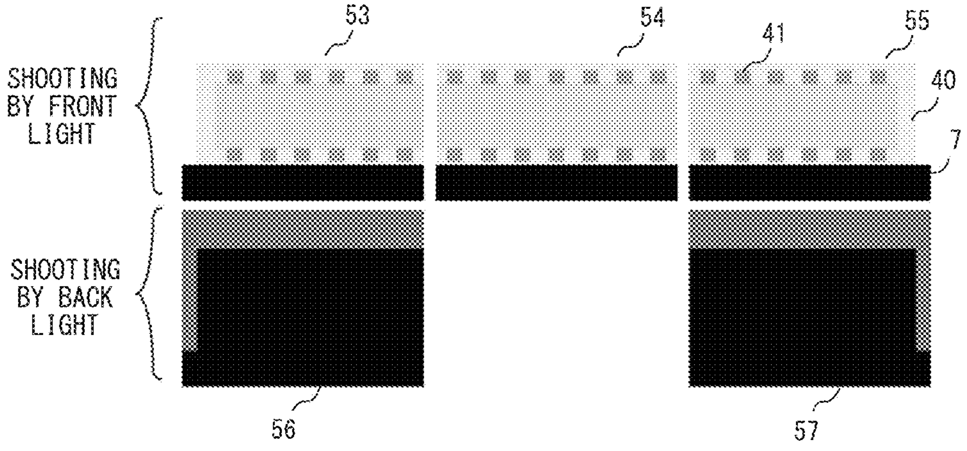
FIG. 5 is a diagram illustrating images captured by a front light and images captured by a back light after dividing a connector, which is the inspection object, into three divisions.

FIG. 5 illustrates images captured by the front light 51 and images captured by the back light 52 in a state in which a connector, which is the inspection object 8, is divided into three divisions. An image 53 is an image of a left end of the connector imaged by the front light 51. An image 54 is an intermediate image of the connector imaged by the front light 51. An image 55 is an image of a right end of the connector imaged by the front light 51. An image 56 is an image of a left end of the connector imaged by the back light 52. An image 57 is an image of a right end of the connector imaged by the back light 52. A black part under the connector in each image of the images 53 to 55 is an image of a belt conveyor that is the conveyor device 7. When the inspection object 8 is mounted on a jig or the like and conveyed by the conveyor device 7, the jig is imaged in the image. As described above, the imaging operation by the back light 52 is omitted in the center (hereinafter referred to as the middle) of the connector.

The camera 4 images the connector arranged at a predetermined position using the front light 51, and then images the connector using the back light 52 in a state in which the position of the connector has been maintained. That is, the position of the inspection object 8 is consistent in the image captured using the front light 51 and the image captured using the back light 52.

The same portion of the connector is shown at the right end of the image 53 and the left end of the image 54. Likewise, the same portion of the connector is shown at the right end of the image 54 and the left end of the image 55. The same portion is redundantly shown in the adjacent partial images because one full image is created by connecting three partial images. That is, the image processing section 30 connects two adjacent partial images so that the same pins commonly shown in the two adjacent partial images are superimposed. The entire connector is included in the full image created thereby.

<Dimension Measurement>

Distances Between Pin and Corner

Figure 6:
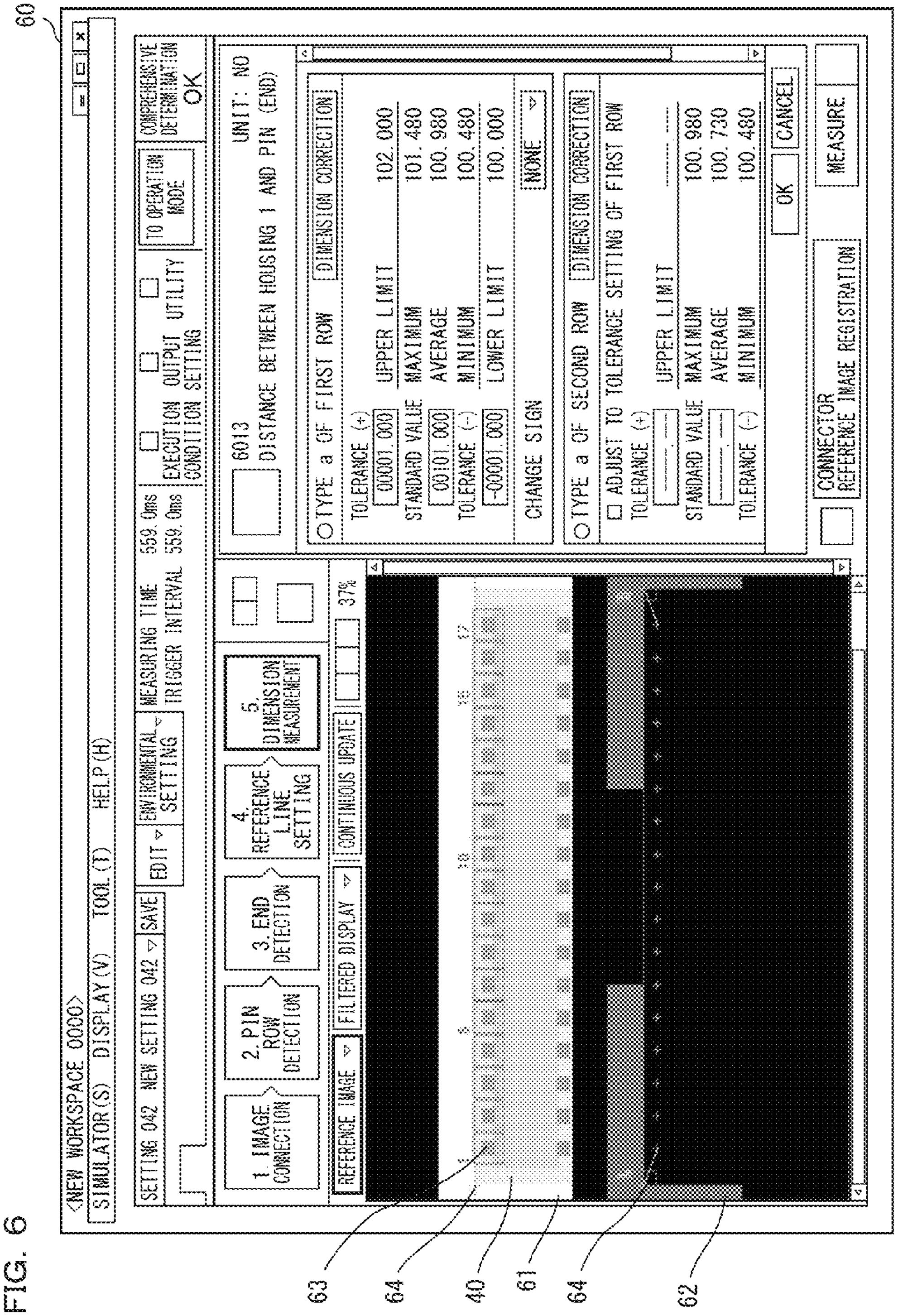
FIG. 6 is a diagram illustrating an example of dimension measurement.

FIG. 6 is a diagram illustrating an example of the dimension measurement. In a user interface (UI) 60 displayed on the monitor 10, one image (front-light image 61) configured by connecting a plurality of partial images captured using the front light 51 and an image (back-light image 62) configured by connecting a plurality of partial images captured using the back light 52 are shown. Each of the front-light image 61 and the back-light image 62 is the full image created by connecting partial images of the same subject imaged by performing switching between the front light 51 and the back light 52. Consequently, a coordinate system of the front-light image 61 is consistent with that of the back-light image 62. Here, the coordinate system of the front-light image 61 has the left end of the front-light image 61 as the origin, and the coordinate system of the back-light image 62 has the left end of the back-light image 62 as the origin. Consequently, the center position of each pin in the front-light image 61 and the center position of each pin in the back-light image 62 can be represented by the same coordinates. Likewise, a position of a corner 64 of the housing 40 in the front-light image 61 and a position of the corner 64 of the housing 40 in the back-light image 62 can be represented by the same coordinates.

In the UI 60, the front-light image 61 and the back-light image 62 are simultaneously displayed so that both ends in the horizontal direction of the front-light image 61 are consistent with both ends in the horizontal direction of the back-light image 62. That is, the front-light image 61 and the back-light image 62 are vertically arranged and displayed by aligning the ends in the horizontal direction of the front-light image 61 and the ends in the horizontal direction of the back-light image 62. Thereby, the user easily understands that both the front-light image 61 and the back-light image 62 are images acquired by imaging the same inspection object 8. In addition, a search region, an inspection region, and a detection point set in the front-light image 61 may be directly set in the back-light image 62. That is, in the front-light image 61 and the back-light image 62, the search region, the inspection region, and the detection point may be displayed in association with one another. Likewise, the search region, the inspection region, and the detection point set in the back-light image 62 may be directly set in the front-light image 61 and the two may be displayed in association with each other. Thereby, a characteristic portion that is difficult to set in one image can be set using the other image. In the present invention, it is possible to set various measurement targets such as dimensions in the inspection object 8 by utilizing such characteristics.

In FIG. 6, the image processing section 30 calculates a distance from the corner 64 of the housing 40 to the center of a 1st pin 63. In the connector of this example, 17 pins per row are arranged in two rows. In terms of a pin number, a pin of a left end is set as a 1st pin and a pin of a right end is set as a 17th pin.

Incidentally, when the color of the housing 40 is close to white, the position of the corner 64 is likely not to be accurately detected from the front-light image 61. On the other hand, it is possible to accurately detect the corner 64 in the back-light image 62. This is because the contrast between a background and the housing is high. The image processing section 30 determines a position (coordinates) of the 1st pin 63 from the front-light image 61, and determines a position of the corner 64 from the back-light image 62. Here, because the coordinate systems of the front-light image 61 and the back-light image 62 are completely consistent with each other, the image processing section 30 can calculate a distance between the two from the position of the 1st pin 63 obtained from the front-light image 61 and the position of the corner 64 obtained from the back-light image 62. It is possible to calculate a distance between the 17th pin and an upper-right corner of the housing 40 from the front-light image 61 and the back-light image 62 in a similar procedure.

Figure 7:
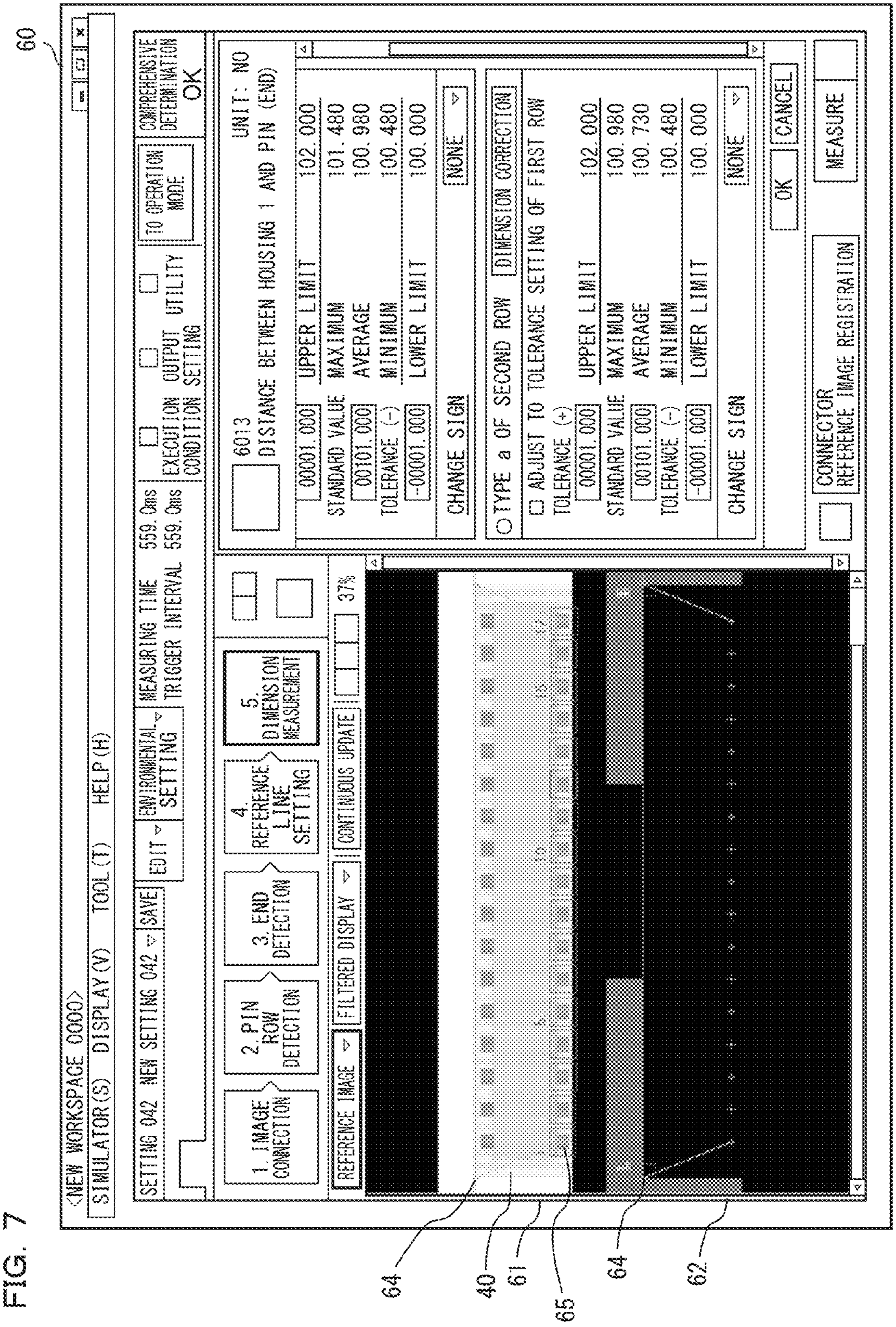
FIG. 7 is a diagram illustrating an example of dimension measurement related to pins of a second row.

FIG. 7 is a diagram illustrating an example of dimension measurement related to pins of a second row. In a procedure similar to that for the 1st pin 63 of the first row, a distance from a 1st pin 65 of the second row to the corner 64 can also be calculated.

Here, although the 1st pin and the 17th pin have been described, it is also possible to detect a position of a pin that is a characteristic point from the front-light image 61, detect a position of a corner that is a characteristic point from the back-light image 62, and obtain a distance between the two with respect to 2nd pin to 16th pin.

Distance (Pin Height) from Pin to Outer Edge of Housing

Figure 8:
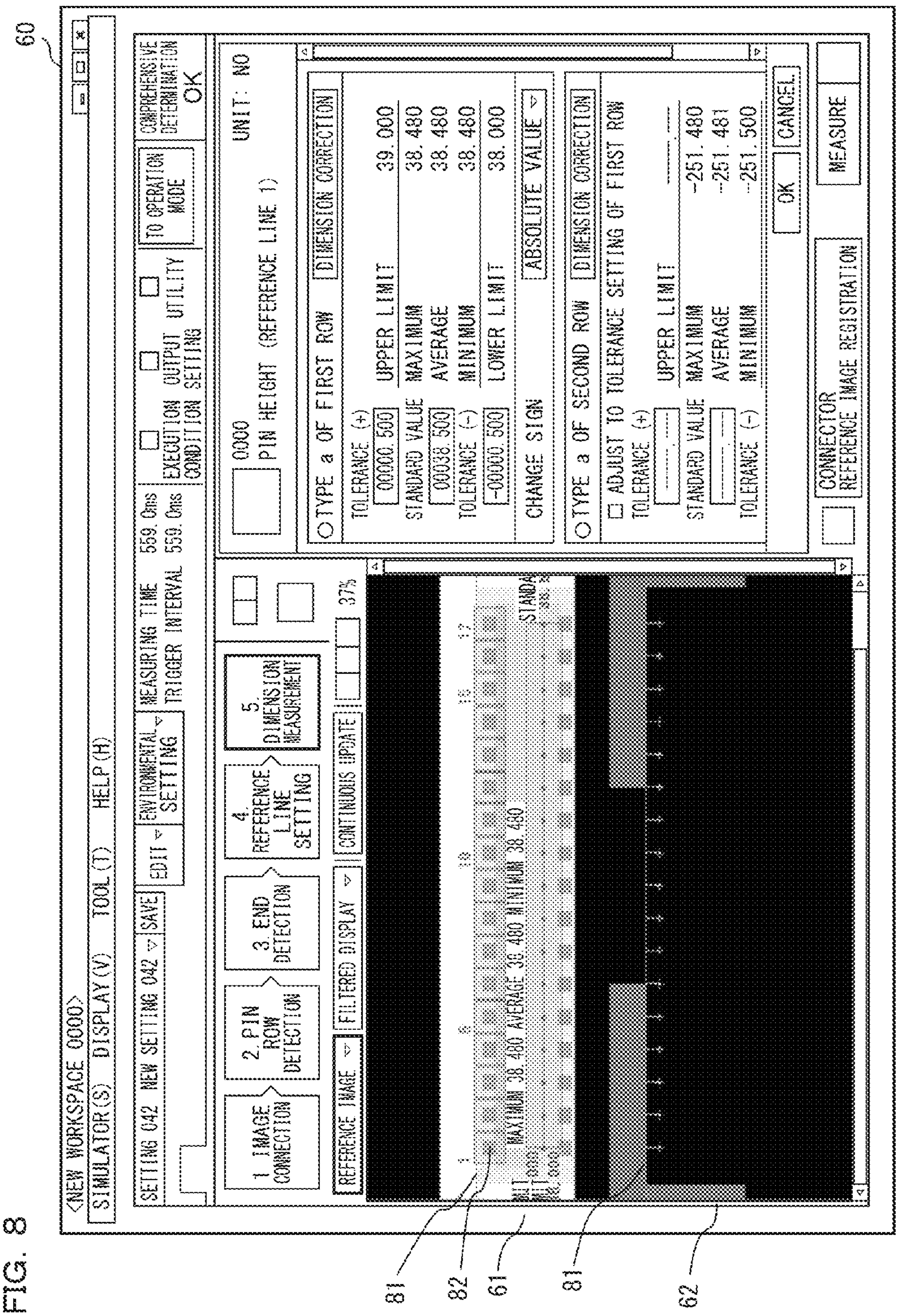
FIG. 8 is a diagram illustrating a method of obtaining a height of each pin.

FIG. 8 is a diagram illustrating a method of obtaining a height of each pin. In this example, the image processing section 30 calculates a distance from the center (reference point 82) of each pin to an outer edge on an upper side of the housing 40 as the pin height.

In order to establish the outer edge of the upper side of the housing 40 from the back-light image 62, the image processing section 30 detects a position of an upper-right corner and a position of an upper-left corner and determines a straight line (an equation of a straight line) connecting the two as a reference line 81. The back-light image 62 is used because the corner can be accurately detected as compared to the front-light image 61. The image processing section 30 detects the center position of each pin as the reference point 82 from the front-light image 61. The image processing section 30 calculates a distance from the reference point 82 of each pin to the reference line 81 as the height of each pin.

Here, the reference point 82 has been detected from the front-light image 61, and the reference line 81 has been detected from the back-light image 62. However, when parameters which affect the contrast of the image, such as a shape, coloration, and material of the inspection object 8, are different, the image processing section 30 may detect the reference line 81 from the front-light image 61 and detect the reference point 82 from the back-light image 62.

Figure 9:
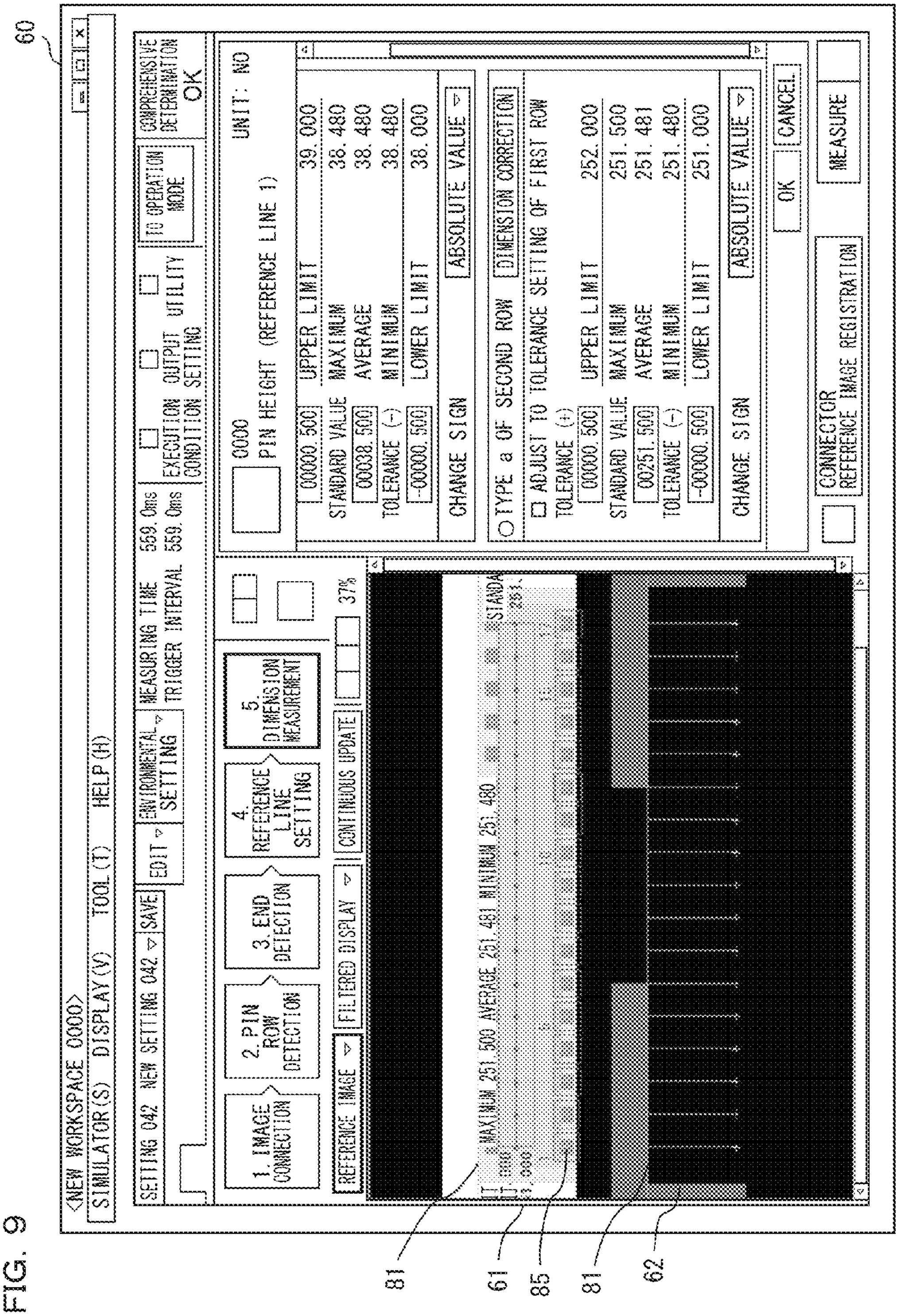
FIG. 9 is a diagram illustrating an example in which a pin height is obtained for each pin of the second row.

FIG. 9 illustrates an example in which a pin height is obtained for each pin of the second row. In order to establish the outer edge of the upper side of the housing 40 from the back-light image 62, the image processing section 30 detects the position of the upper-right corner and the position of the upper-left corner according to image recognition and determines a straight line (an equation of a straight line) connecting the two as the reference line 81. Further, the image processing section 30 detects the center position of each pin of the second row as a reference point 85 from the front-light image 61. The image processing section 30 calculates a distance from the reference point 85 of each pin to the reference line 81 as the height of each pin.

<Setting of Number of Imaging Operations>

Figure 10:
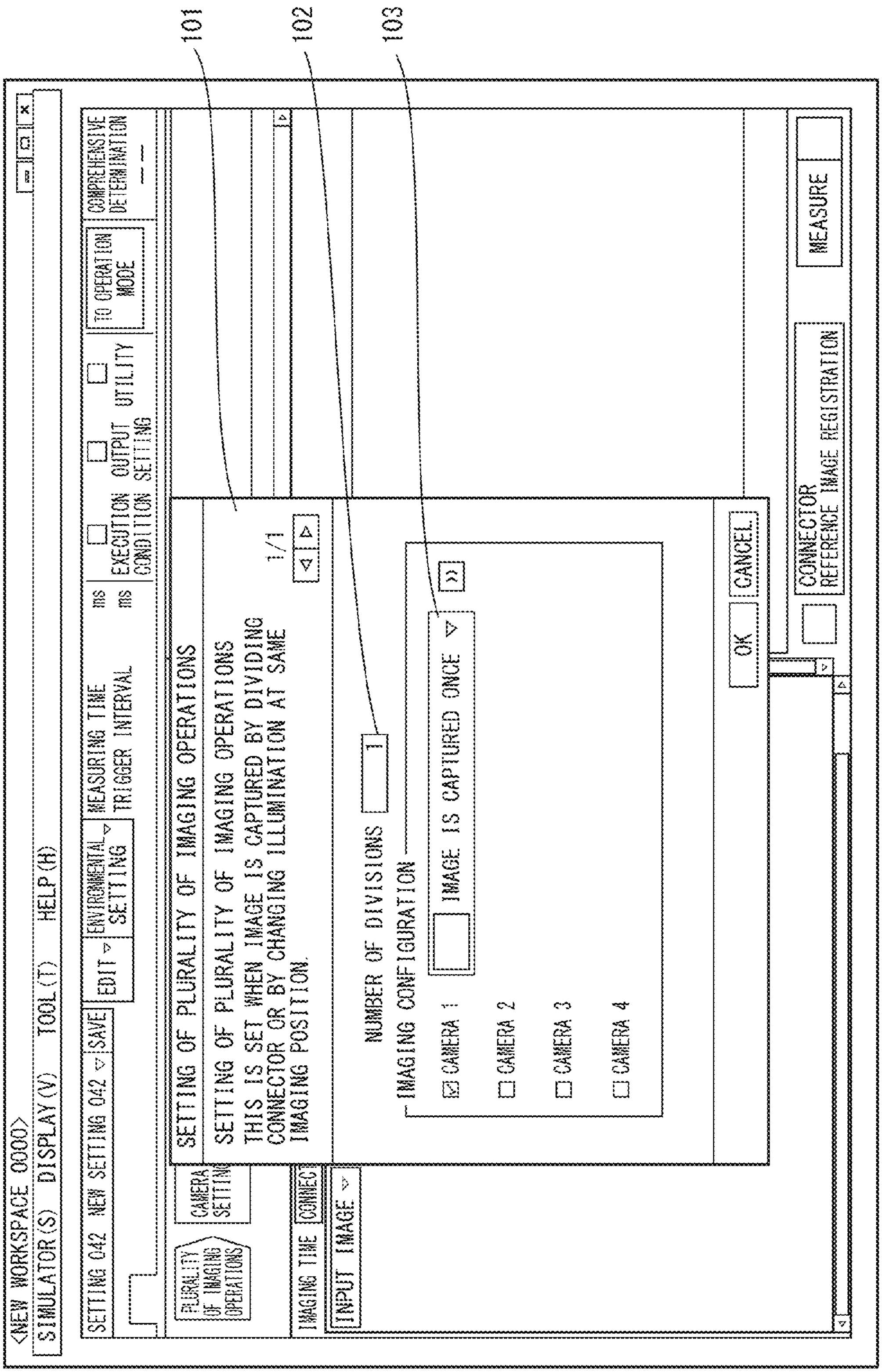
FIG. 10 is a diagram illustrating a dialog for setting the number of imaging operations.
Figure 11:
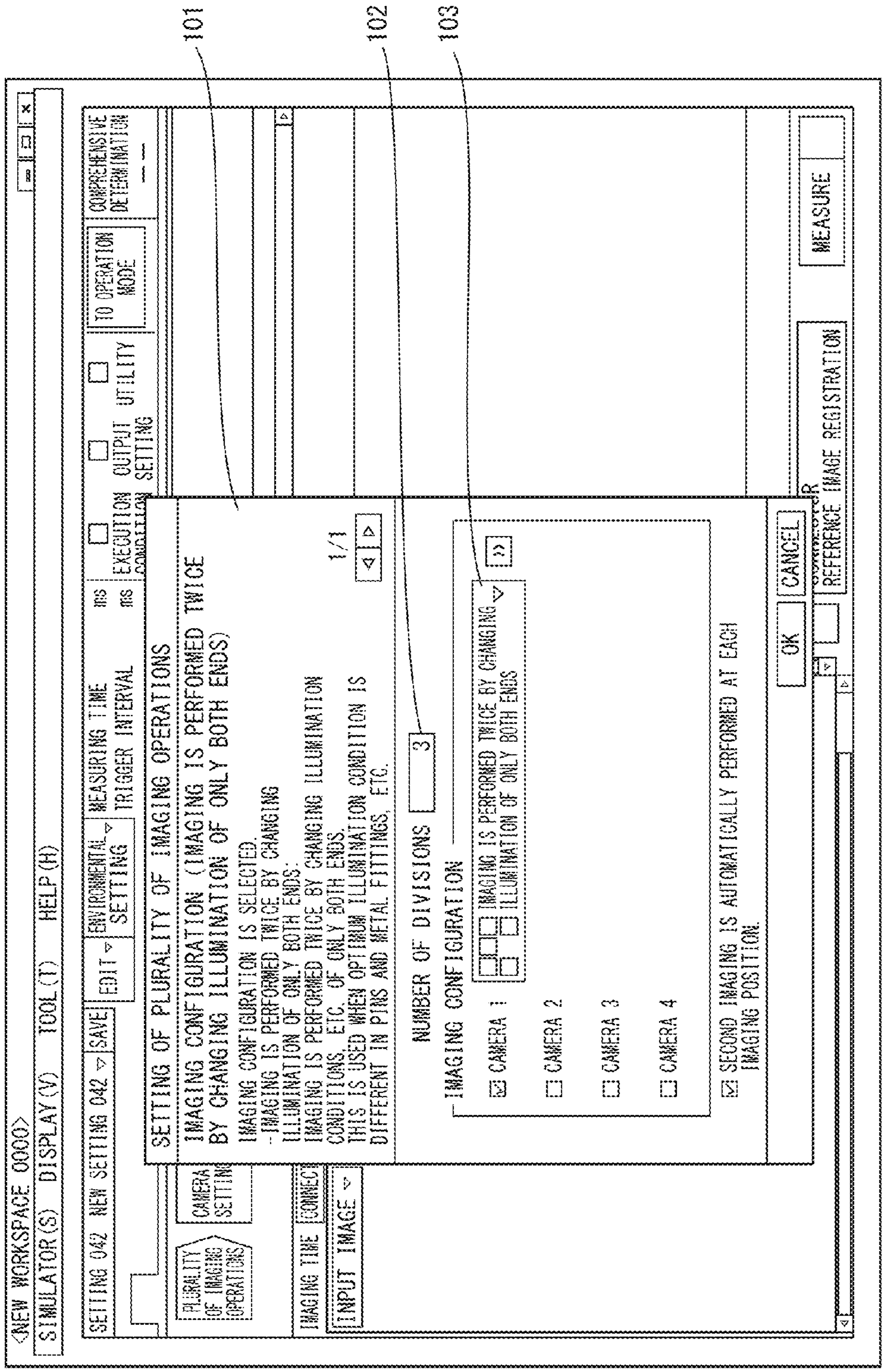
FIG. 11 is a diagram illustrating the dialog for setting the number of imaging operations.

FIGS. 10 and 11 each illustrate a dialog 101 for setting the number of imaging operations. In the dialog 101, an input field 102 of the number of divisions of an image and a selection field 103 of the number of cameras or an imaging technique are shown. When the number of divisions is set to 1, this means that the entire inspection object 8 is held in one image. When the number of divisions is set to 3, this means that the entire inspection object 8 is divided into three images and held therein. As illustrated in FIG. 11, in the selection field 103, it is possible to select an imaging technique of capturing an image while changing illumination at only both ends of the inspection object 8, for example.

Figure 12:
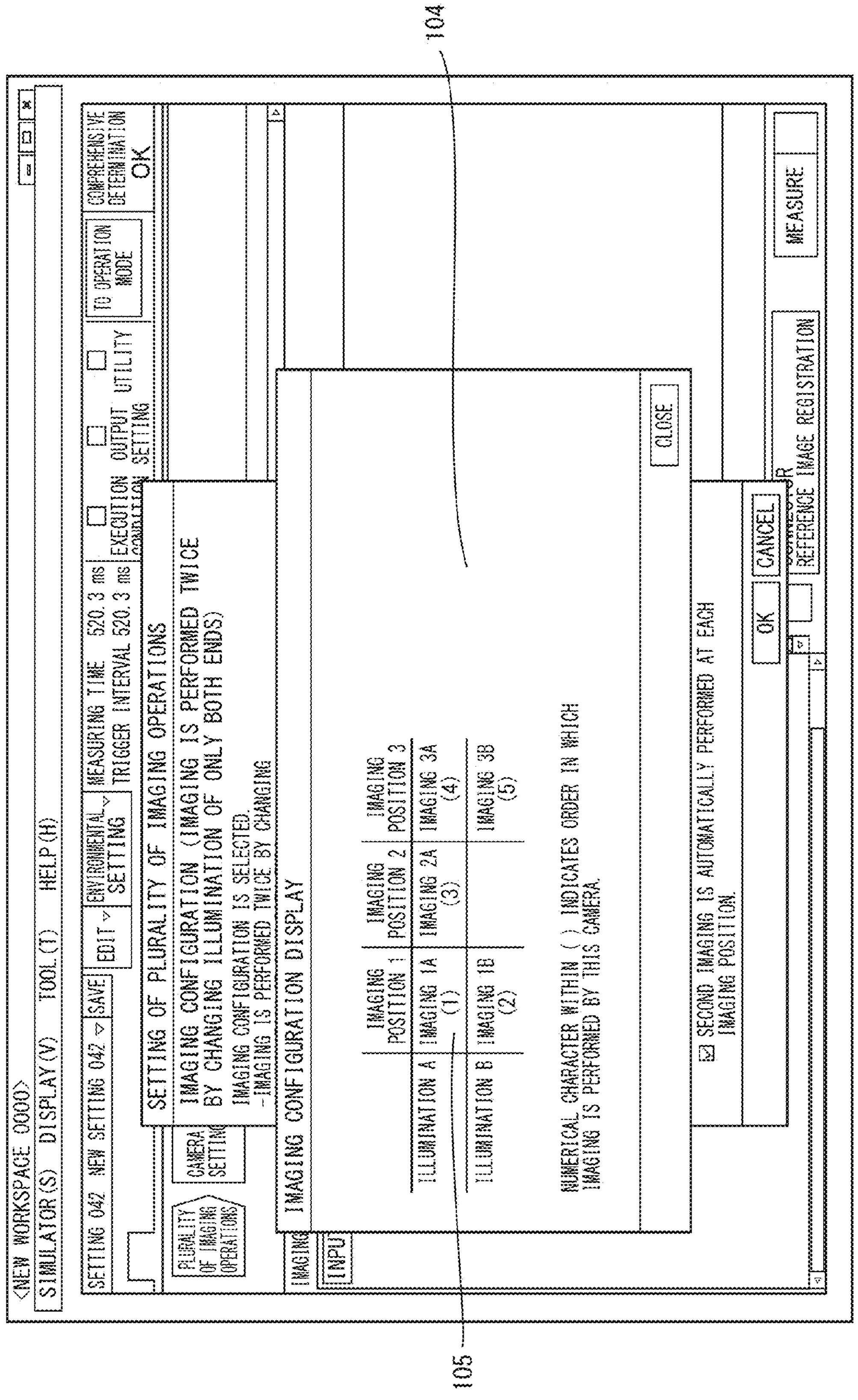
FIG. 12 is a diagram illustrating a dialog visually indicating the number of imaging operations set by a user.

FIG. 12 illustrates a dialog 104 visually indicating the number of imaging operations set by a user. This example shows that an imaging operation is performed at three imaging positions with an illumination A (the front light 51) and that an imaging operation is performed at two imaging positions excluding a middle position with an illumination B (the back light 52). In addition, imaging order 105 is also shown in order to clearly specify the imaging order to the user. In this example, a first imaging operation is performed at a first imaging position using the illumination A and a second imaging operation is performed at the first imaging position using the illumination B. Thereby, the user easily understands that the inspection object 8 is to be moved when the first and second imaging operations have ended.

<Connector Positional Deviation Correction>

When an image for a quality determination is captured while the inspection object 8 is conveyed by the conveyor device 7, the position of the inspection object 8 may be deviated from the ideal position. Here, the ideal position is a layout position of a non-defective workpiece when a model image for pattern matching is captured by the camera 4. Because the non-defective workpiece is accurately arranged manually, the position is accurately determined with respect to the camera 4. Consequently, in order to improve the accuracy of pattern matching and a quality determination when the image of the inspection object 8 is captured in an actual manufacturing line, positional deviation correction in which a captured image is rotated or shifted in left, right, upward, and downward directions is necessary.

Incidentally, a plurality of imaging operations may be performed at the same position of the inspection object 8 while changing the illumination technique as described above. For example, because the imaging operation is performed at the same position without moving the inspection object 8 in the front-light image 61 and the back-light image 62, respective positional deviation amounts should be consistent. Accordingly, a correction amount of the back-light image 62 is set using a positional deviation amount obtained from the front-light image 61 among images of respective imaging positions or its correction amount. When a positional deviation of the connector occurs, the position of the connector is detected for an accurate inspection in a subsequent-stage inspection and a deviation amount is corrected.

As described above, in this embodiment, the image processing section 30 obtains a correction amount of a positional deviation from one image among a plurality of images obtained by imaging the same position of the inspection object 8, corrects the position of each of the plurality of images by the obtained correction amount, and makes a quality determination using the corrected image.

Figure 13:
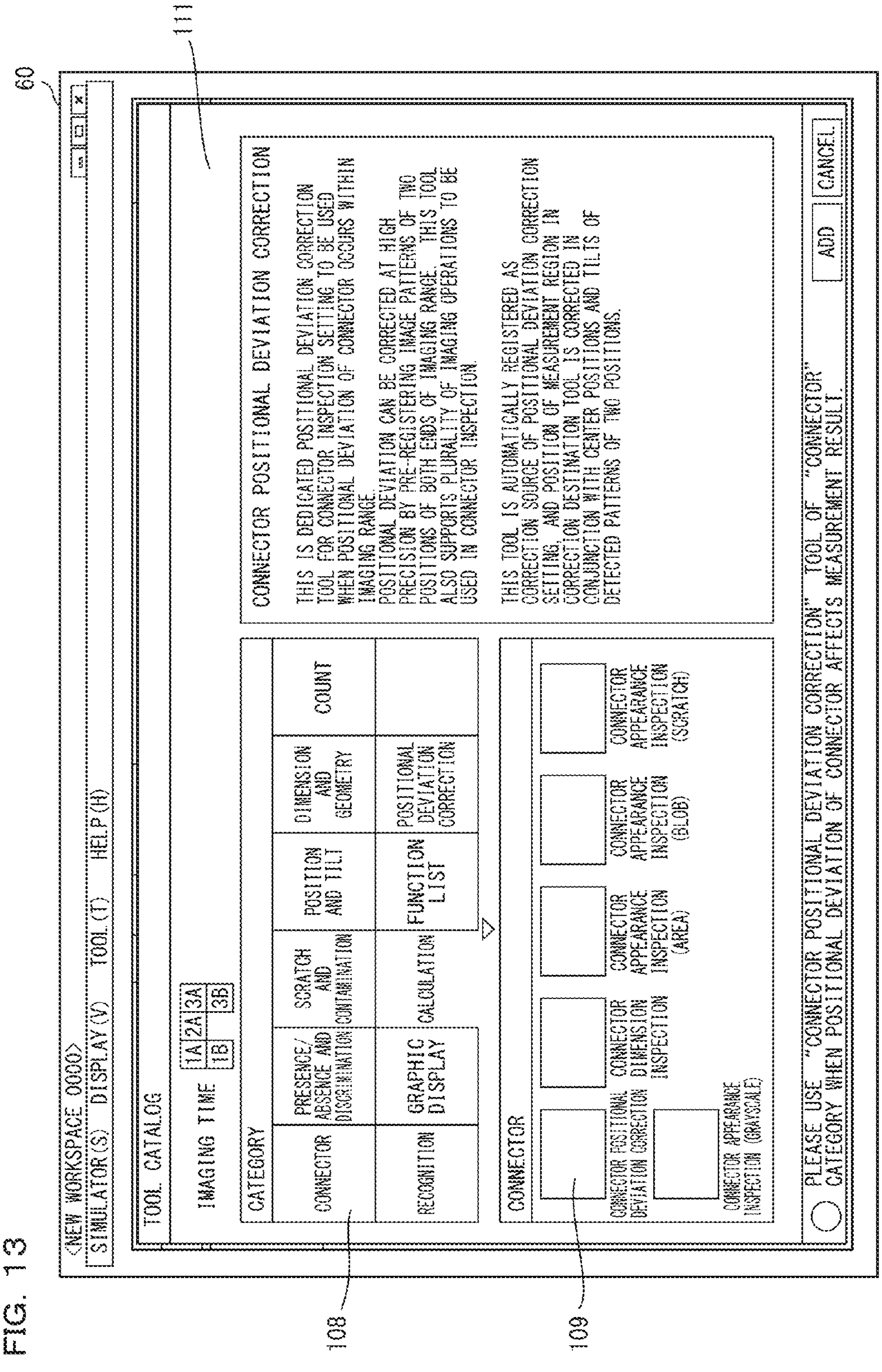
FIG. 13 is a diagram illustrating selection of a connector category with a mouse from a tool catalog indicating categories of a plurality of image processing tools and further selection of connector positional deviation correction as an image processing tool.

FIG. 13 is a diagram illustrating selection of a connector category 108 with the mouse 9 from a tool catalog 111 indicating categories of a plurality of image processing tools and further selection of connector positional deviation correction as an image processing tool.

Figure 14:
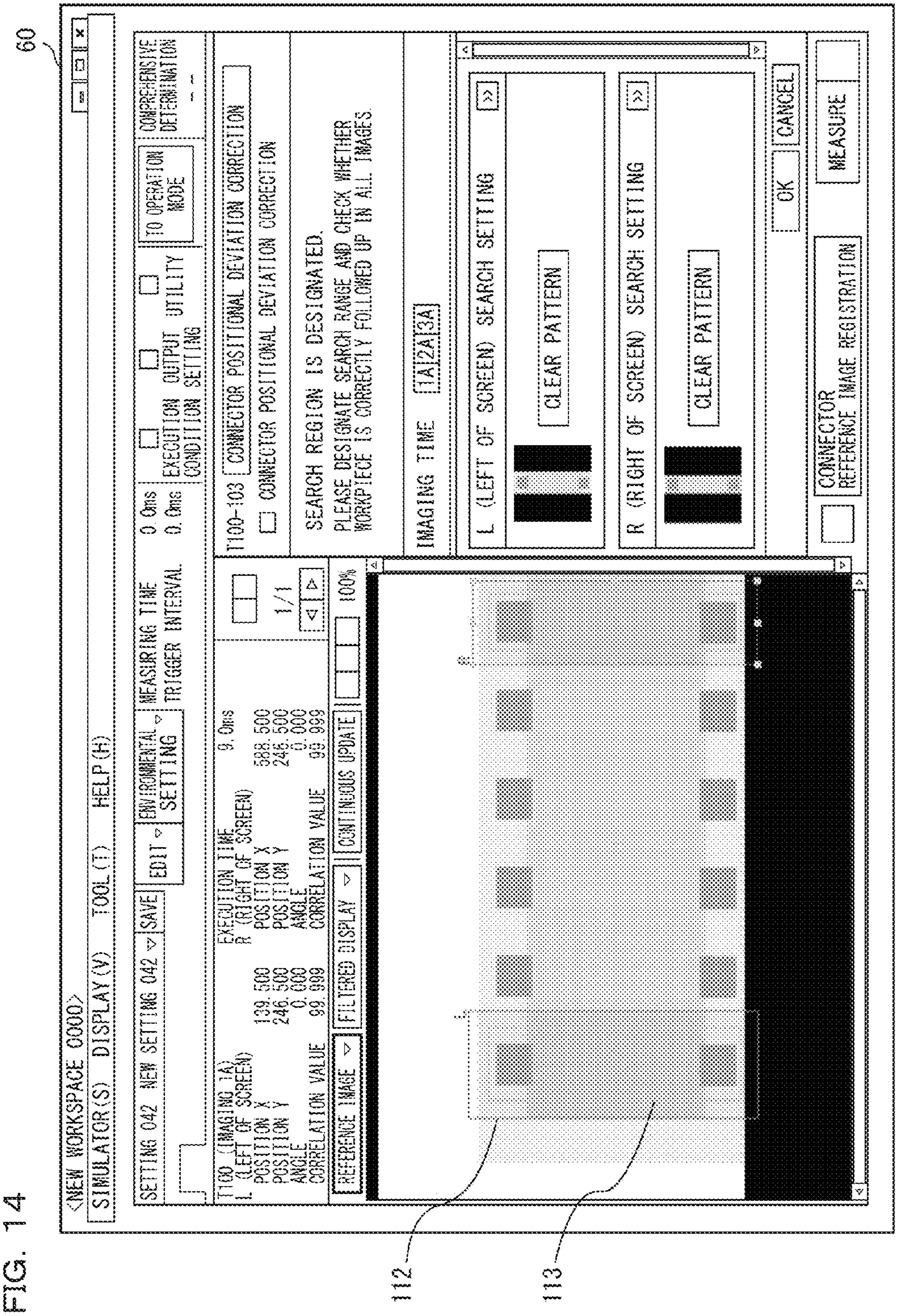
FIG. 14 is a diagram illustrating a UI for setting parameters necessary for the connector positional deviation correction.
Figure 15:
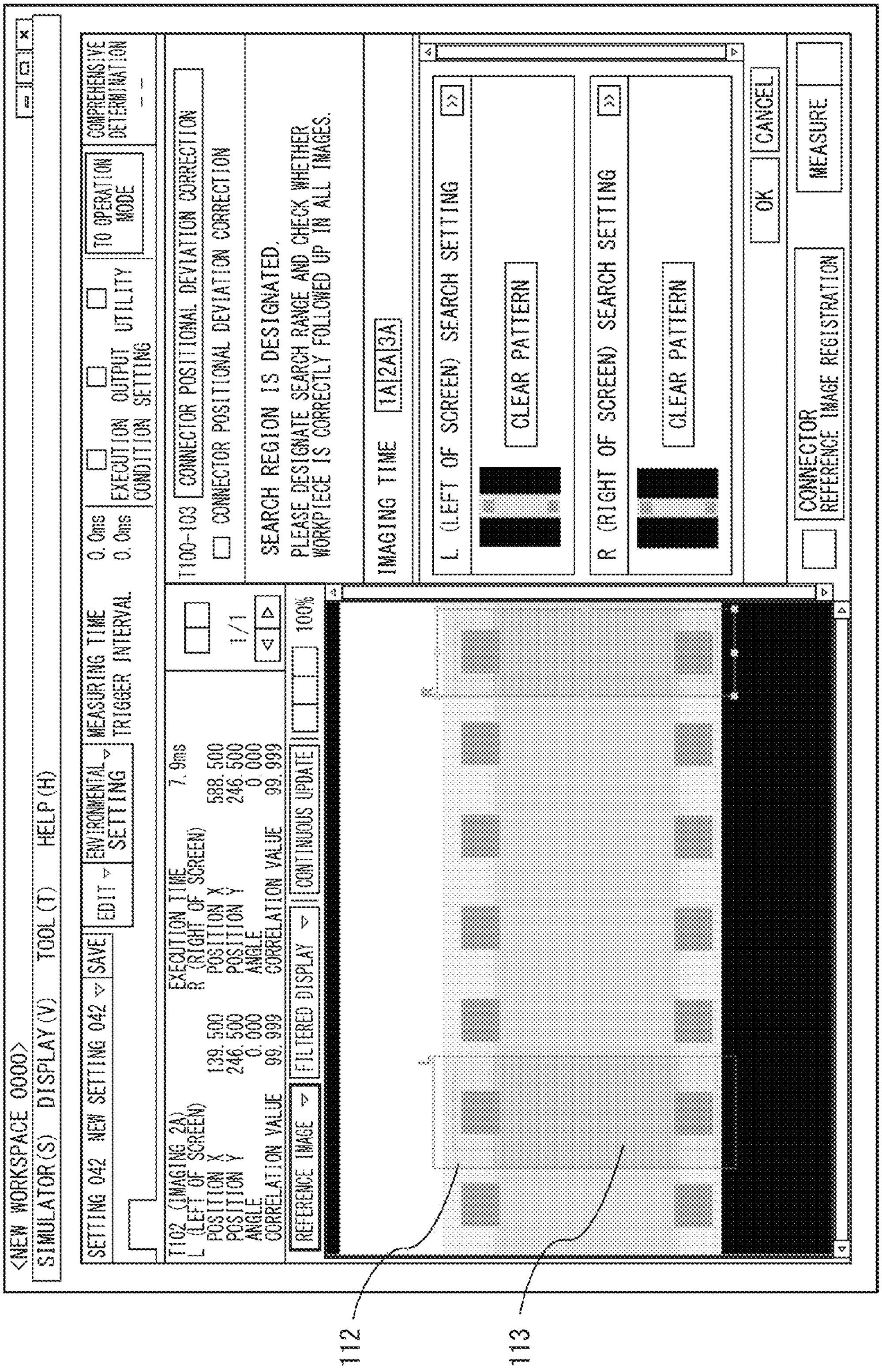
FIG. 15 is a diagram illustrating the UI for setting parameters necessary for the connector positional deviation correction.
Figure 16:
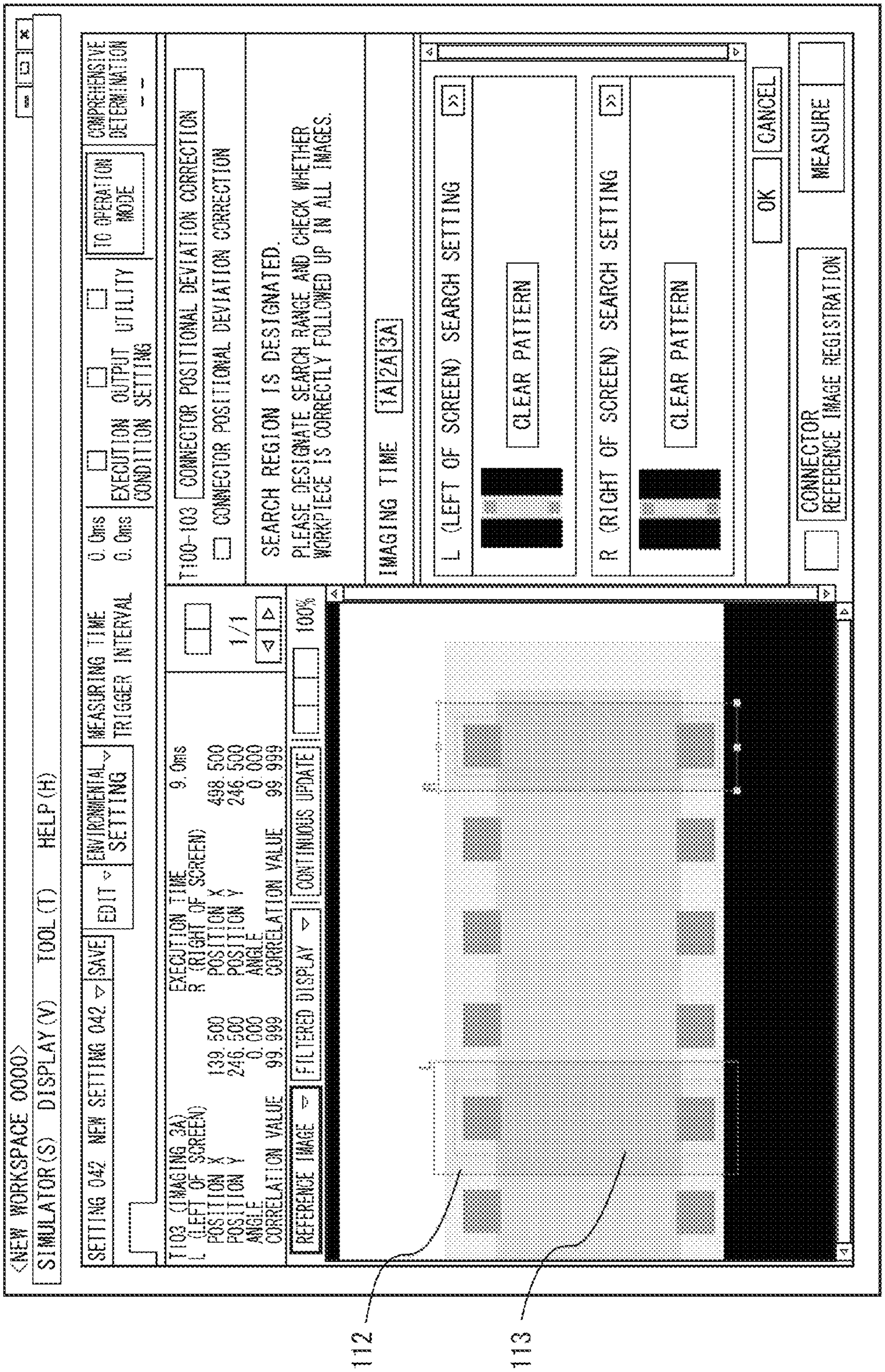
FIG. 16 is a diagram illustrating the UI for setting parameters necessary for the connector positional deviation correction.

FIGS. 14, 15, and 16 each illustrate a UI for setting a parameter necessary for the connector positional deviation correction (FIGS. 14 to 16 are UIs corresponding to images 1A to 3A, respectively). Here, two search regions 112 are set with the mouse 9. As illustrated on the right of FIG. 14, when a model image (search pattern) is pre-registered by the user and a search region 112 is set with the mouse 9, whether there is a portion pattern-matching a model image within the search region 112 is searched for in real time. Accordingly, when the model image is found, the model image is displayed as an inspection region 113 on a screen. That is, in FIG. 14, the model image is found within the search region 112, and the inspection region 113 is displayed. Here, the search region 112 is a region indicating a range in which the model image can be moved. The inspection region 113 is a region including a portion (model image) serving as a pattern matching target (a region in which the model image is found in FIG. 14 as described above). Two search regions 112 are set because a tolerance in manufacturing of the inspection object is considered or because a deviation in position/tilt is accurately corrected when the inspection object is conveyed. If positions of two inspection regions 113 are identified in the two search regions 112, it is possible to calculate a positional deviation amount of a connector position from the identified positions.

As illustrated in FIGS. 14, 15, and 16, two search regions 112 for the positional deviation correction and two inspection regions 113 are set in each of a left end, a middle portion, and a right end of the connector. Because positional deviation amounts in the left end, the middle portion, and the right end of the connector may be the same, the positional deviation amount may be obtained from one of the left end, the middle portion, and the right end. However, a positional deviation correction amount may be obtained from three positions of the left end, the middle portion, and the right end in order to improve the precision of the positional deviation correction.

Figure 17:
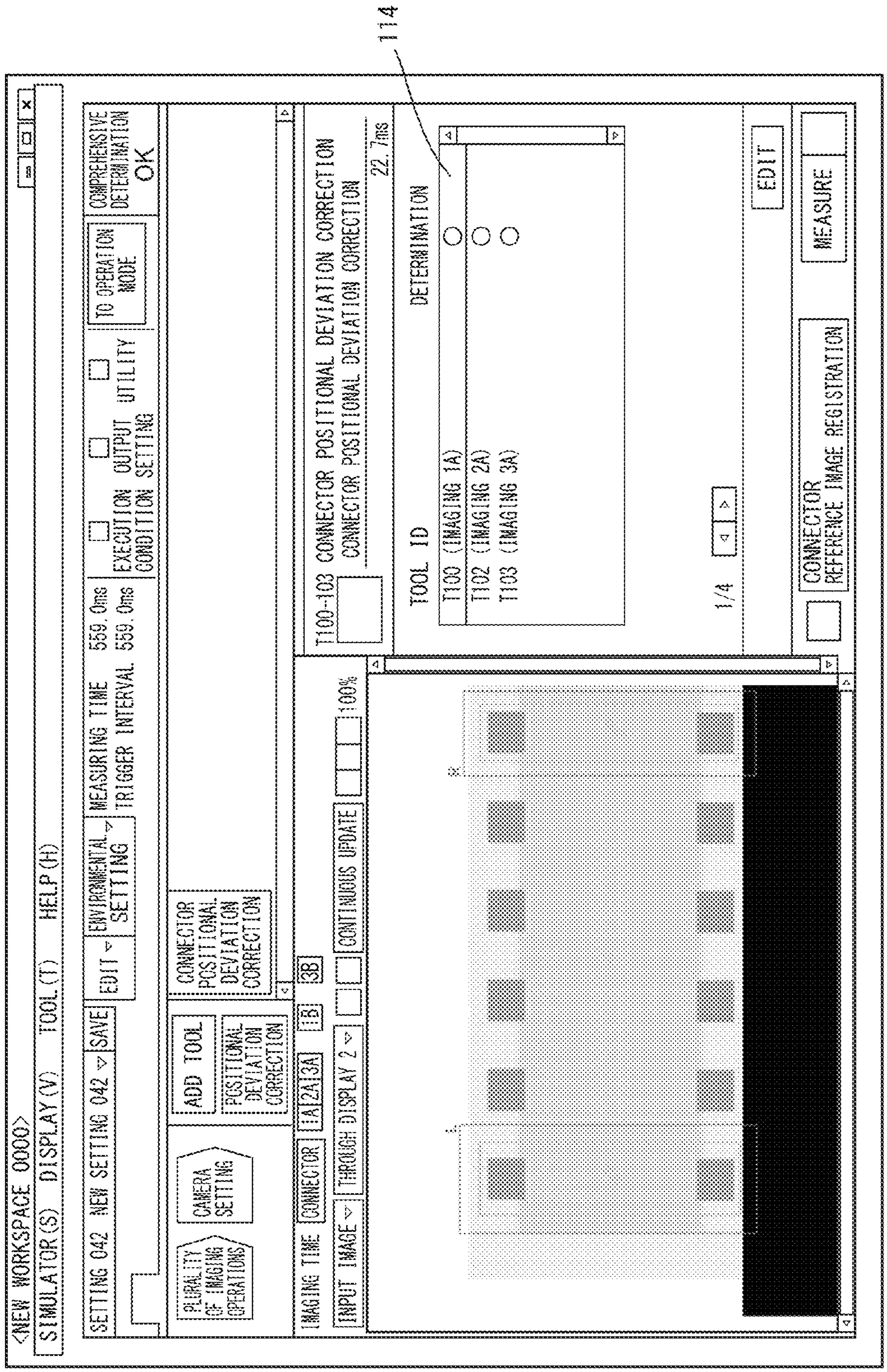
FIG. 17 is a diagram illustrating an example of the UI indicating that settings for the connector positional deviation correction have ended.

FIG. 17 is an example of a UI indicating that an operation of setting the connector positional deviation correction has ended. The image processing section 30 may execute the positional deviation correction on a non-defective product imaged by the camera 4 using a parameter set with the mouse 9 and display an OK mark 114 on the monitor 10 indicating success when the positional deviation correction has been made successfully.

<Addition of Connector Dimension Inspection Tool>

Figure 18:
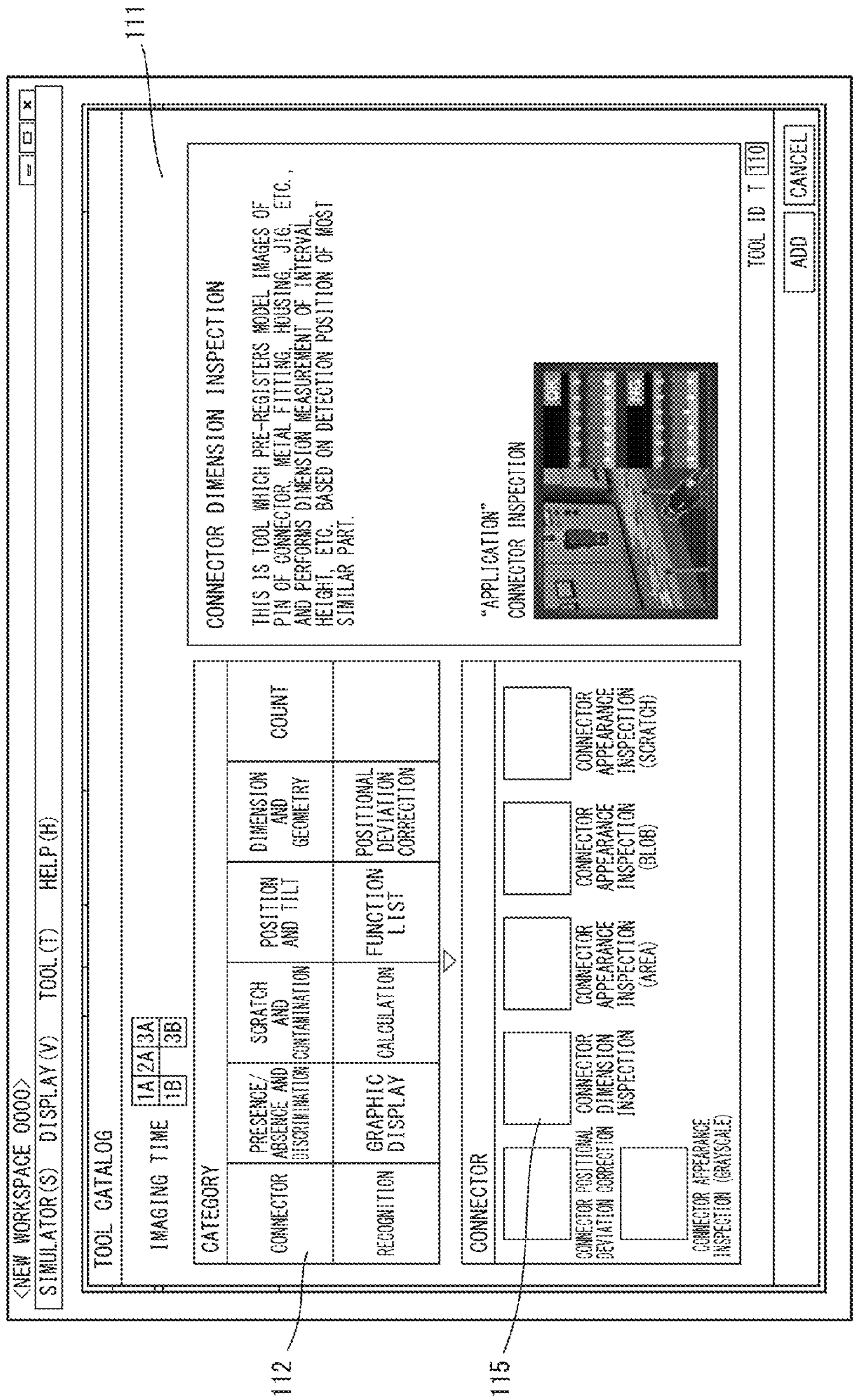
FIG. 18 is a diagram illustrating selection of a connector category with the mouse from a tool catalog indicating categories of a plurality of image processing tools and further selection of a connector dimension inspection tool as an image processing tool.

FIG. 18 is a diagram illustrating selection of a connector category 108 with the mouse 9 from a tool catalog 111 indicating categories of a plurality of image processing tools and further selection of a connector dimension inspection tool 109 as an image processing tool. If a button indicating the connector dimension inspection tool 109 is clicked, the screen transitions to a setting screen. For the transition to the setting screen, the addition button may be further clicked.

Setting of Image Connection Parameter

There is an image connection parameter as one of setting items of the connector dimension inspection tool. When no image is connected, an operation of setting the parameter is unnecessary.

Figure 19:
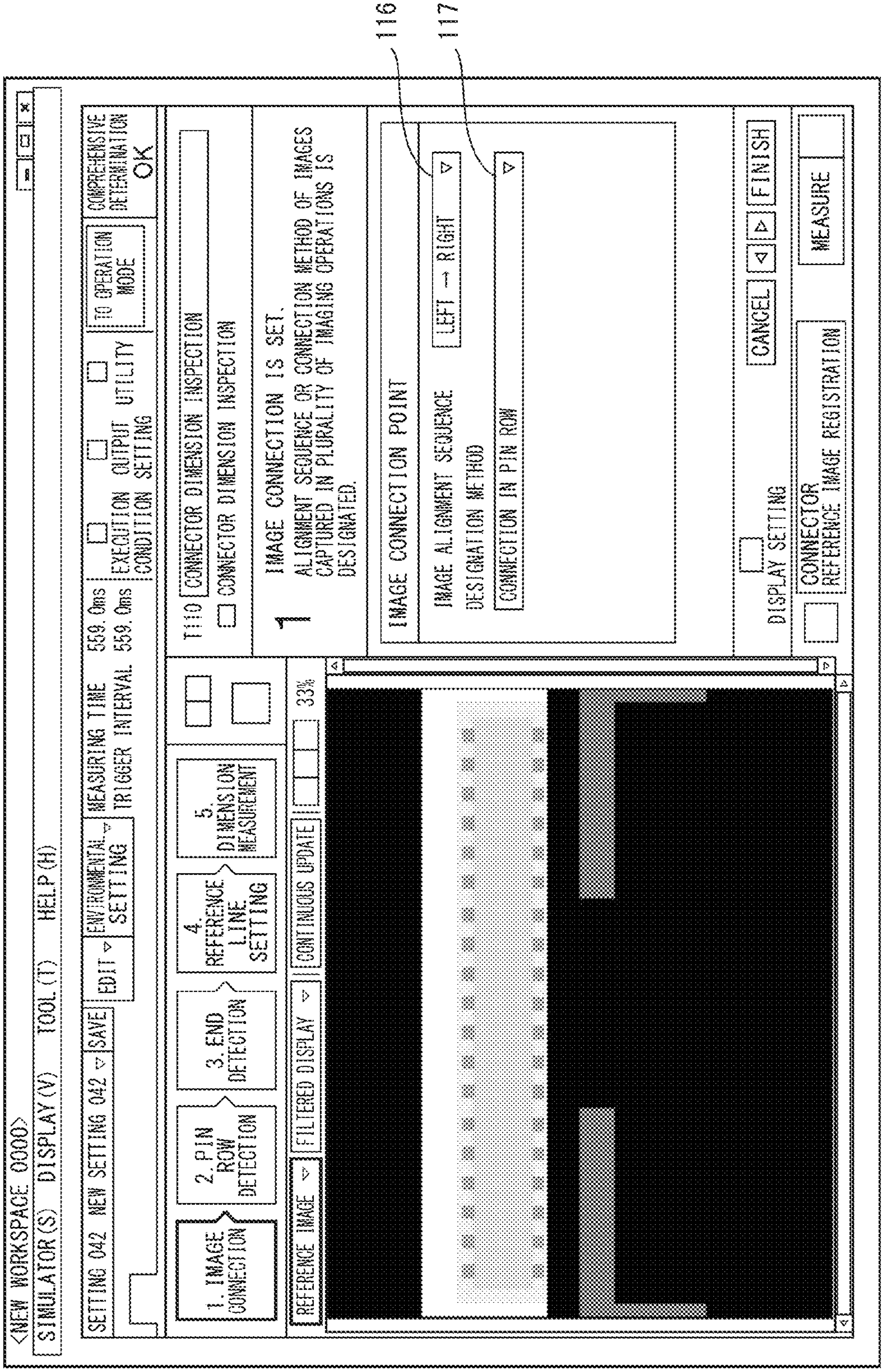
FIG. 19 is a diagram illustrating a setting screen on which an image connection point is set.

FIG. 19 is a diagram illustrating a setting screen on which an image connection point is set. In the screen, an order 116 of image alignment and a connection method 117 of designating a connection technique can be selected with the mouse 9. For example, if an item "left→right" is selected as the order 116 of the image alignment, this indicates that an image of the inspection object 8 is captured from left to right. If an item "connection in pin row" is selected as the connection method 117, the image processing section 30 detects a pin row from each image and connects a plurality of images so that the overall pin row serves as one row.

Setting of Pin Row Detection Parameter

Figure 20:
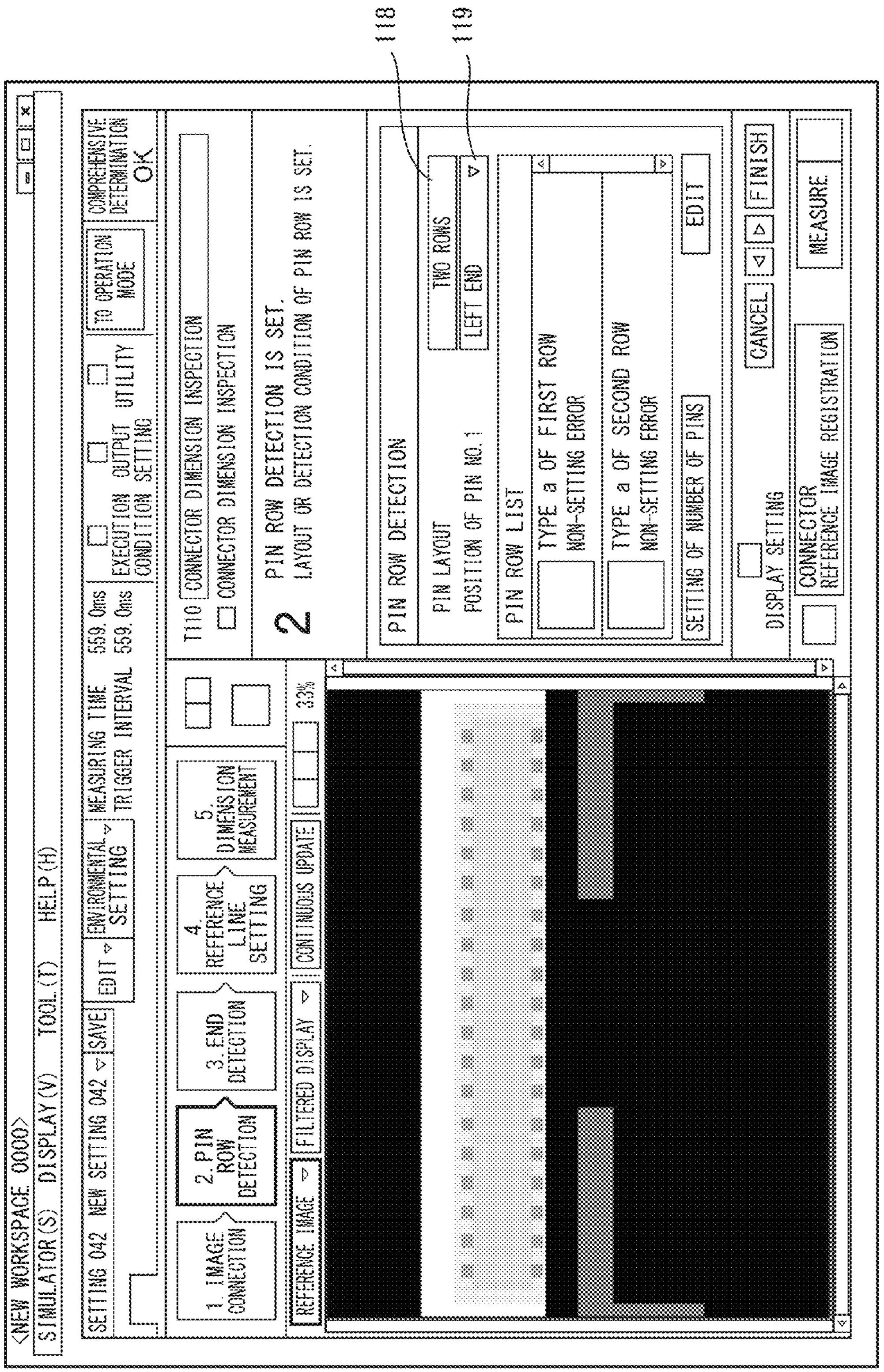
FIG. 20 is a diagram illustrating a setting screen for a pin row detection parameter.

FIG. 20 illustrates a setting screen of a pin row detection parameter. In this example, pin layout 118 is a setting item for setting the number of rows in which pins are arranged. A position 119 of the 1st pin is a setting item for setting which of a plurality of pins arranged in one row is the 1st pin. In this example, because the connector, which is the inspection object 8, has two rows, an item "two rows" for the pin layout 118 is selected with the mouse 9.

Registration of Pin Model

The connector has a large number of pins and it is necessary to inspect all pins. Accordingly, it is necessary to register a model image of each pin of an inspection object and its position for use in a non-defective product determination.

Figure 21:
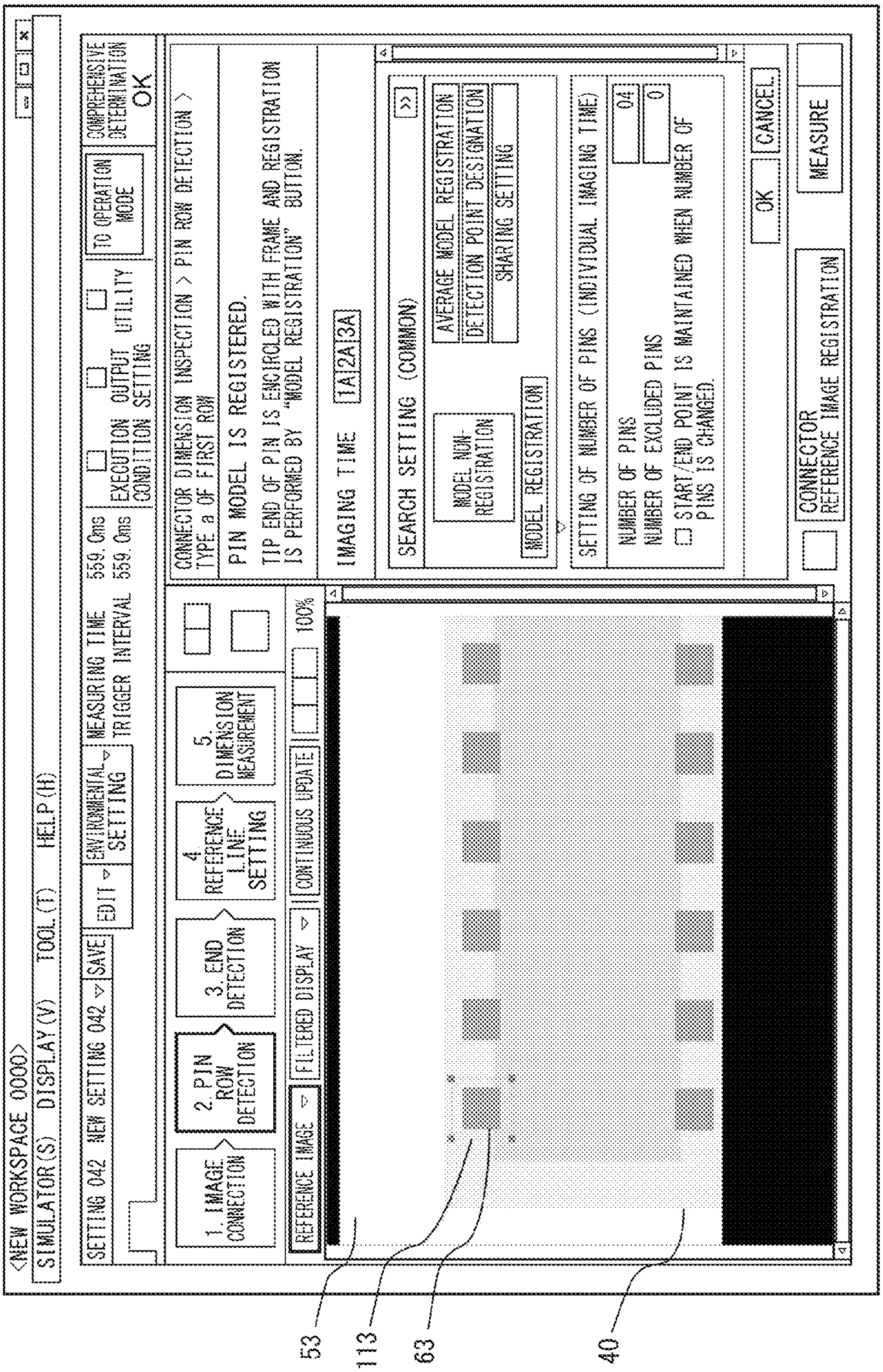
FIG. 21 is a diagram illustrating a pin model registration screen.

FIG. 21 illustrates a registration screen of a pin model. The CPU 22 enlarges and displays an image 53 of a left end of the connector within the registration screen. This is to easily register the pin model. The user sets an inspection region 113 to include the 1st pin 63. The CPU 22 stores a partial image encircled with the inspection region 113 as the model image in a memory. A position and size of the inspection region 113 are changed by the CPU 22 in association with an operation of the mouse 9.

Figure 22:
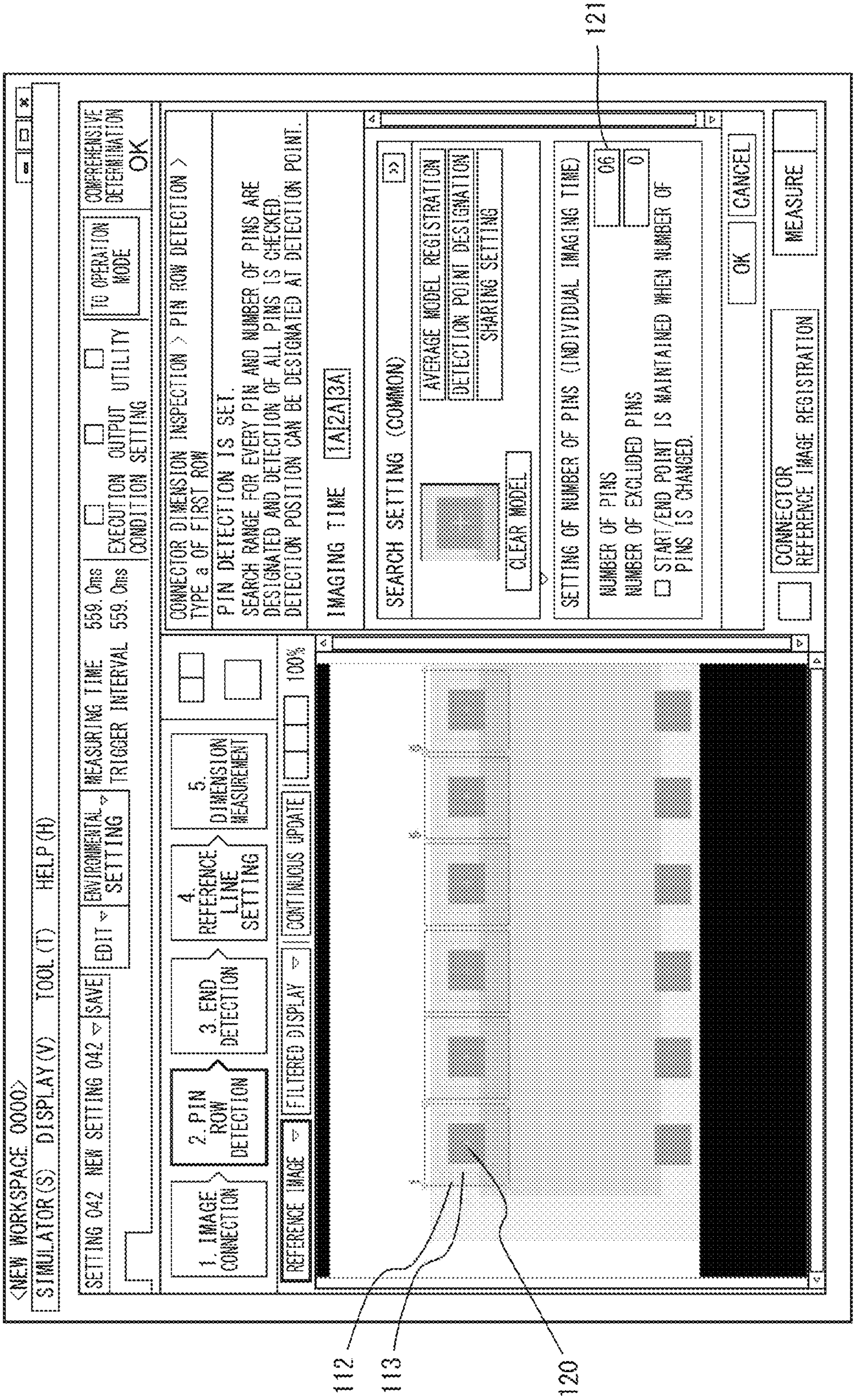
FIG. 22 is a diagram illustrating a pin detection setting screen.

FIG. 22 illustrates a setting screen of pin detection. The CPU 22 arranges a reference point 120 at the center of the inspection region 113, and arranges the search region 112 to surround the inspection region 113. A position of the inspection region 113, a position of the reference point 120, and a position of the search region 112 are stored by the CPU 22 in the memory. As described above, the inspection region 113 represents a region detected as a result of pattern matching with the model image set in FIG. 21 within the search region 112. That is, in FIG. 22, the inspection region 113 represents a detection result of pattern matching with the model image.

As described above, the search region 112, the inspection region 113, the reference point 120, and the like should be set for all pins. However, when this setting work is manually performed, a heavy burden is imposed on the user. Accordingly, in this embodiment, the user can semi-automate an operation of setting the search region 112, the inspection region 113, and the reference point 120 for each of pins including a 2nd pin and subsequent pins by setting a pin count 121, which is one of setting items, using the mouse 9. According to the input pin count 121, the CPU 22 sets the search region 112, the inspection region 113, and the reference point 120 for each of 6 certain pins by copying the search region 112, the inspection region 113, and the reference point 120 in the right direction. It is assumed that respective pins are arranged at equal intervals and sizes of the respective pins are also consistent with each other. The user may finely adjust the search region 112, the inspection region 113, and the reference point 120 set by the CPU 22 for each pin with the mouse 9. According to an input from the mouse 9, the CPU 22 corrects coordinates (positions) of the search region 112, the inspection region 113, and the reference point 120 and stores the corrected coordinates in a memory.

Figure 23:
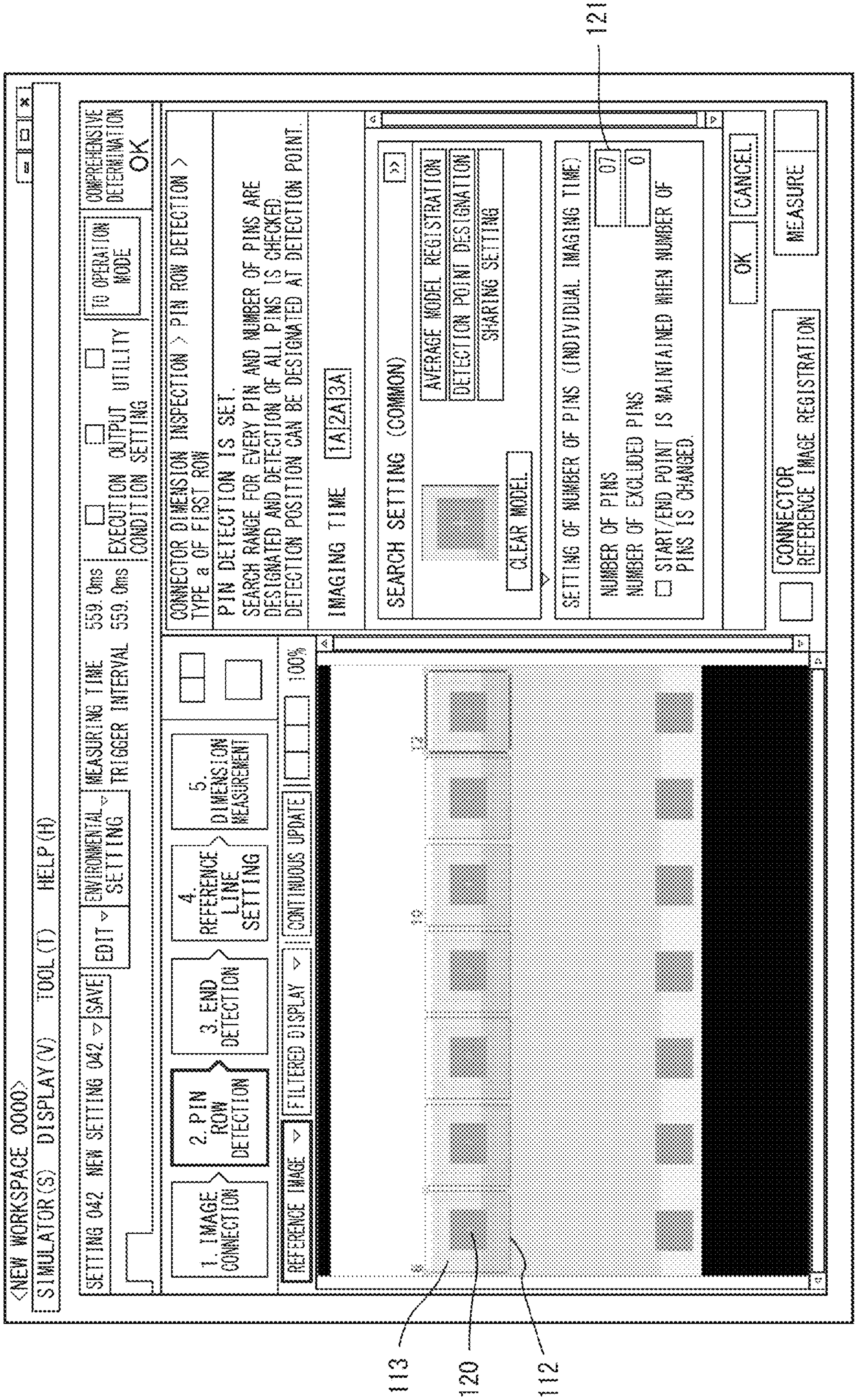
FIG. 23 is a diagram illustrating a setting screen of a search region, an inspection region, and a reference point in a middle portion and a right end portion of the connector.
Figure 24:
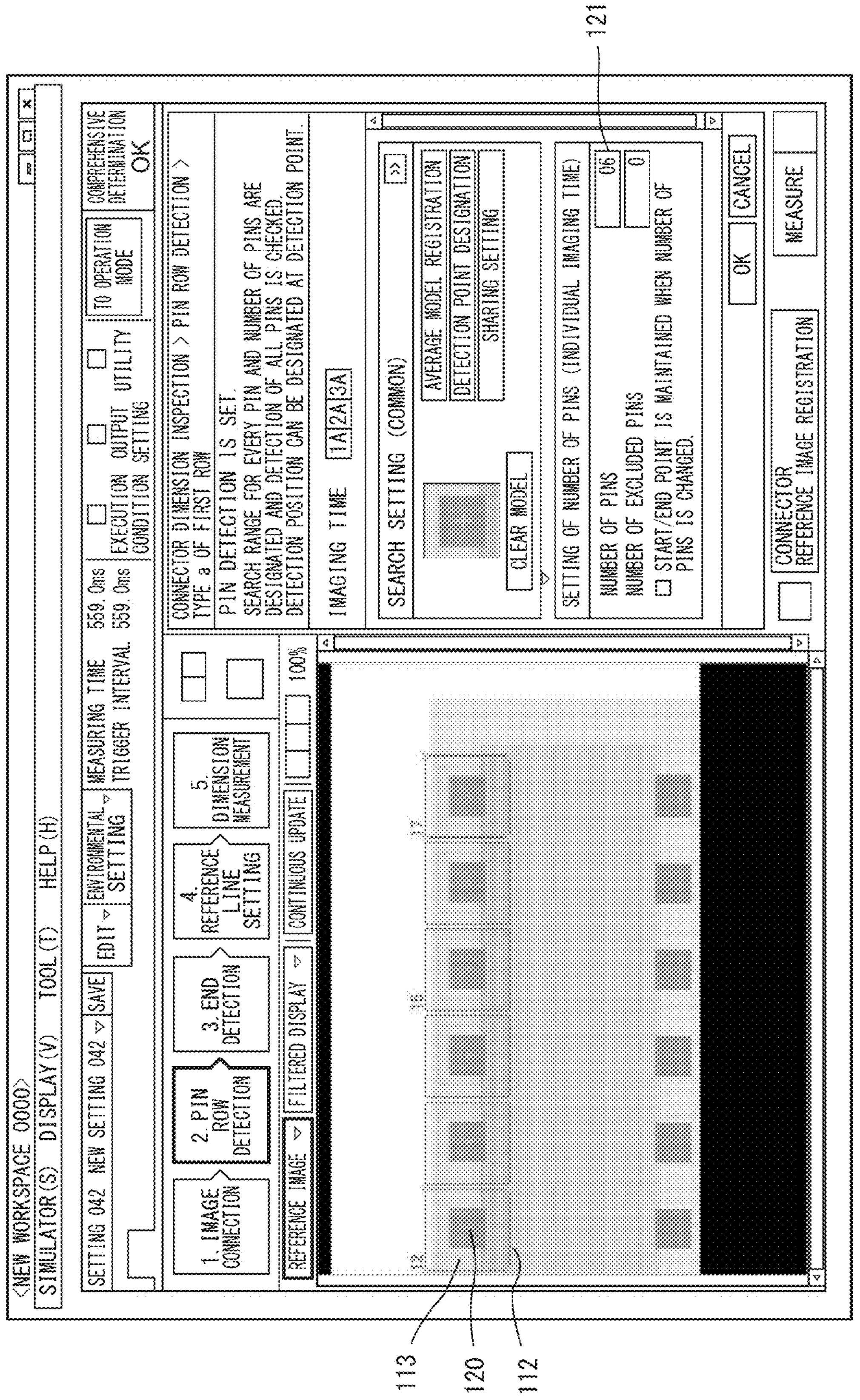
FIG. 24 is a diagram illustrating the setting screen of the search region, the inspection region, and the reference point in the middle portion and the right end portion of the connector.

FIGS. 23 and 24 are diagrams each illustrating a setting screen of a search region 112, an inspection region 113, and a reference point 120 in a middle portion and a right end portion of the connector. The search region 112, the inspection region 113, and the reference point 120 for the middle portion and the right end portion of the connector are also set in a procedure similar to that for the left end portion of the connector.

That is, the CPU 22 sets the search region 112, the inspection region 113, and the reference point 120 for each pin of the middle portion and the right end portion of the connector using data of the search region 112, the inspection region 113, and the reference point 120 of the 1st pin and the pin count 121.

Figure 25:
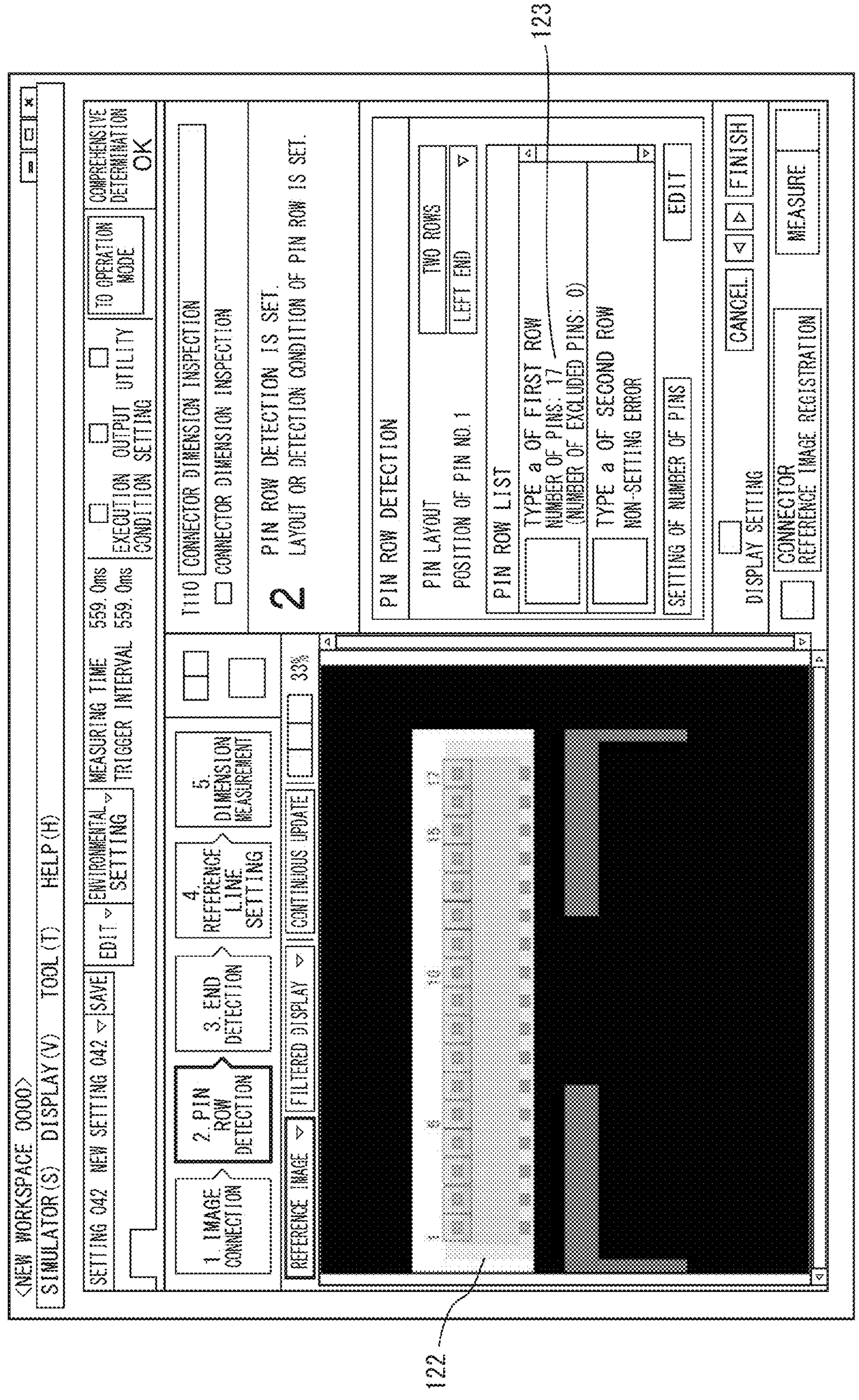
FIG. 25 is a diagram illustrating a screen indicating that registration of a pin model of a first row (setting of pin row detection) has been completed.

FIG. 25 illustrates a screen indicating that registration of a pin model of a first row has been completed. In this screen, an entire screen 122 of the connector is displayed along with the search region 112, the inspection region 113, and the reference point 120. The CPU 22 may display a total pin count 123 by obtaining a sum of input pin counts on the monitor 10.

Although the pins of the first row have been described in FIGS. 21 to 25, it is also possible to execute pin registration for pins of a second row in a similar procedure.

Setting of End Detection Parameter

When an appearance inspection of the connector is performed, it is necessary to detect a position of an end (corner) of the connector as described above. When metal fittings and the like are provided at both ends of a connector housing, the metal fitting instead of the corner may be detected as the end. In this case, it is only necessary to set a search region, an inspection region, and a detection point (reference point) for the metal fitting.

Figure 26:
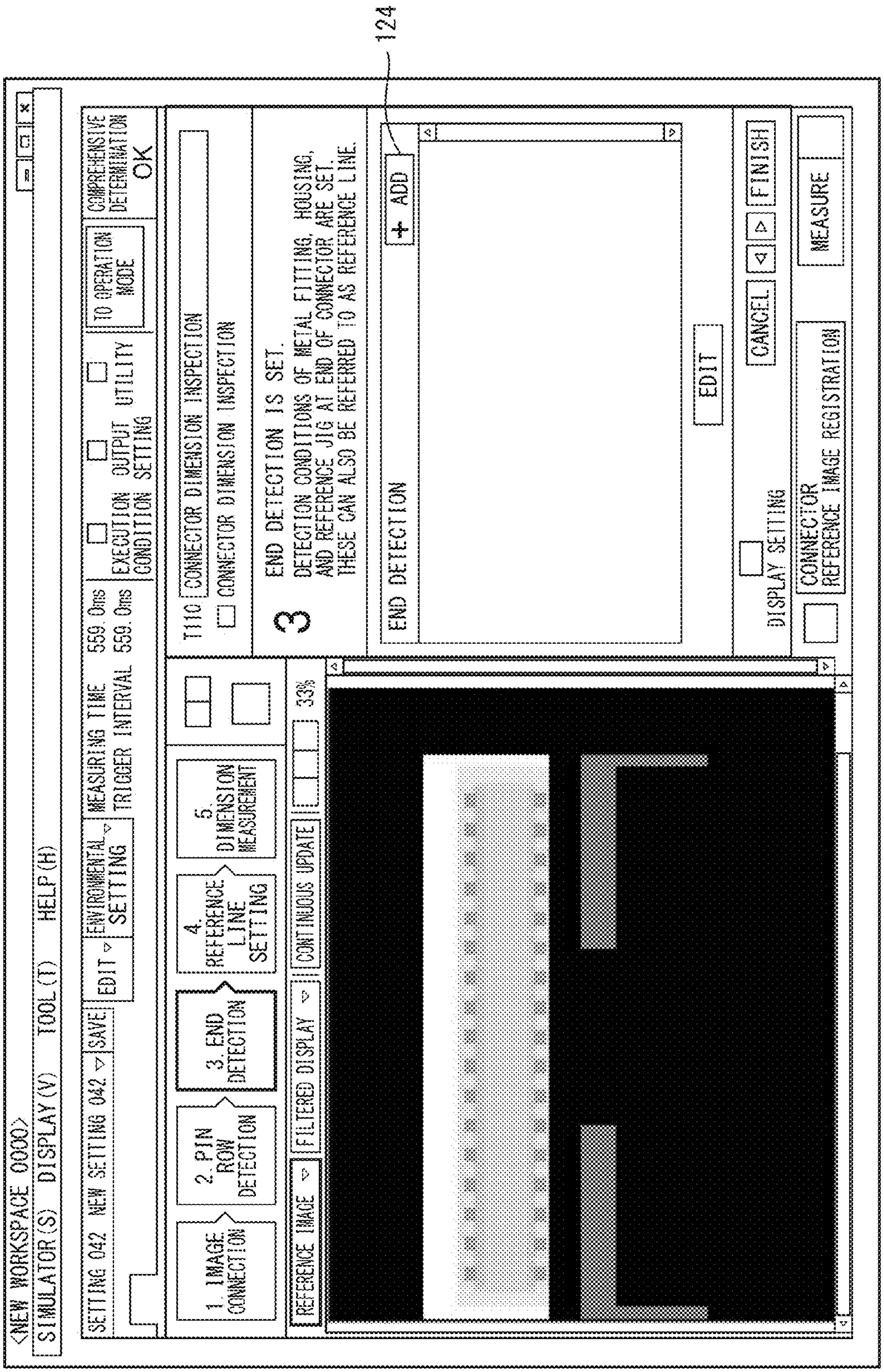
FIG. 26 is a diagram illustrating a setting screen on which a setting operation related to end detection of the connector is performed.

FIG. 26 is a diagram illustrating a setting screen on which a setting operation related to end detection of the connector is performed. The number of ends to be detected differs according to a type of connector. Accordingly, a necessary number of ends are set by pressing an addition button 124 using the mouse 9.

Figure 27:
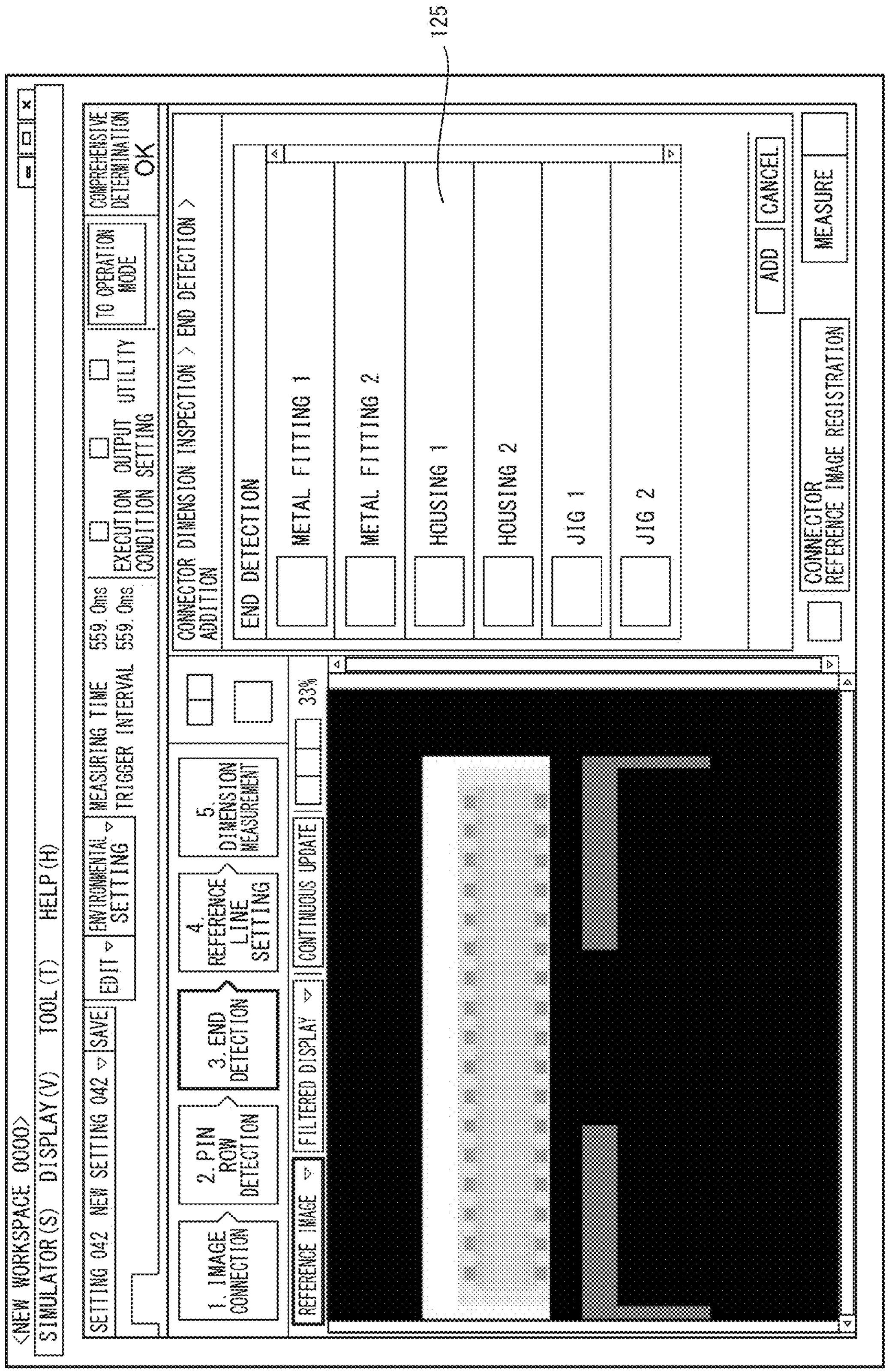
FIG. 27 is a diagram illustrating a selection item for selecting an end serving as an end detection target.

FIG. 27 illustrates a selection item 125 for selecting an end serving as an end detection target. According to a type of connector, there are a case in which a metal provided in the connector should be an end, a case in which the housing of the connector should be an end, a case in which a jig for conveying the connector should be an end, and the like. Accordingly, the user selects an end detection target through an operation of the mouse 9 from the selection item 125 in accordance with a type of connector serving as the inspection object 8.

Figure 28:
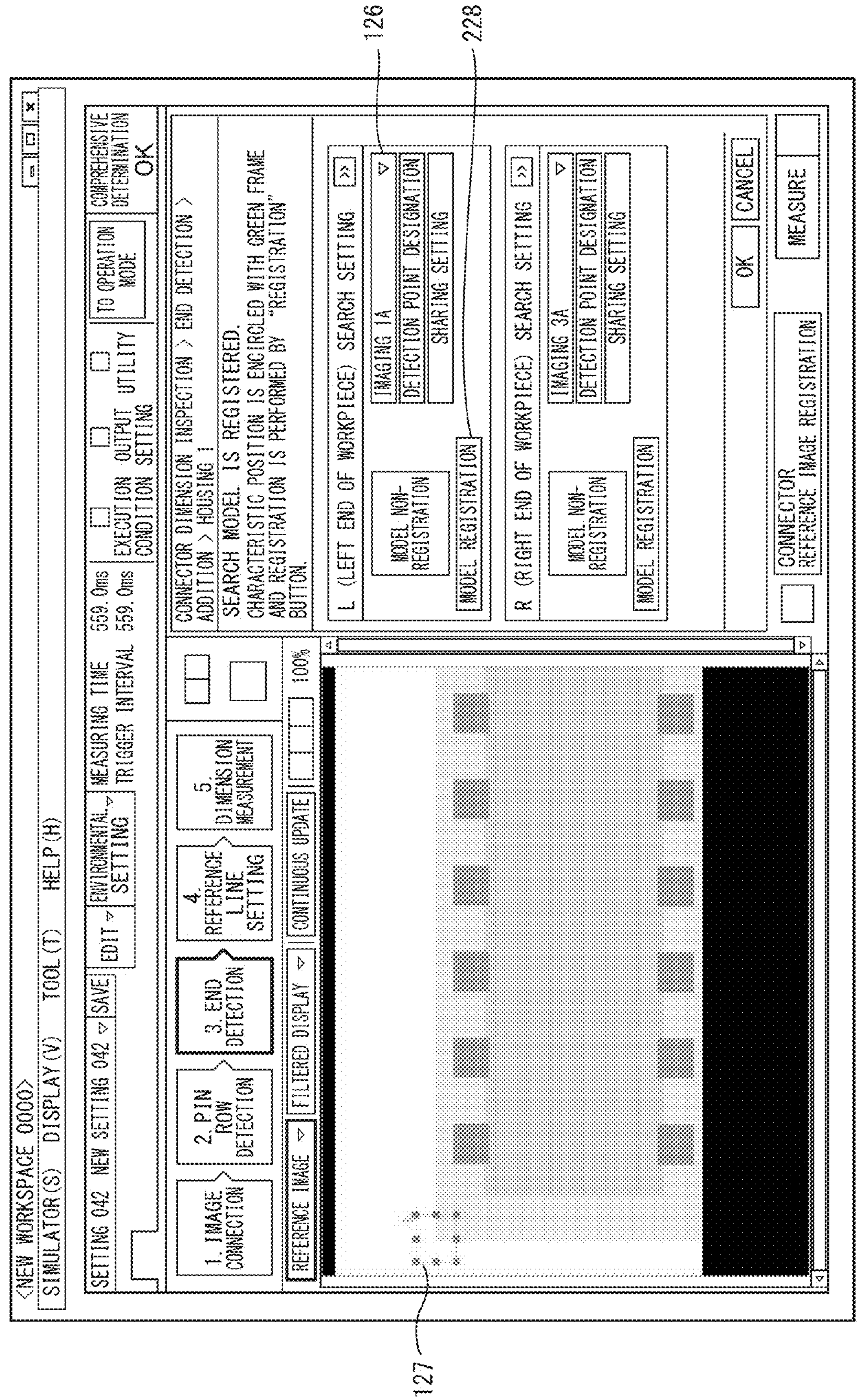
FIG. 28 is a diagram illustrating a registration screen of a search model for end detection.

FIG. 28 is a diagram illustrating a registration screen of a search model for end detection. In order to set a left end of a workpiece, a front-light image (imaging 1A) of a left end of the connector is selected with the mouse 9 from an image selection section 126. The CPU 22 enlarges and displays the image of the left end and enables a search model to be easily registered. An inspection region 127 including the end is set through the operation of the mouse 9. Upon detecting that a model registration button 228 has been pressed, the CPU 22 stores a position of the inspection region 127 set at that time and a model image encircled with the inspection region 127 in the memory.

Figure 29:
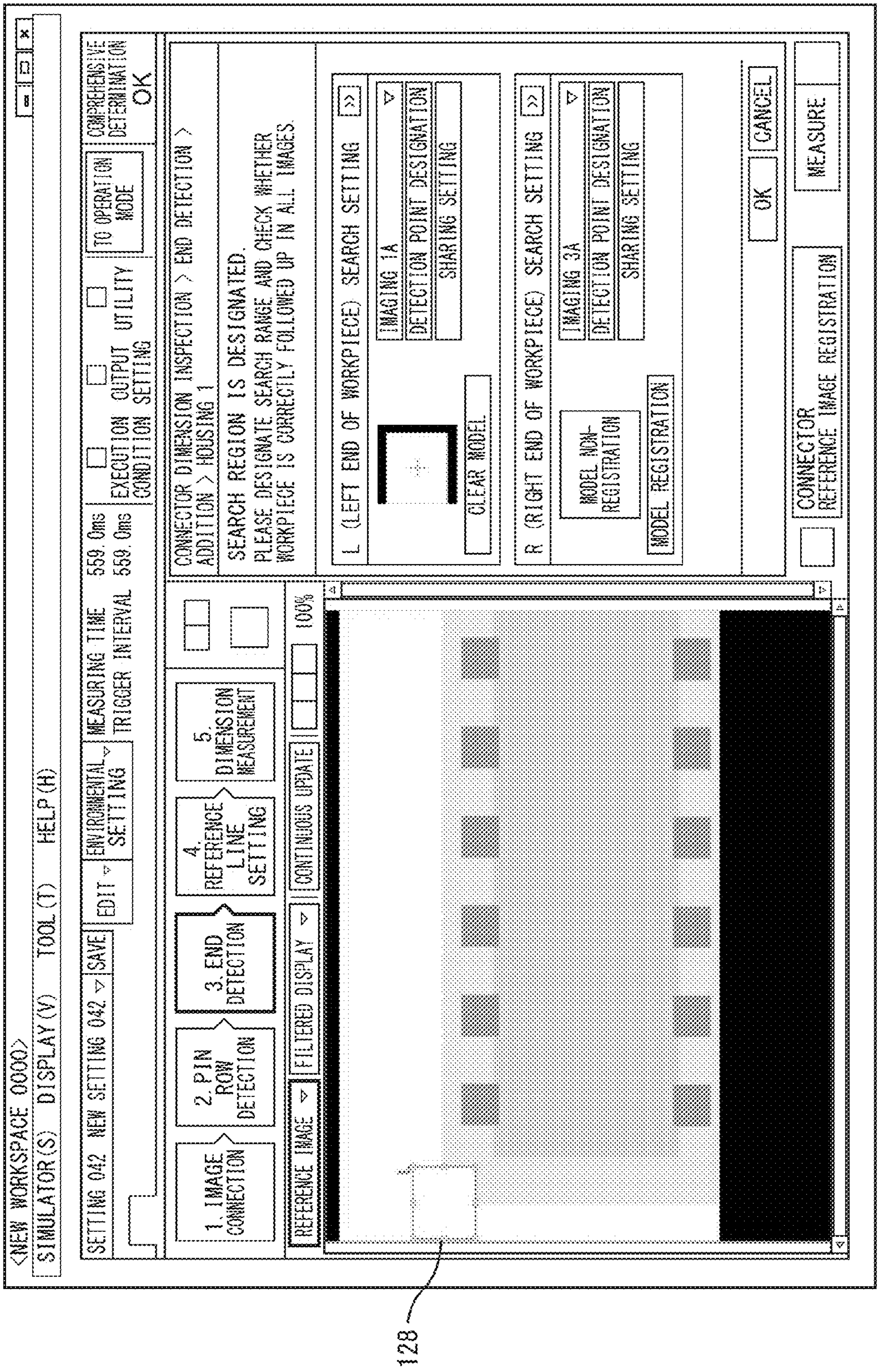
FIG. 29 is a diagram illustrating a setting screen of a search region.

FIG. 29 illustrates a setting screen of a search region 128. The CPU 22 sets a rectangular region set according to the operation of the mouse 9 as the search region 128 for the end detection. Here, the CPU 22 executes a search for the model image of the model-registered inspection region 127 within the search region 128, and determines whether the model image has been found. As illustrated in FIG. 29, the end detection fails when the contrast between the background and the housing is low.

In this embodiment, an end detection parameter is set using a back-light image.

Figure 30:
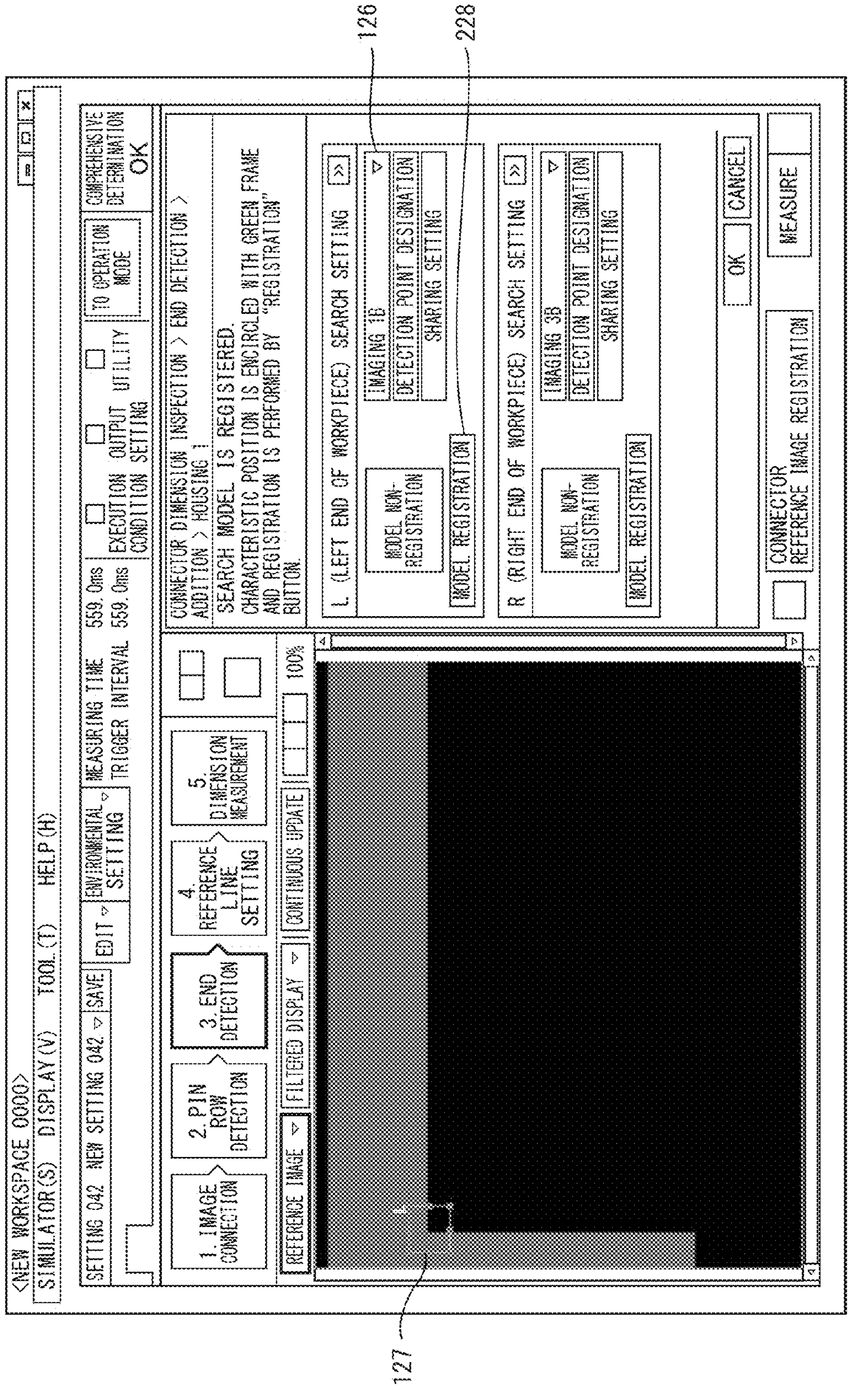
FIG. 30 is a diagram illustrating a registration screen of a search model for end detection.

FIG. 30 is a diagram illustrating a registration screen of a search model for end detection. A back-light image (imaging 1B) of a left end of the connector is selected with the mouse 9 from the image selection section 126. The CPU 22 enlarges and displays the back-light image of the left end and enables a search model to be easily registered. An inspection region 127 including the end is set through the operation of the mouse 9. Upon detecting that the model registration button 228 has been pressed, the CPU 22 stores a position of the inspection region 127 set at that time and a model image encircled with the inspection region 127 in the memory.

Figure 31:
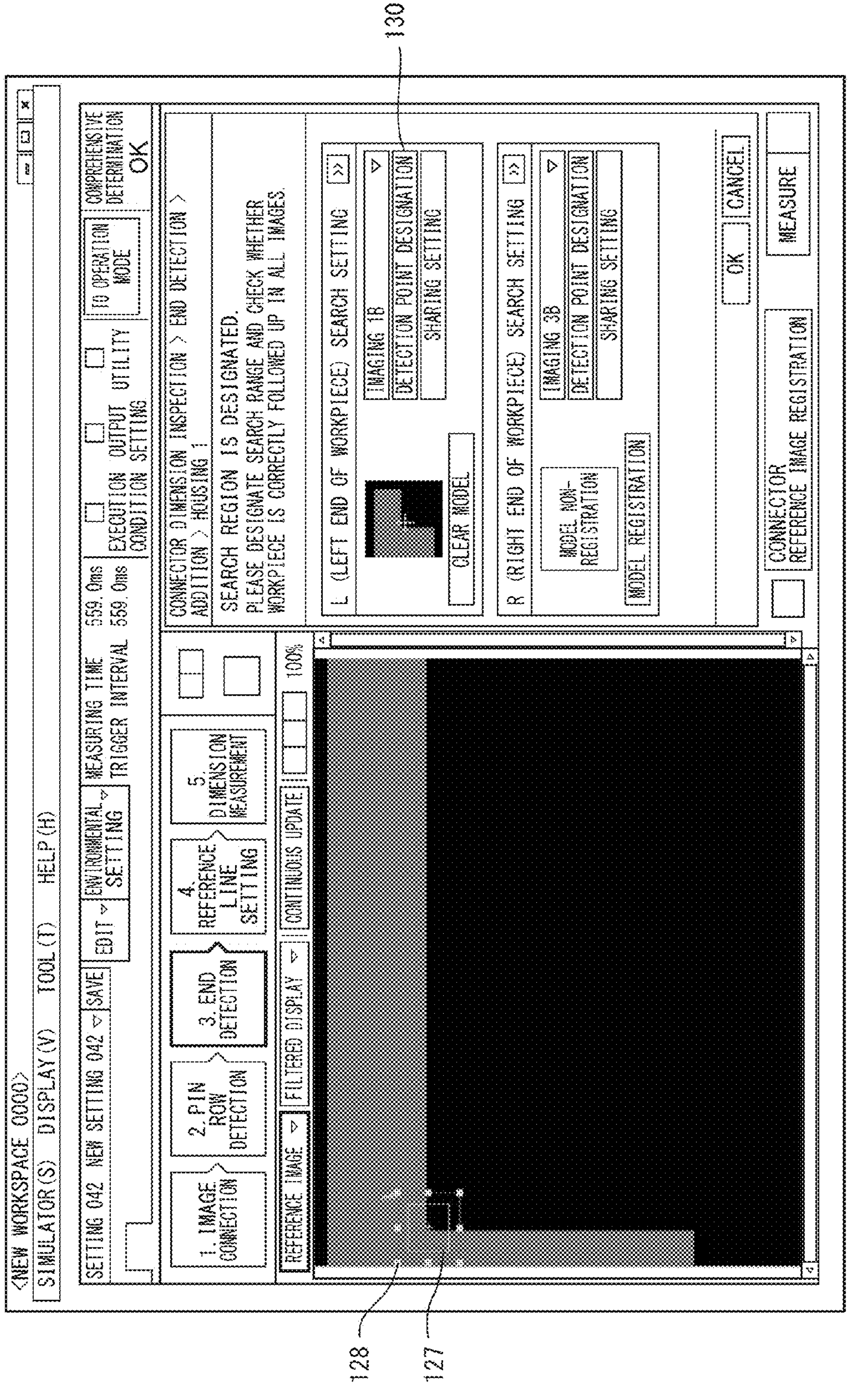
FIG. 31 is a diagram illustrating a setting screen of a search region.

FIG. 31 illustrates a setting screen of the search region 128. The CPU 22 sets a rectangular region set according to the operation of the mouse 9 as the search region 128 for the end detection. Here, the CPU 22 executes a search for the model image of the model-registered inspection region 127 within the search region 128, and determines whether the model image is found. As illustrated in FIG. 31, the end detection succeeds when the contrast between the background and the housing is high. When a reference point designation button 130 for designating the reference point is clicked with the mouse 9, the CPU 22 causes a designation screen of the reference point to be displayed on the monitor 10.

Figure 32:
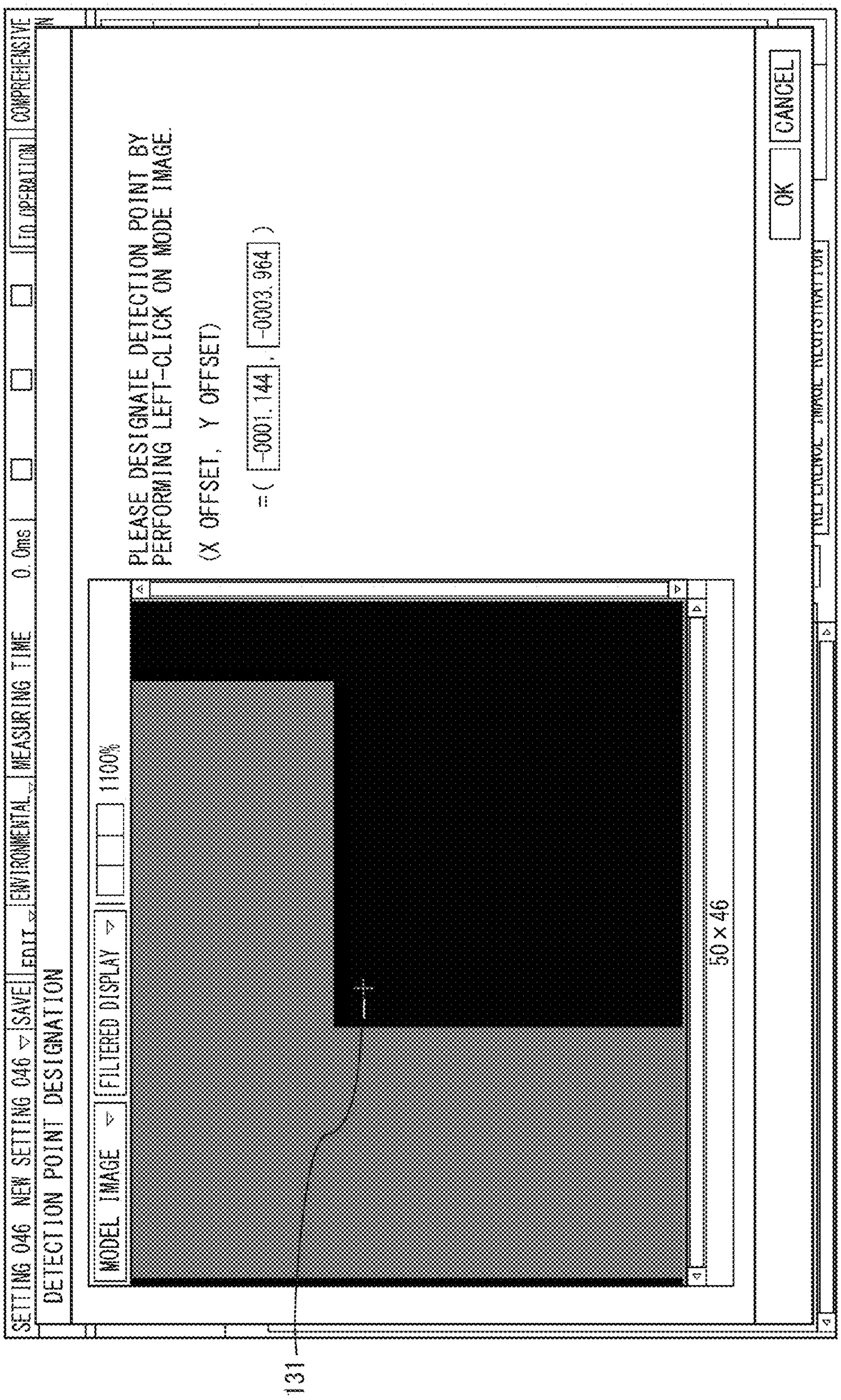
FIG. 32 is a diagram illustrating a designation screen of a reference point.
Figure 33:
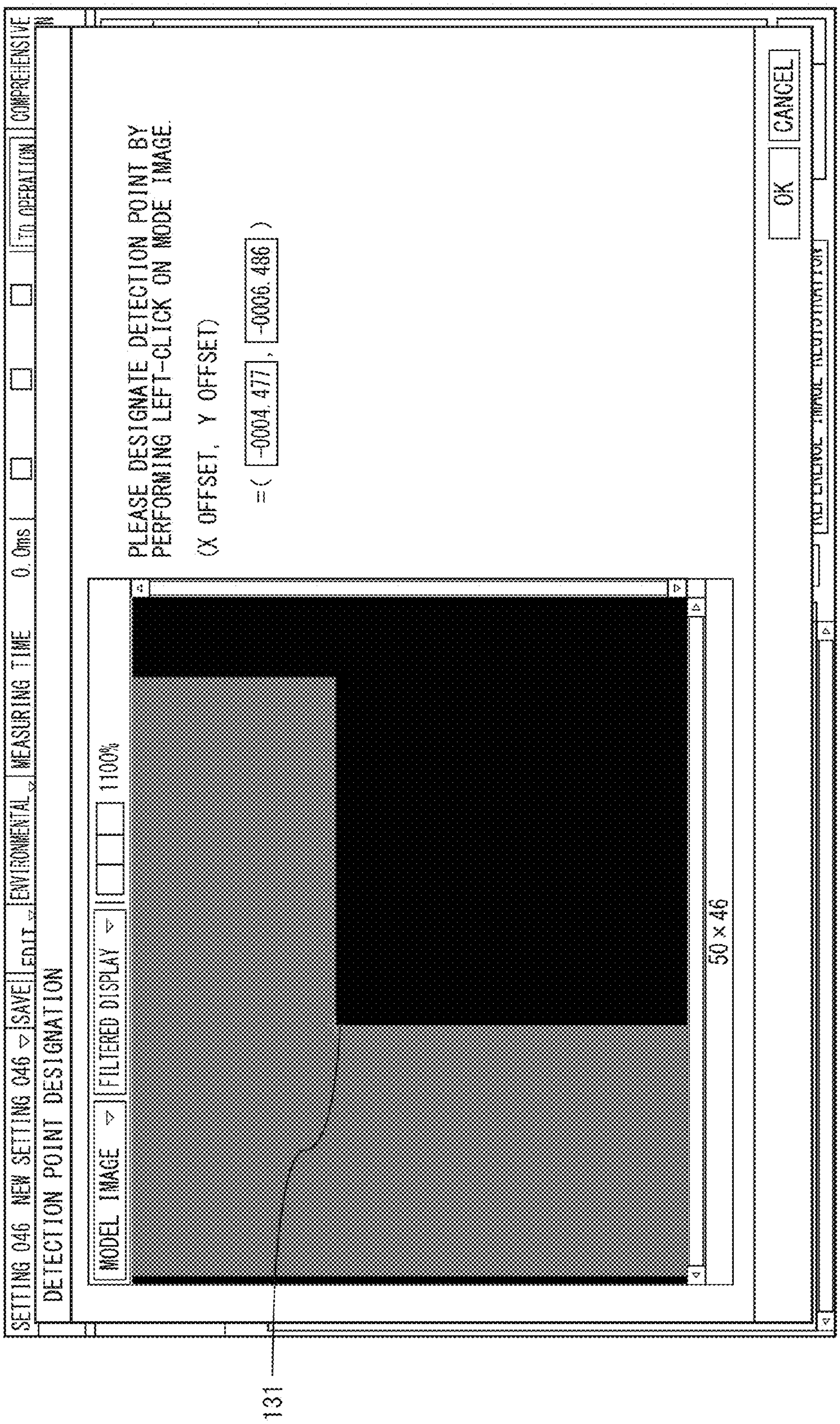
FIG. 33 is a diagram illustrating the designation screen of the reference point.

FIGS. 32 and 33 are diagrams each illustrating a designation screen of a reference point 131. Particularly, FIG. 32 illustrates the reference point 131 before fine adjustment, and FIG. 33 illustrates the reference point 131 after the fine adjustment. The CPU 22 arranges the reference point 131 in the middle of the inspection region 127. The user performs fine adjustment on the reference point 131 by operating the mouse 9, and the CPU 22 stores a position of the reference point 131 after the fine adjustment in the memory.

For a right end of a workpiece which is an end of a right side of the connector, the inspection region 127, the search region 128, and the reference point 131 are set in a procedure similar to that for a left end of the workpiece.

Figure 34:
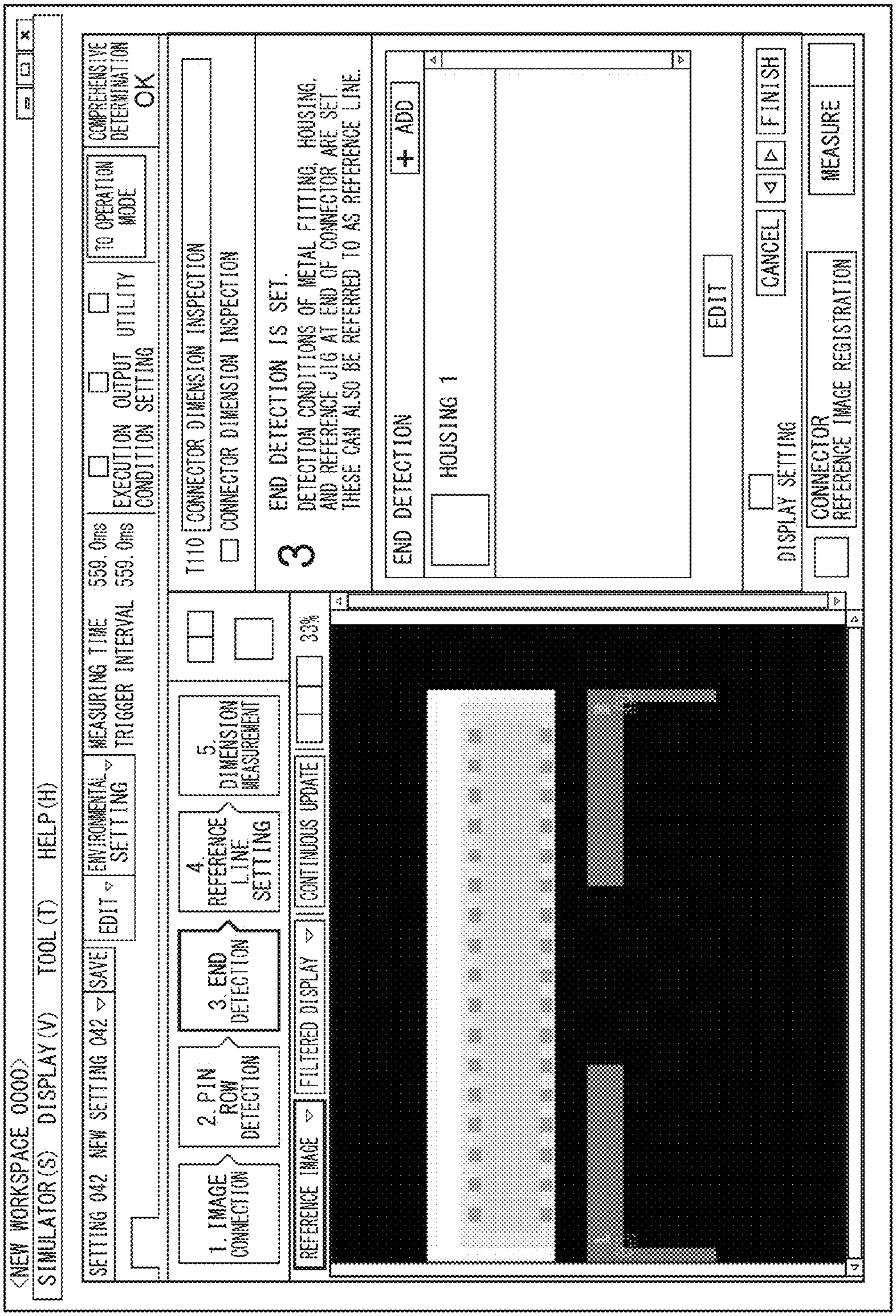
FIG. 34 is a diagram illustrating a screen indicating that left and right ends of a workpiece have been set normally.

FIG. 34 is a screen indicating that the left and right ends of the workpiece have been set normally. In this example, it is shown that the left and right ends of the workpiece are set using the back-light image.

Setting of Reference Line

Figure 35:
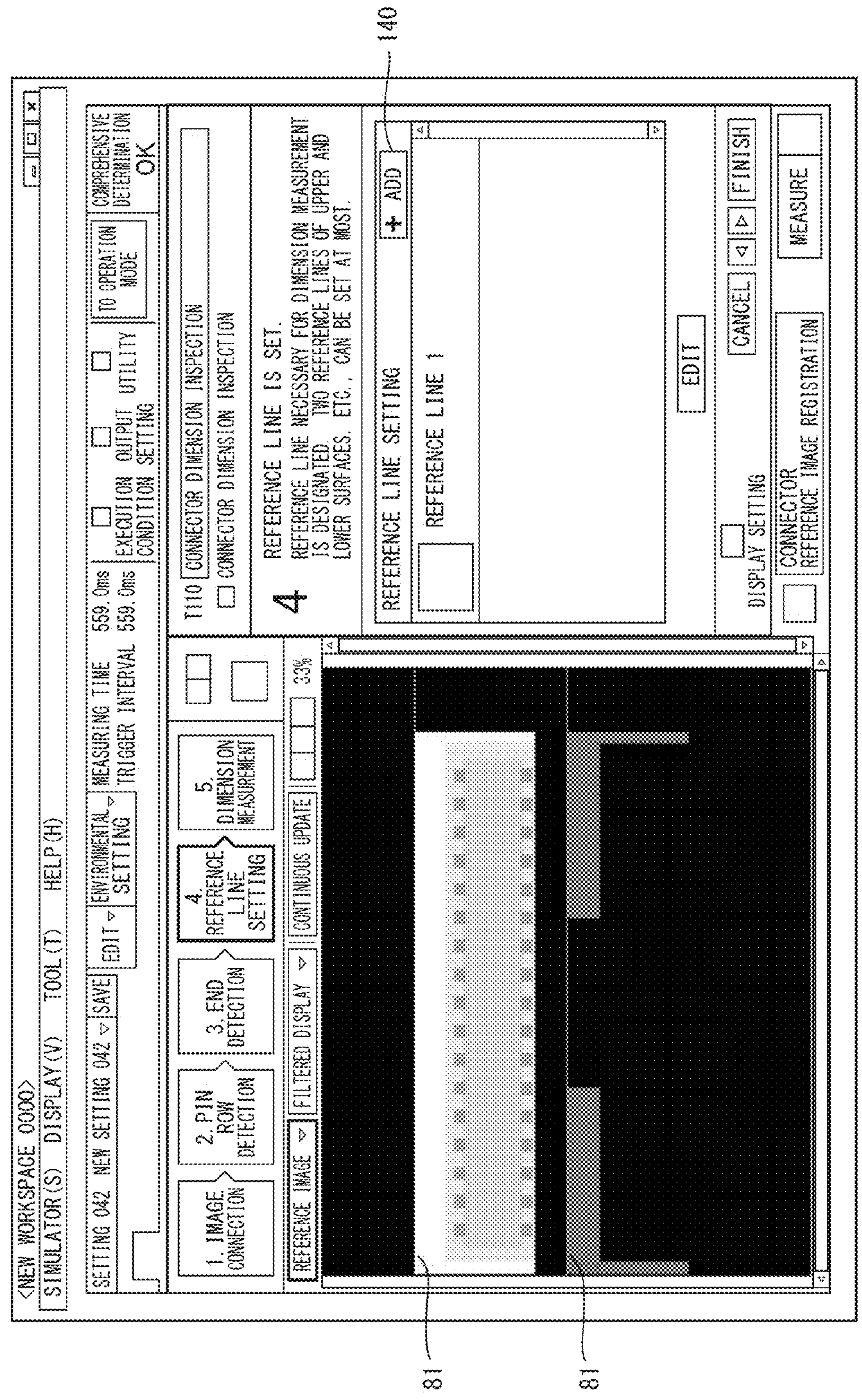
FIG. 35 is a diagram illustrating a setting screen on which a reference line is set.

FIG. 35 illustrates a setting screen on which a reference line 81 is set. When an addition button (edit button) 140 is clicked, the screen transitions to a detailed setting screen on which each parameter of the reference line 81 is set.

Figure 36:
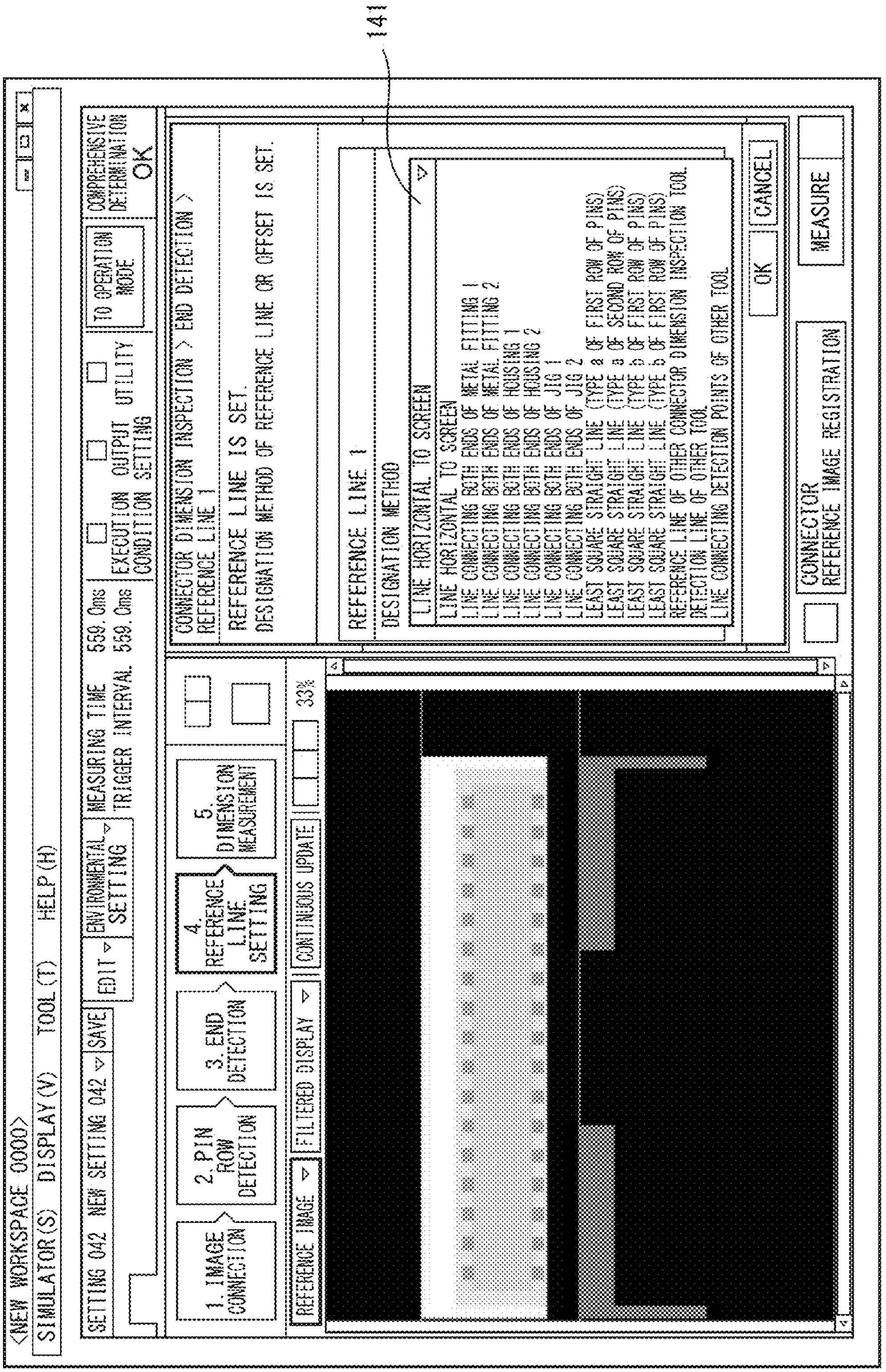
FIG. 36 is a diagram illustrating a selection item of a designation method of the reference line.

FIG. 36 illustrates a selection item 141 of a designation method of the reference line 81. Here, a line for the connector that is the inspection object 8 to be designated as the reference line 81 is designated with the mouse 9.

Figure 37:
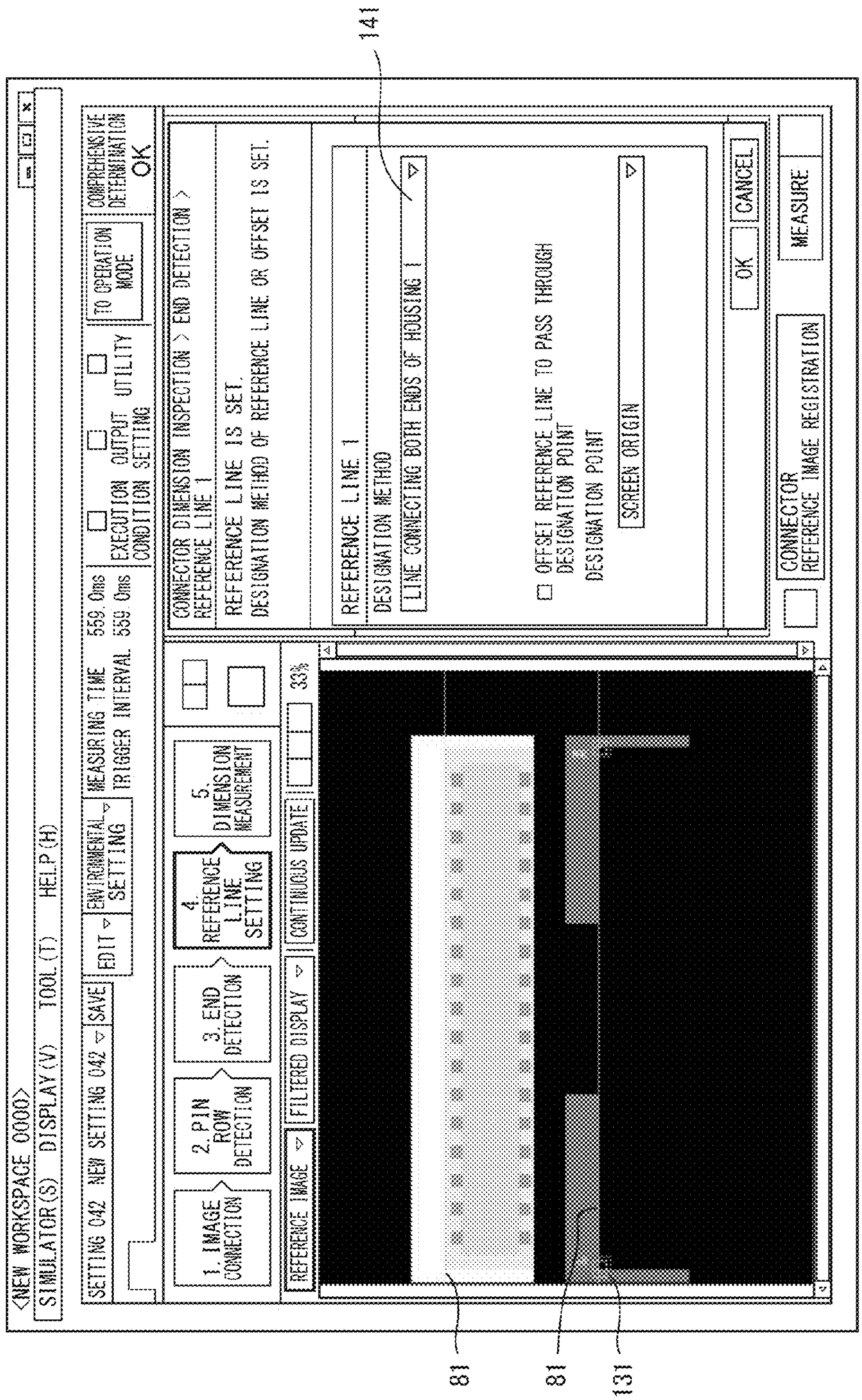
FIG. 37 is a diagram illustrating a screen when an item "line connecting both ends of housing" has been designated as the reference line from the selection item.

FIG. 37 is a diagram illustrating a screen when an item “line connecting both ends of housing” has been designated as the reference line 81 from the selection item 141. As described above, both ends (the left and right ends of the workpiece) of the housing are preset using the back-light image. Accordingly, when the item “line connecting both ends of housing” is designated as the reference line 81, the CPU 22 sets the reference line 81 to pass through the left and right ends of the workpiece. The left end of the workpiece corresponds to the reference point 131. Although not illustrated, the right end of the workpiece is also set by the reference point.

Setting of Dimension Measurement Parameter

Here, among dimensions of the connector, a dimension of which portion of the connector is to be measured is set.

Figure 38:
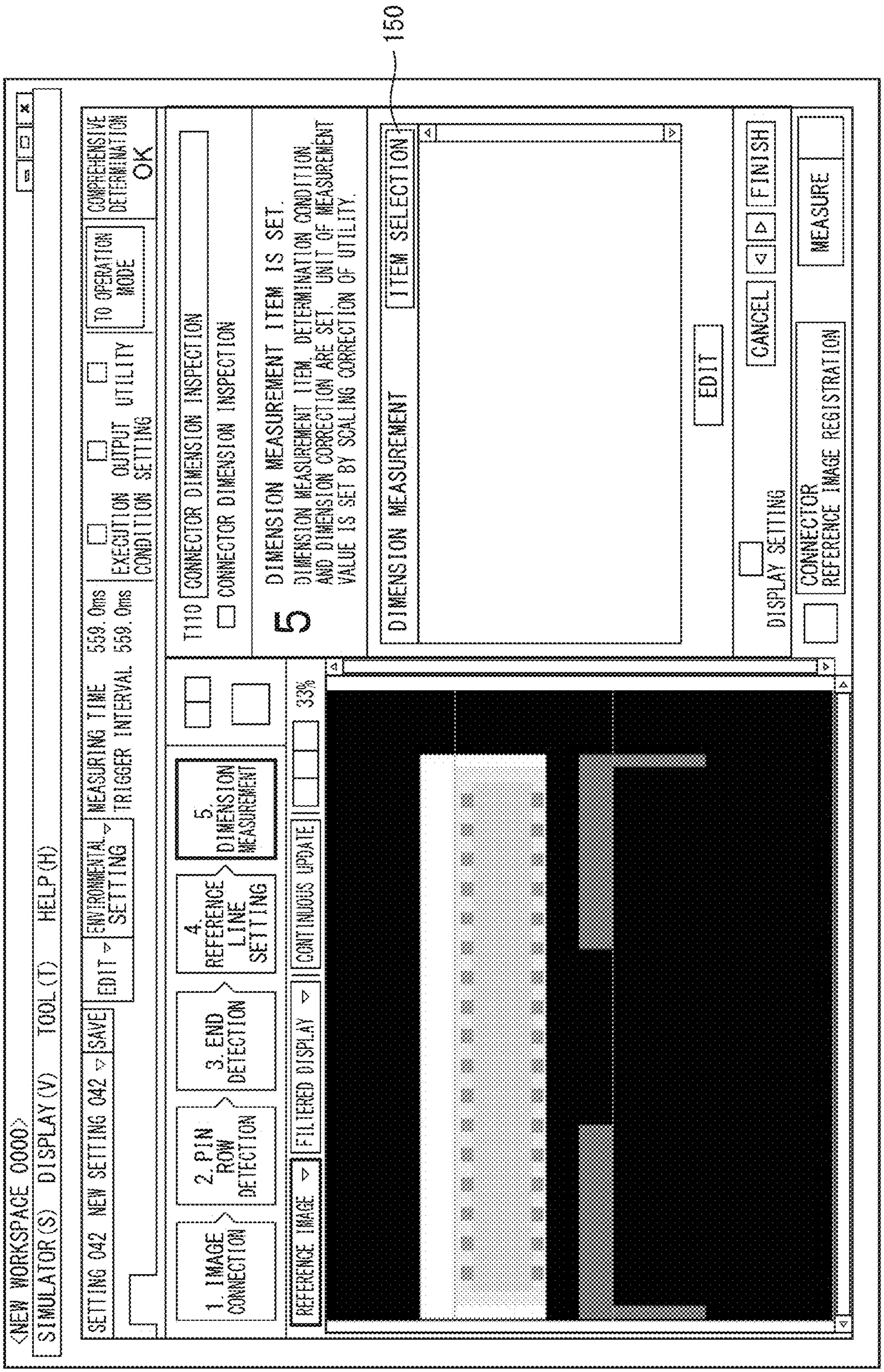
FIG. 38 is a diagram illustrating a main screen on which a dimension measurement parameter is set.

FIG. 38 is a diagram illustrating a main screen on which a dimension measurement parameter is set. The user can select a dimension to be measured by clicking an item selection button 150 using the mouse 9.

Figure 39:
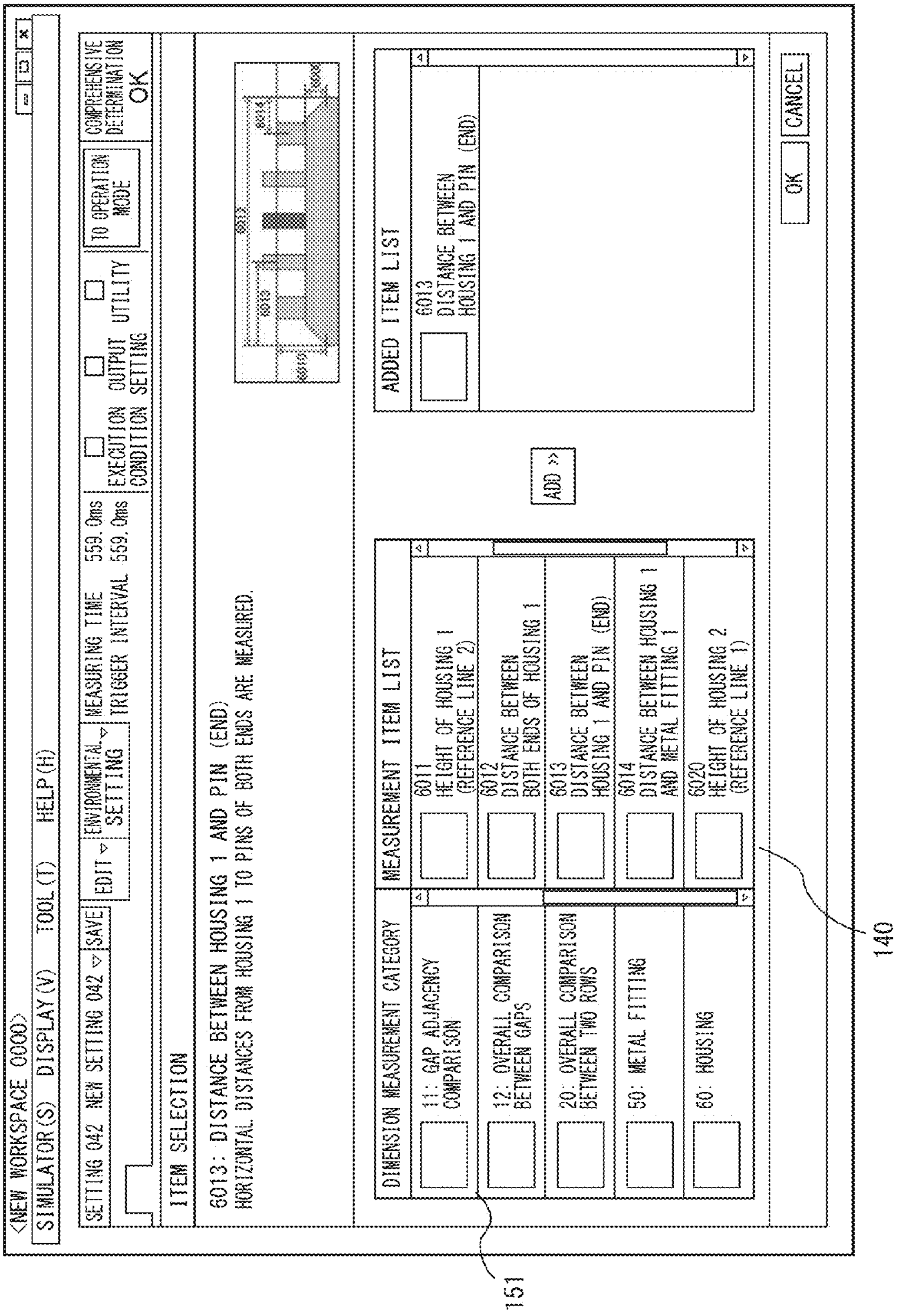
FIG. 39 is a diagram illustrating an item selection screen for setting a dimension measurement parameter.

FIG. 39 is a diagram illustrating an item selection screen for setting a dimension measurement parameter. Here, a dimension measurement category 151 indicating a portion of the connector to be measured according to categories and a measurement item list 152 showing one or more measurement items corresponding to a selected dimension measurement category are displayed. The CPU 22 switches the measurement item list 152 according to the category selected with the mouse 9. In the example illustrated in FIG. 39, various measurement items related to the housing are displayed if the housing is selected from the dimension measurement category 151. A housing height is a height of the housing having the reference line as an initial point. A housing distance is a distance from a left end to a right end of the housing. A distance between the housing and the pin (end) is a distance from an end of the housing to an end pin. A distance between the housing and the metal fitting is a distance from the housing to the metal fitting, for example, a distance from the end of the housing to the center of the metal fitting. A measurement item selected with the mouse 9 from the measurement item list 152 is added as an item to be actually measured.

Figure 40:
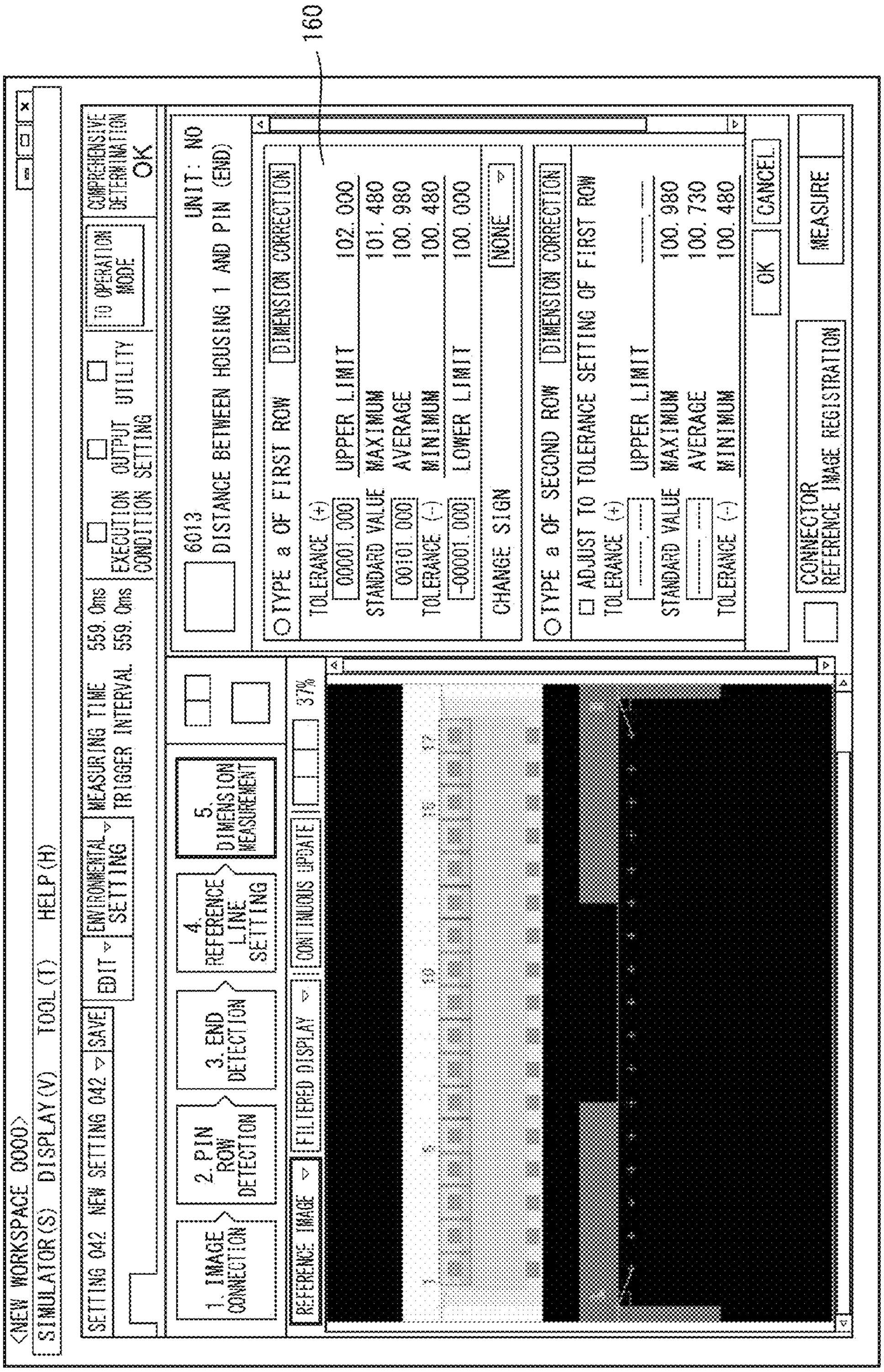
FIG. 40 is a diagram illustrating a screen on which a parameter for use in a quality determination on a selected measurement item is set.

FIG. 40 illustrates a screen on which a parameter for use in a quality determination on a selected measurement item is set. In a parameter setting section 160, a standard value and a positive/negative tolerance on design in a distance between the housing and the pin (end) for the pins of the first row are input through the mouse 9. The CPU 22 may calculate an upper limit and a lower limit of a dimension from the standard value and the tolerance to indicate the calculated upper and lower limits in the parameter setting section 160. In addition, the CPU 22 may actually measure the dimension from the workpiece image using the image processing section 30 to obtain and display an average value between a measurement value for the 1st pin and a measurement value for the 17th pin or display a minimum value and a maximum value.

Figure 41:
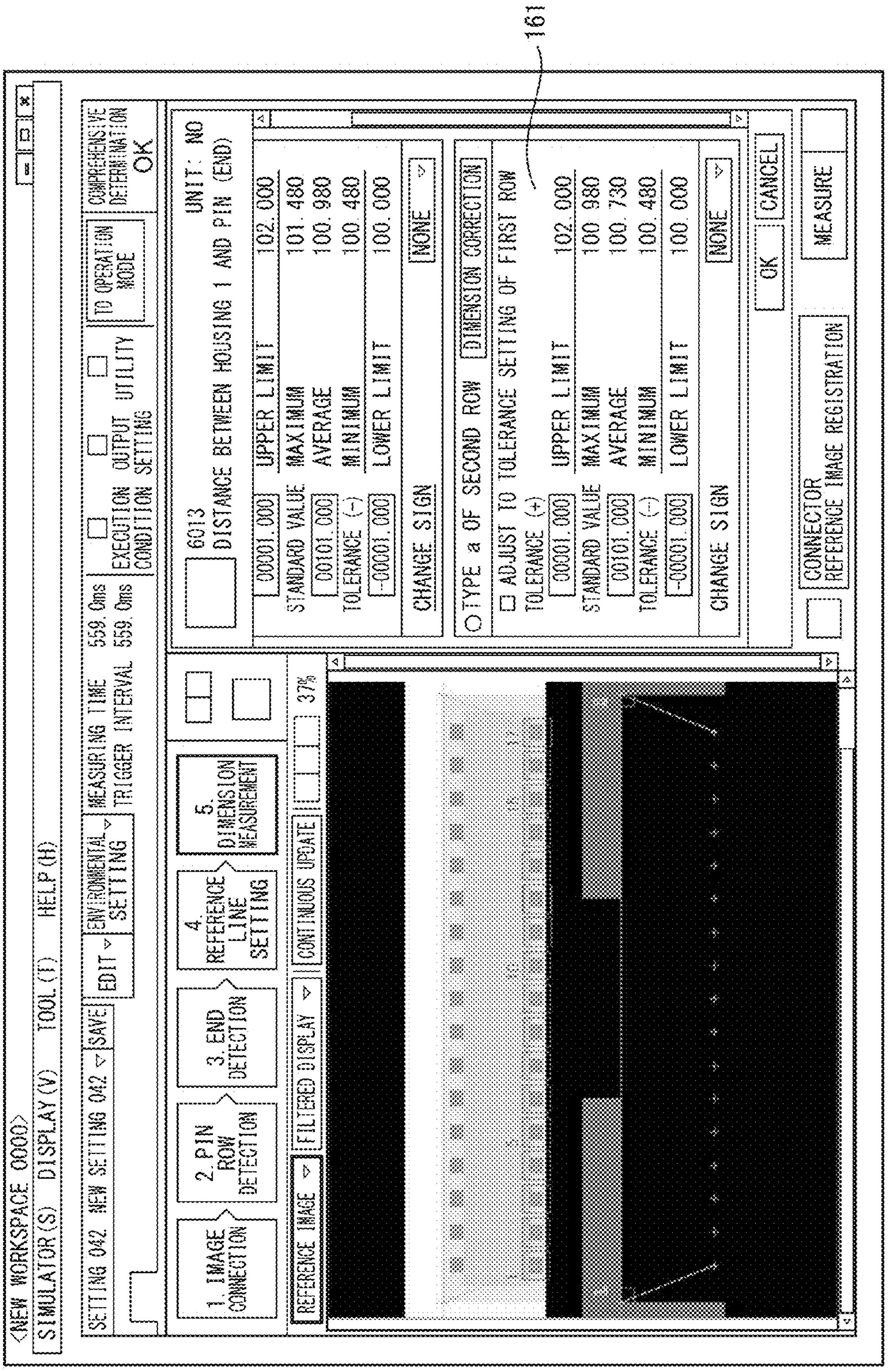
FIG. 41 is a diagram illustrating a screen on which a parameter for use in a quality determination on a selected measurement item is set.

FIG. 41 illustrates a screen on which a parameter for use in a quality determination on a selected measurement item is set. In a parameter setting section 161, a standard value and a positive/negative tolerance on design in a distance between the housing and the pin (end) for the pins of the second row are input through the mouse 9. The CPU 22 may calculate an upper limit and a lower limit of a dimension from the standard value and the tolerance to indicate the calculated upper and lower limits in the parameter setting section 161. In addition, the CPU 22 may actually measure the dimension from the workpiece image using the image processing section 30 to obtain and display an average value between a measurement value for the 1st pin and a measurement value for the 17th pin or display a minimum value and a maximum value.

Figure 42:
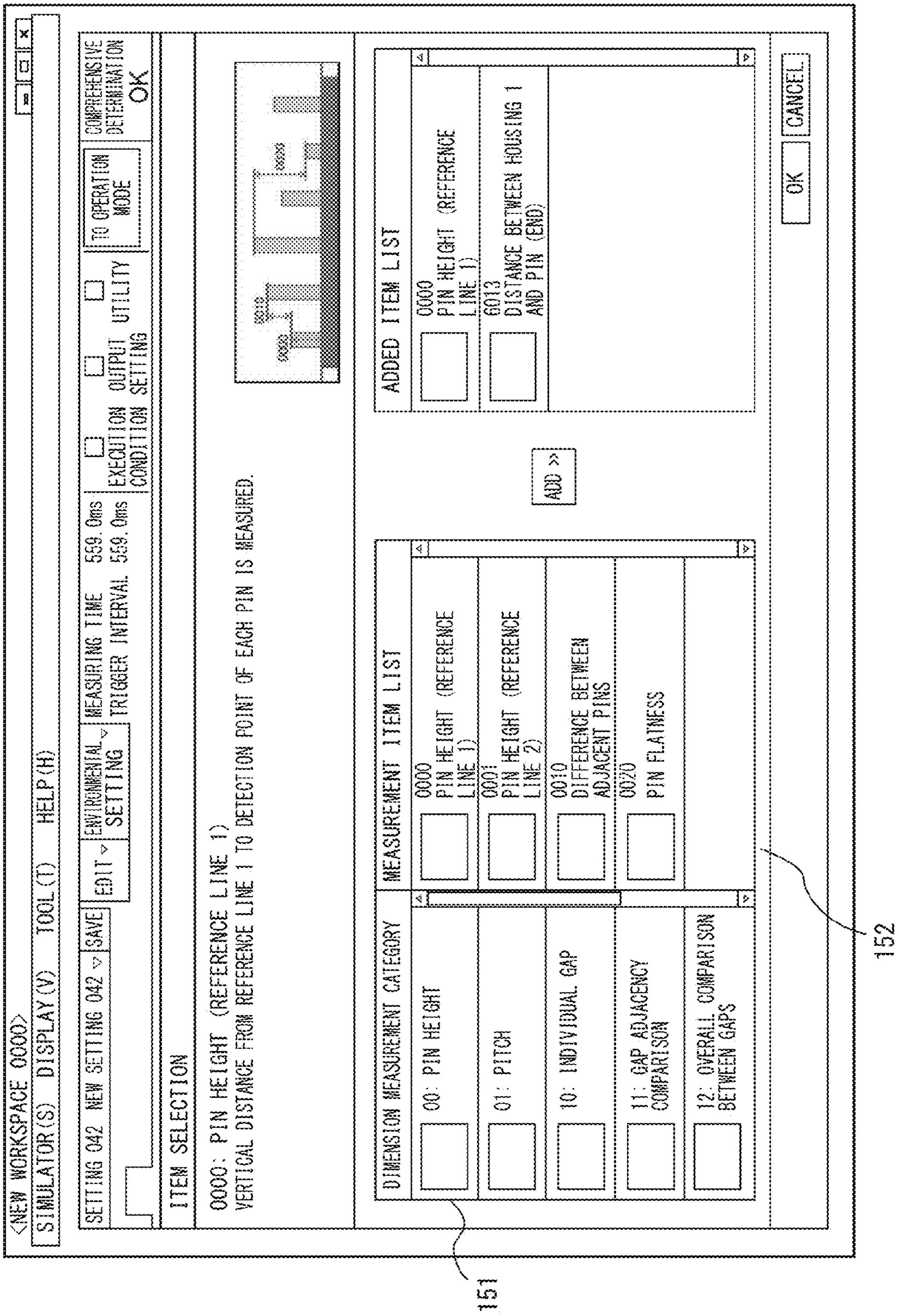
FIG. 42 is a diagram illustrating an item selection screen for setting a dimension measurement parameter.

FIG. 42 is a diagram illustrating an item selection screen for setting a dimension measurement parameter. Here, because the pin height is selected from the dimension measurement category 151, a measurement item related to the pin height is displayed on the measurement item list 152. The user clicks and selects the measurement item through the mouse 9. Here, the pin height from the reference line is assumed to be selected.

Figure 43:
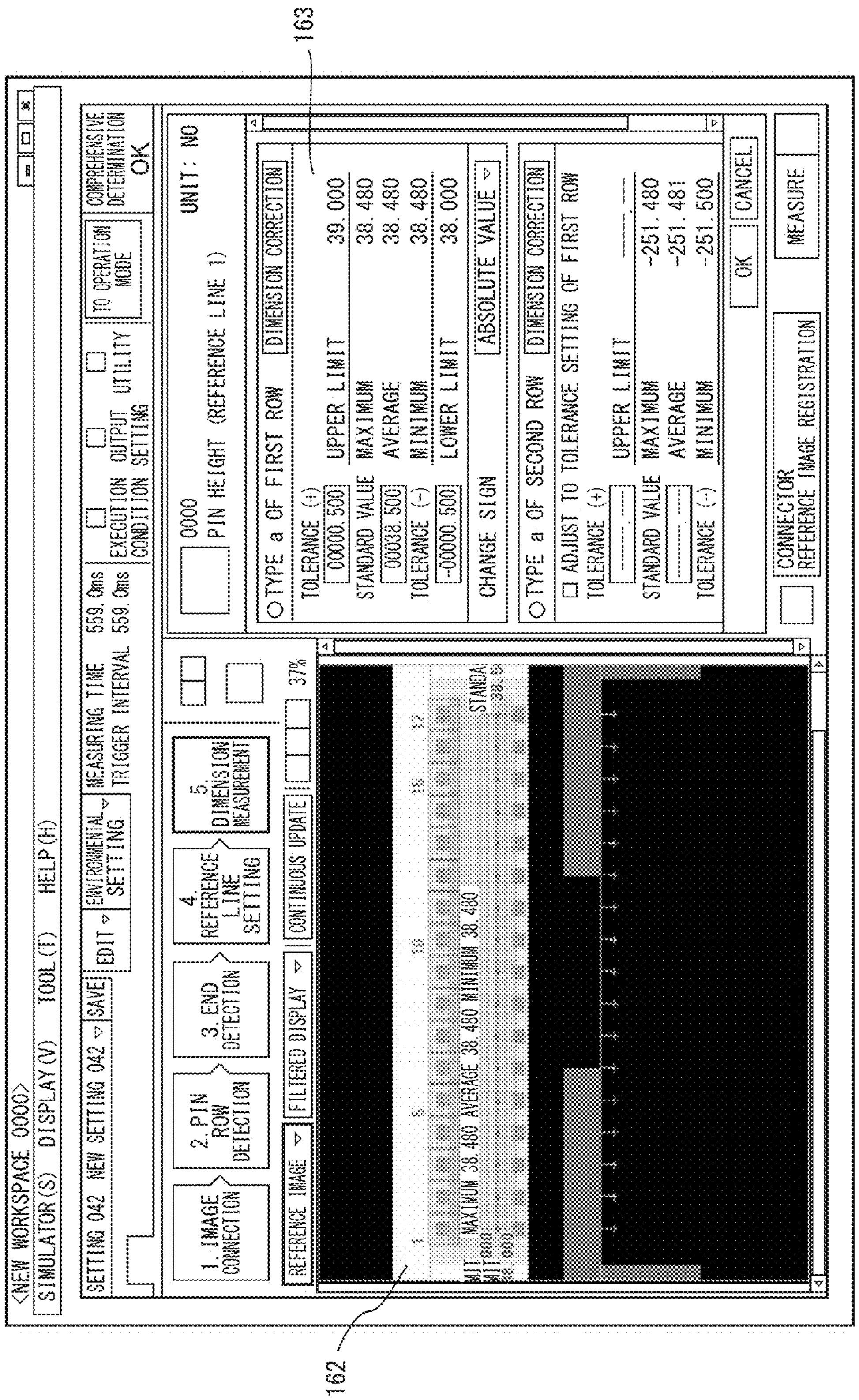
FIG. 43 is a diagram illustrating a screen on which a parameter for use in a quality determination on a selected measurement item is set.

FIG. 43 illustrates a screen on which a parameter for use in a quality determination on a selected measurement item is set. In order to easily know the measurement item, a reference line, a reference point, a pin number, a mark indicating a portion to be measured, and the like are displayed along with the workpiece image on an image display section 162. Here, as the workpiece image, both the front-light image and the back-light image are displayed. In a parameter setting section 163, a standard value and a positive/negative tolerance on design in the pin height for the pins of the first row are input through the mouse 9. The CPU 22 may calculate an upper limit and a lower limit of a dimension from the standard value and the tolerance to indicate the calculated upper and lower limits in the parameter setting section 163. In addition, the CPU 22 may actually measure the dimension from the workpiece image using the image processing section 30, to obtain and display an average value of measurement values for 1st to 17th pins or display a minimum value and a maximum value. It may be easily recognized whether a workpiece (product) used to capture a workpiece image is appropriate from these numerical values.

Figure 44:
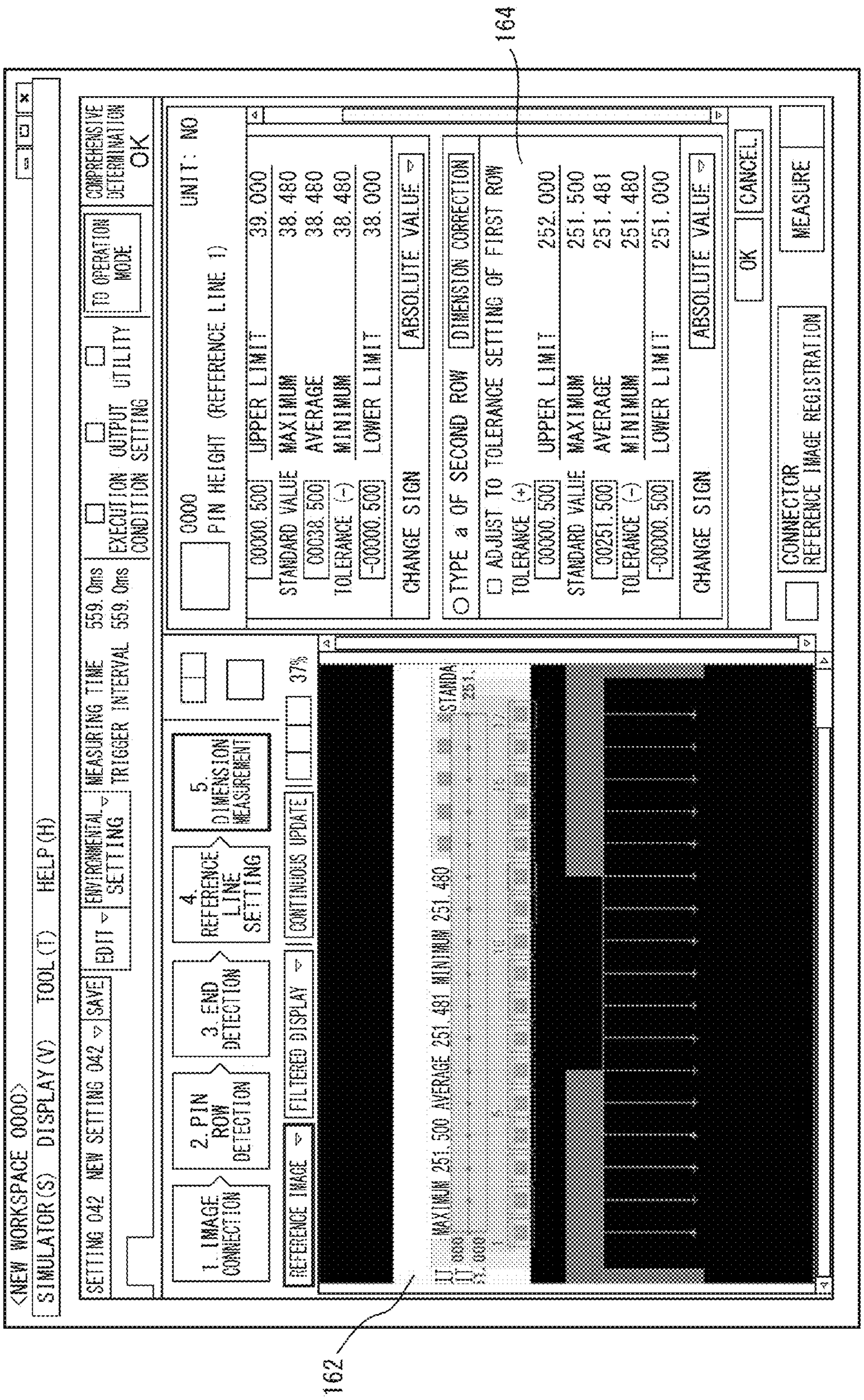
FIG. 44 is a diagram illustrating a screen on which a parameter for use in a quality determination on a selected measurement item is set.

FIG. 44 illustrates a screen on which a parameter for use in a quality determination on a selected measurement item is set. In a parameter setting section 164, a parameter for a pin height for pins of the second row is input. The CPU 22 may calculate an upper limit and a lower limit a dimension from a standard value and a tolerance input in the parameter setting section 164 to indicate the calculated upper and lower limits in the parameter setting section 164. In addition, the CPU 22 may actually measure a dimension from a workpiece image using the image processing section 30 to obtain and display an average value of measurement values for each of pins from the 1st pin to the 17th pin of the second row or display a minimum value and a maximum value.

<Modified Example of Image Connection>

In the above-described embodiment, the description has been given that an imaging operation is performed so that one or more common pins are included between adjacent images and two adjacent images are connected so that the common pins are superimposed, and thus the full image of the inspection object 8 is created by the CPU 22 or the image processing section 30. However, it is not necessary for a portion to be commonly included in adjacent images to be part of the inspection object 8. That is, a mark serving as a connection reference may be provided to a member which moves along with the inspection object 8, such as a jig or a belt conveyor.

Figure 45:
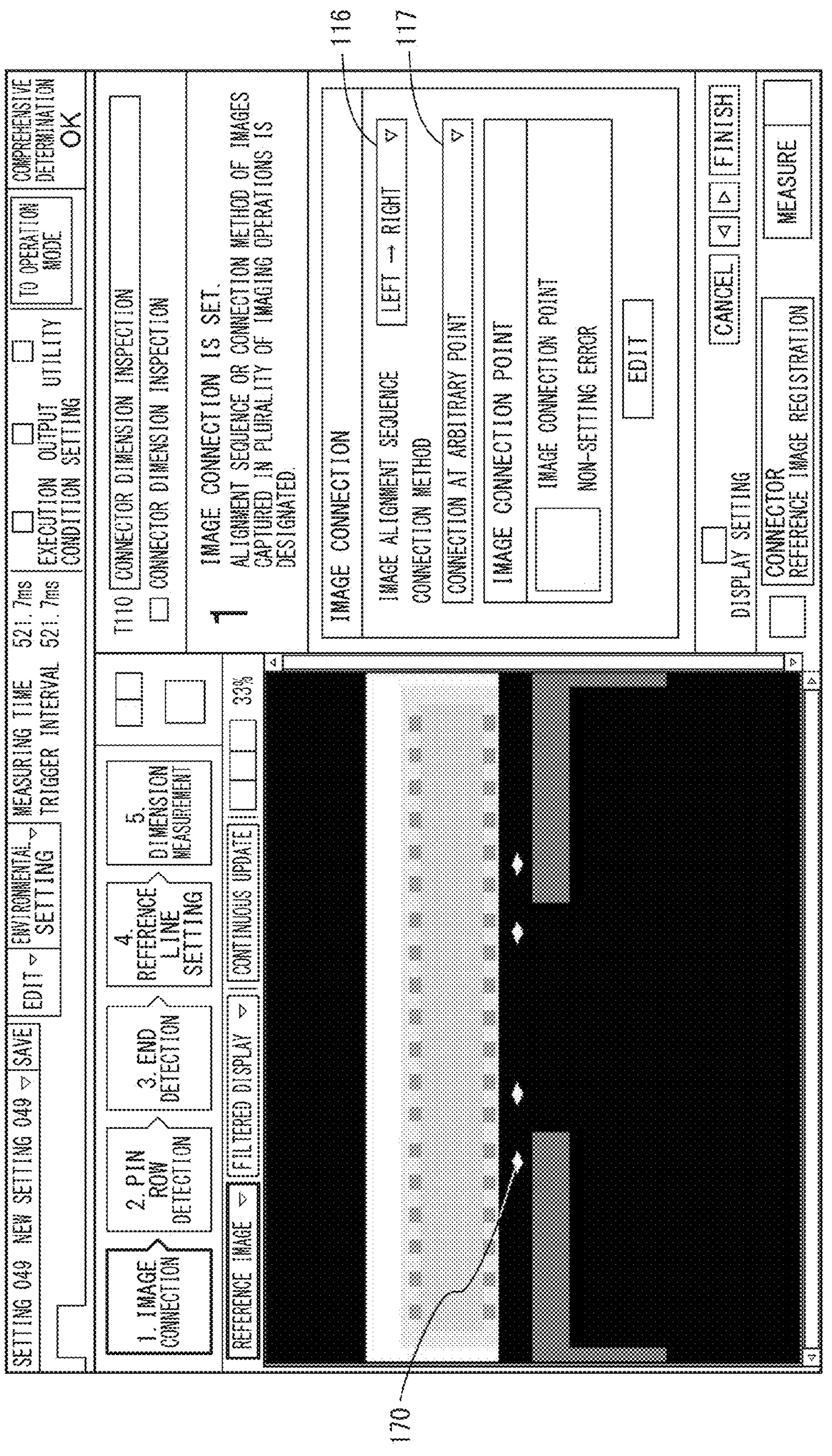
FIG. 45 is a diagram illustrating an example of a mark serving as a reference for connecting a plurality of images.

FIG. 45 is a diagram illustrating an example of a mark serving as a reference for connecting a plurality of images. In this example, a connection mark 170 is provided in a jig which conveys the inspection object 8. If an item "connection at arbitrary point" is selected as a connection method 117, the CPU 22 can make a connection based on the mark 170.

Figure 46:
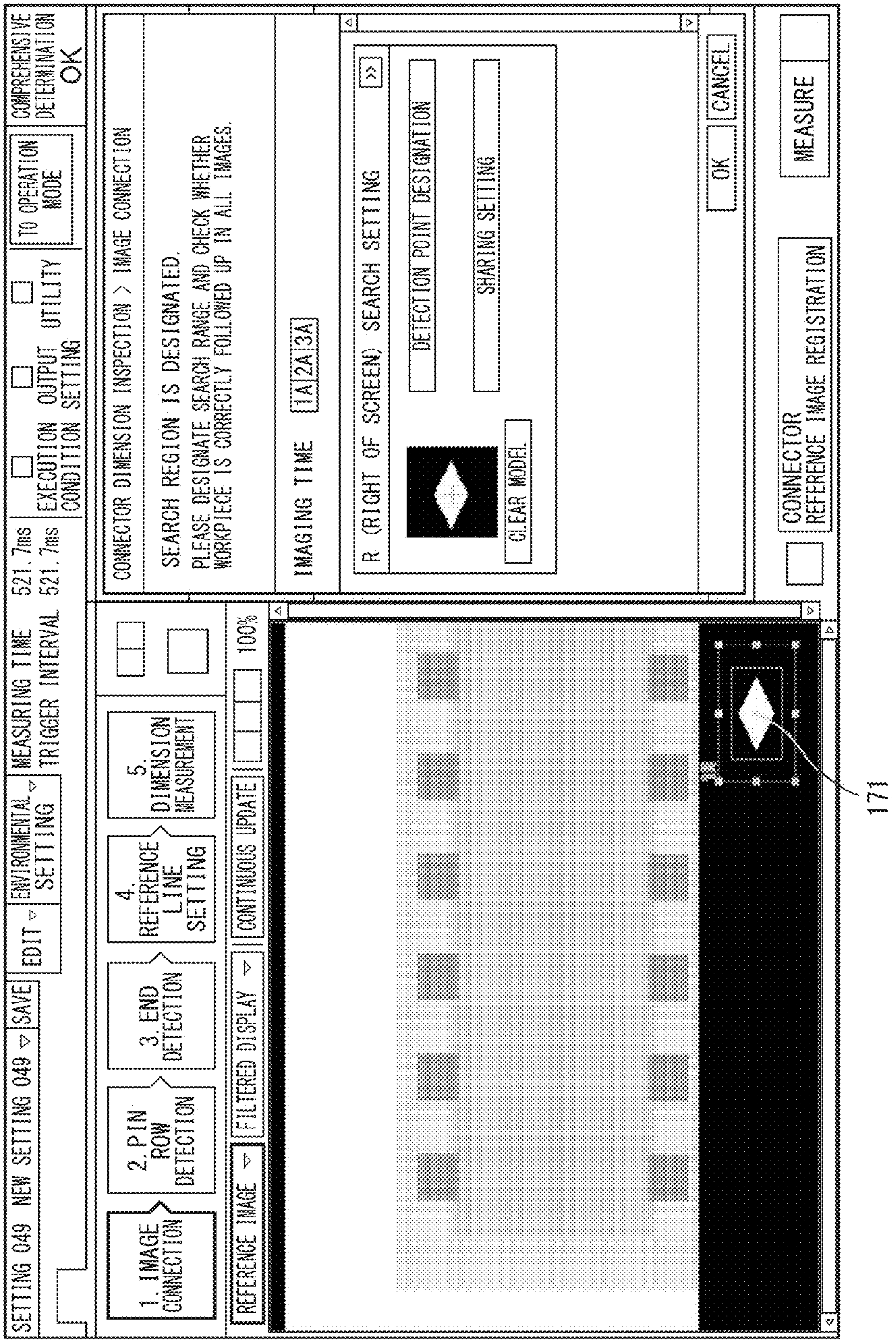
FIG. 46 is a diagram illustrating a setting screen on which a mark serving as a reference of an image connection is set.

FIG. 46 is a diagram illustrating a setting screen on which the mark 170 serving as a reference of an image connection is set. The CPU 22 enables a reference point 171, the inspection region, and the search region to be easily set by enlarging and displaying a left-end image end of the connector. The user sets the reference point 171 at the center of the mark 170 by operating the mouse 9. Further, the CPU 22 sets the inspection region and the search region based on the reference point 171. According to the operation of the mouse 9, the CPU 22 may finely adjust the reference point 171 or adjust positions and sizes of the inspection region and the search region.

Figure 47:
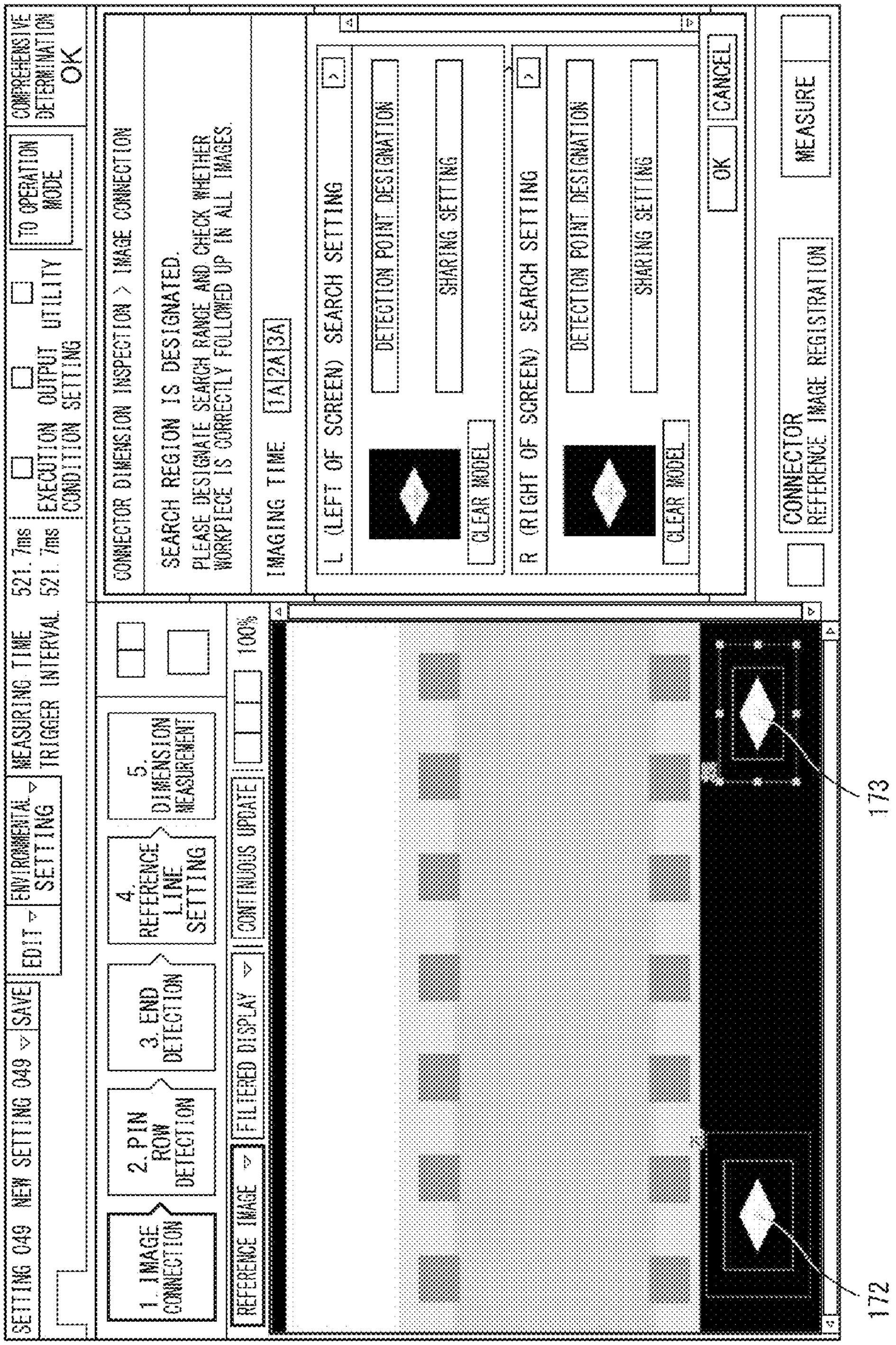
FIG. 47 is a diagram illustrating a setting screen on which a mark serving as a reference of an image connection is set.

FIG. 47 is a diagram illustrating a setting screen on which a mark 170 serving as a reference of an image connection is set. By enlarging and displaying an image of a middle portion of the connector, the CPU 22 enables a reference point 172 serving as a reference for connecting a left-end image and an image of a middle portion, an inspection region and a search region based on the reference point 172, a reference point 173 serving as a reference for connecting the image of the middle portion and the right-end image, and an inspection region and a search region based on the reference point 173 to be easily set. By operating the mouse 9, the user sets the reference point 172 at the center of the mark 170 of the left side, and sets the reference point 173 at the center of the mark 170 of the right side. Further, the CPU 22 sets the inspection regions and the search regions based on the reference points 172 and 173. The CPU 22 may finely adjust the reference points 172 and 173 or adjust the positions and the sizes of the inspection regions and the search regions according to the operation of the mouse 9.

Figure 48:
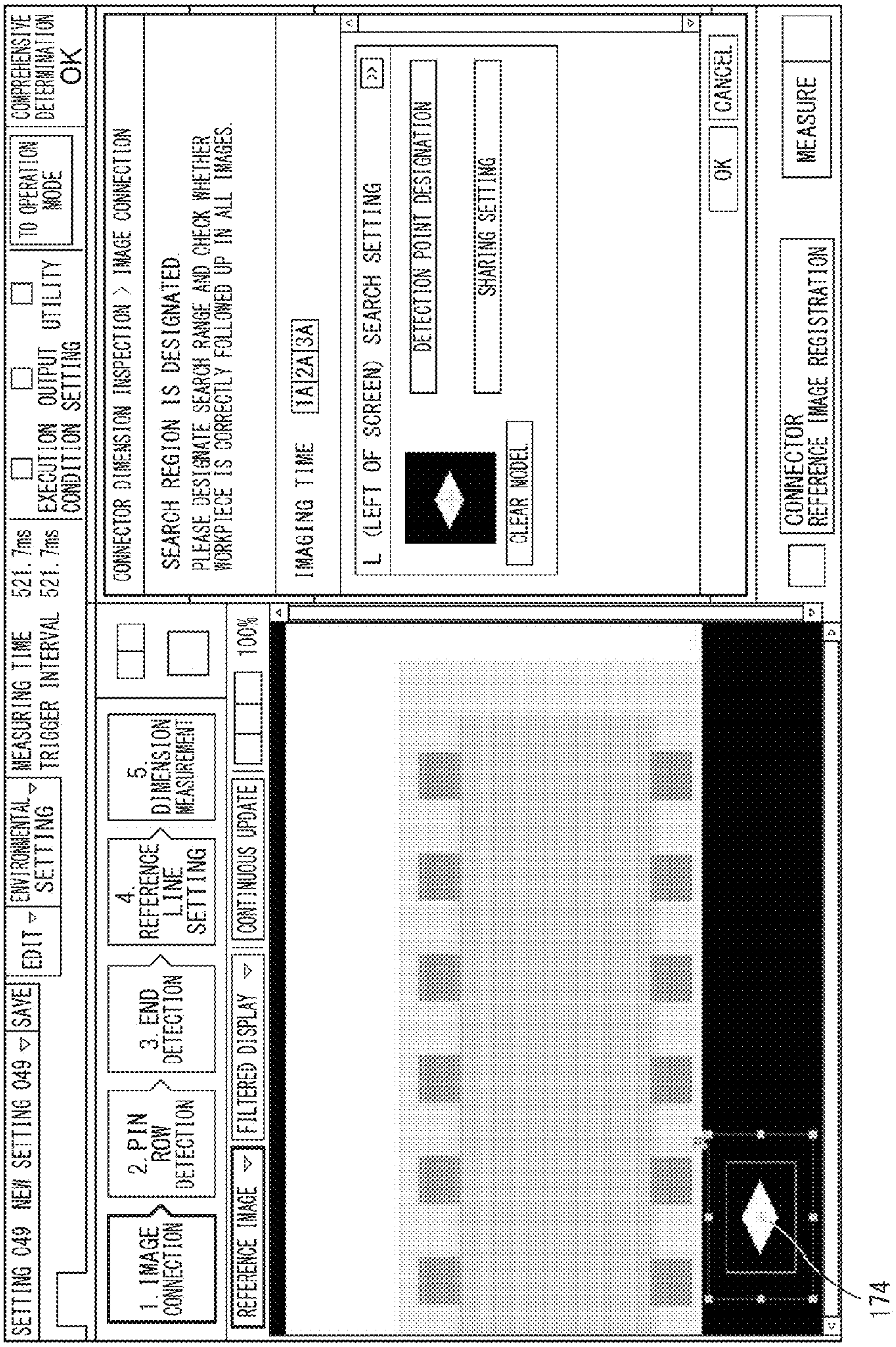
FIG. 48 is a diagram illustrating a setting screen on which a mark serving as a reference of an image connection is set.

FIG. 48 is a diagram illustrating a setting screen on which a mark 170 serving as a reference of an image connection is set. The CPU 22 enables a reference point 174 serving as a reference for connecting a right-end image and an image of a middle portion, the inspection region, and the search region to be easily set by enlarging and displaying a right-end image of the connector. The user sets the reference point 174 at the center of the mark 170 by operating the mouse 9. Further, the CPU 22 sets the inspection region and the search region based on the reference point 174. The CPU 22 may finely adjust the reference point 174 according to the operation of the mouse 9 or adjust positions and sizes of the inspection region and the search region.

Figure 49:
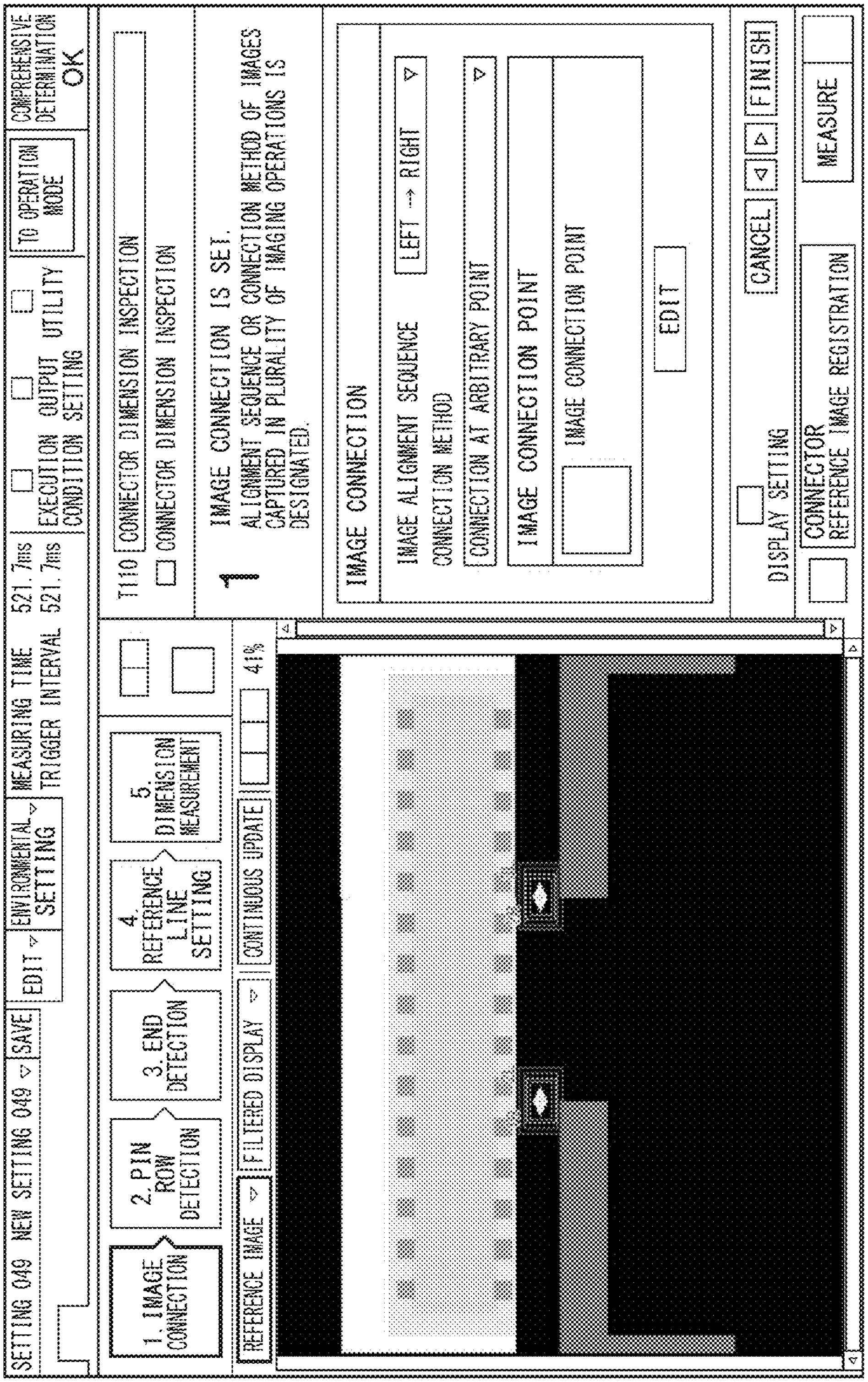
FIG. 49 is a diagram illustrating front-light images and back-light images connected based on the marks.

FIG. 49 illustrates front-light images and back-light images connected based on the marks 170. When the left-end image, the image of the middle portion, and the right-end image of the connector are connected, the image processing section 30 connects the left-end image and the image of the middle portion so that the reference points 171 and 172 are superimposed. Further, the image processing section 30 connects the image of the middle portion and the right-end image so that the reference points 173 and 174 are superimposed. Thereby, a connection image (full image) in which the entire inspection object 8 is held is created. Because coordinate systems in the front-light image and the back-light image are consistent, a connection to the back-light image can be similarly made based on a connection position of the front-light image. As illustrated in FIG. 49, when there are only the left-end image and the right-end image for the back-light image, the origins (upper-left corners of the images) of the left-end image of the front-light image and the left-end image of the back-light image are caused to be consistent. In addition, the origins (upper-left corners of the images) of the right-end image of the front-light image and the right-end image of the back-light image are caused to be consistent. Thereby, as illustrated in FIG. 49, the front-light image and the back-light image showing the entire connector are created.

<Pin or Housing Detection Method>

The above-described embodiment is an example in which the housing or pin of the inspection object 8 is detected using pattern matching using a model image. However, the model image is not indispensable.

Figure 50:
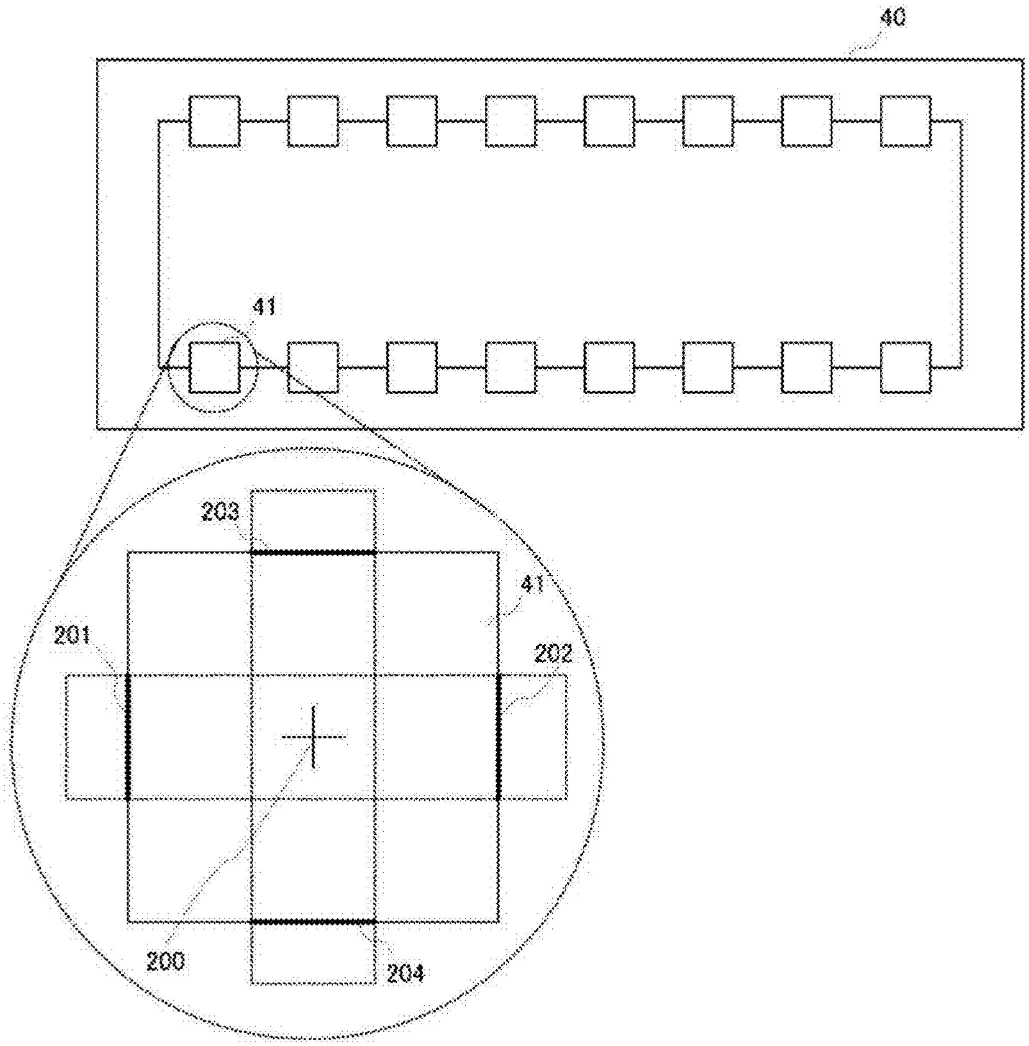
FIG. 50 is a diagram illustrating a pin detection method using edge detection.

FIG. 50 is a diagram illustrating a pin detection method using edge detection. The image processing section 30 detects a plurality of edges of a horizontal direction or a plurality of edges of a vertical direction by executing edge detection. Accordingly, a middle position (center position) of a detected edge of a predetermined direction is automatically set as a reference point 200. The image processing section 30 calculates a distance from the reference point 200 to each edge, and searches for a combination of edges having the distance which is a predetermined distance (allowed in a fixed tolerance range). In this example, an edge 201 corresponding to the left end of the pin 41 and an edge 202 corresponding to the right end are recognized to be edges consistent with a pin detection condition. Likewise, the image processing section 30 recognizes an edge 203 corresponding to an upper end of the pin 41 and an edge 204 corresponding to a lower end as edges consistent with a pin detection condition. This is because a distance from the reference point 200 is consistent with the pin detection condition. Thus, the image processing section 30 can detect a position of each pin by executing edge detection for the entire image.

Figure 51:
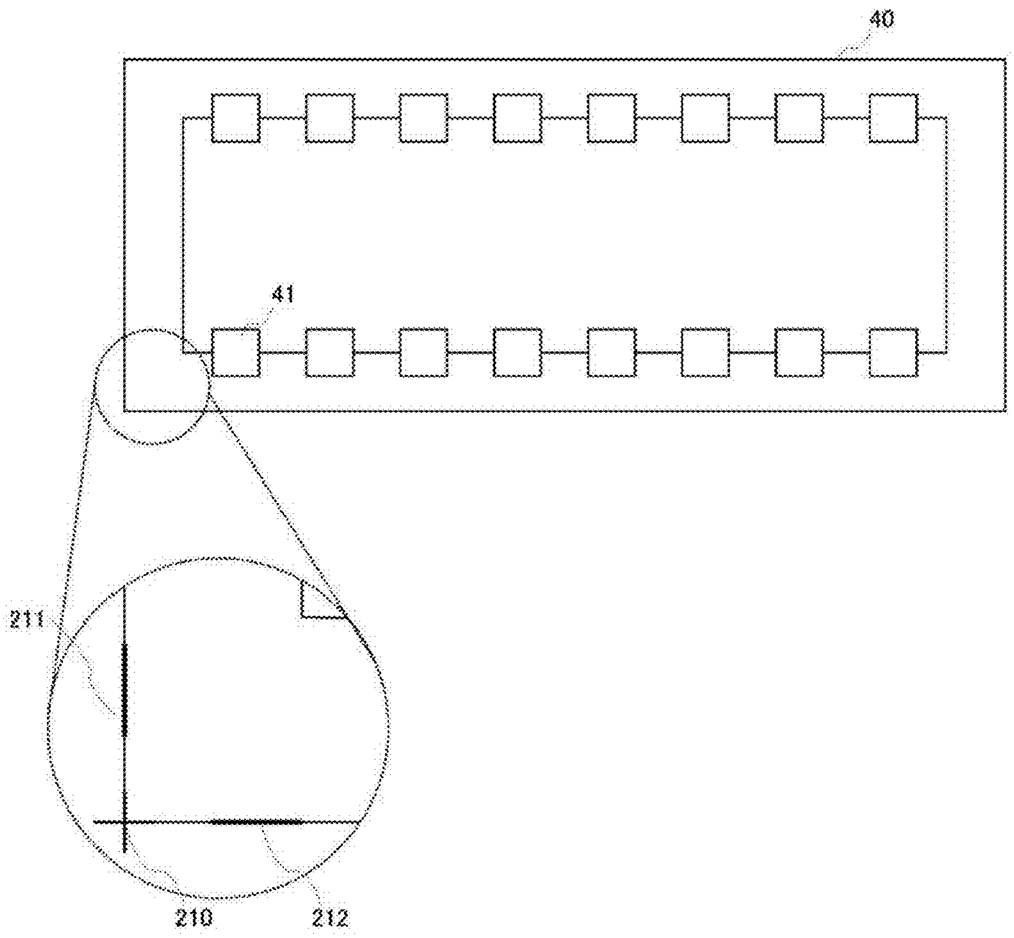
FIG. 51 is a diagram illustrating a housing detection method using edge detection.

FIG. 51 is a diagram illustrating a housing detection method using edge detection. The image processing section 30 detects a plurality of edges of the horizontal or vertical direction, and extracts an edge 211 and an edge 212 orthogonal to each other at a reference point 210. Here, the edges 211 and 212 are edges positioned at the outermost position. The reference point (intersection point) 210 is automatically set as a point at which the edge 211 intersects the edge 212 after the edges 211 and 212 are extracted. By presetting such a detection condition, the image processing section 30 may detect an edge of the housing edge detection.

<Reference of Measurement Regions Among Plurality of Measurement Tools>

Figure 52:
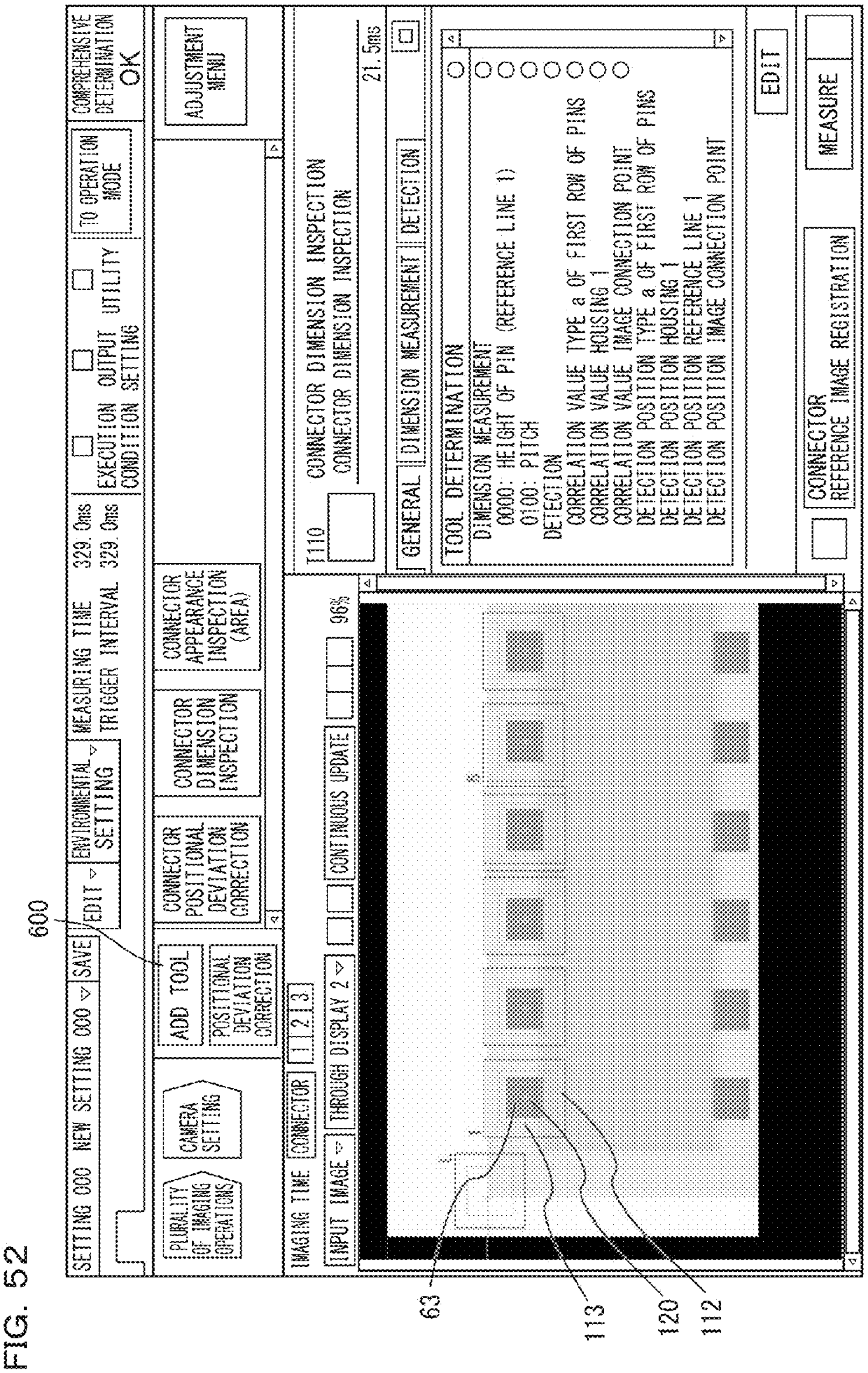
FIG. 52 is a diagram illustrating a plurality of parameters set for a connector dimension inspection tool.

FIG. 52 illustrates a plurality of parameters set for a connector dimension inspection tool. By pressing a tool addition button 600, a plurality of image processing tools (measurement tools), which perform an appearance inspection, are added. Here, for a pin 63 to be measured by the above-described connector dimension inspection tool, measurement regions (a search region 112, an inspection region 113, a reference point 120, and the like) are set.

Figure 53:
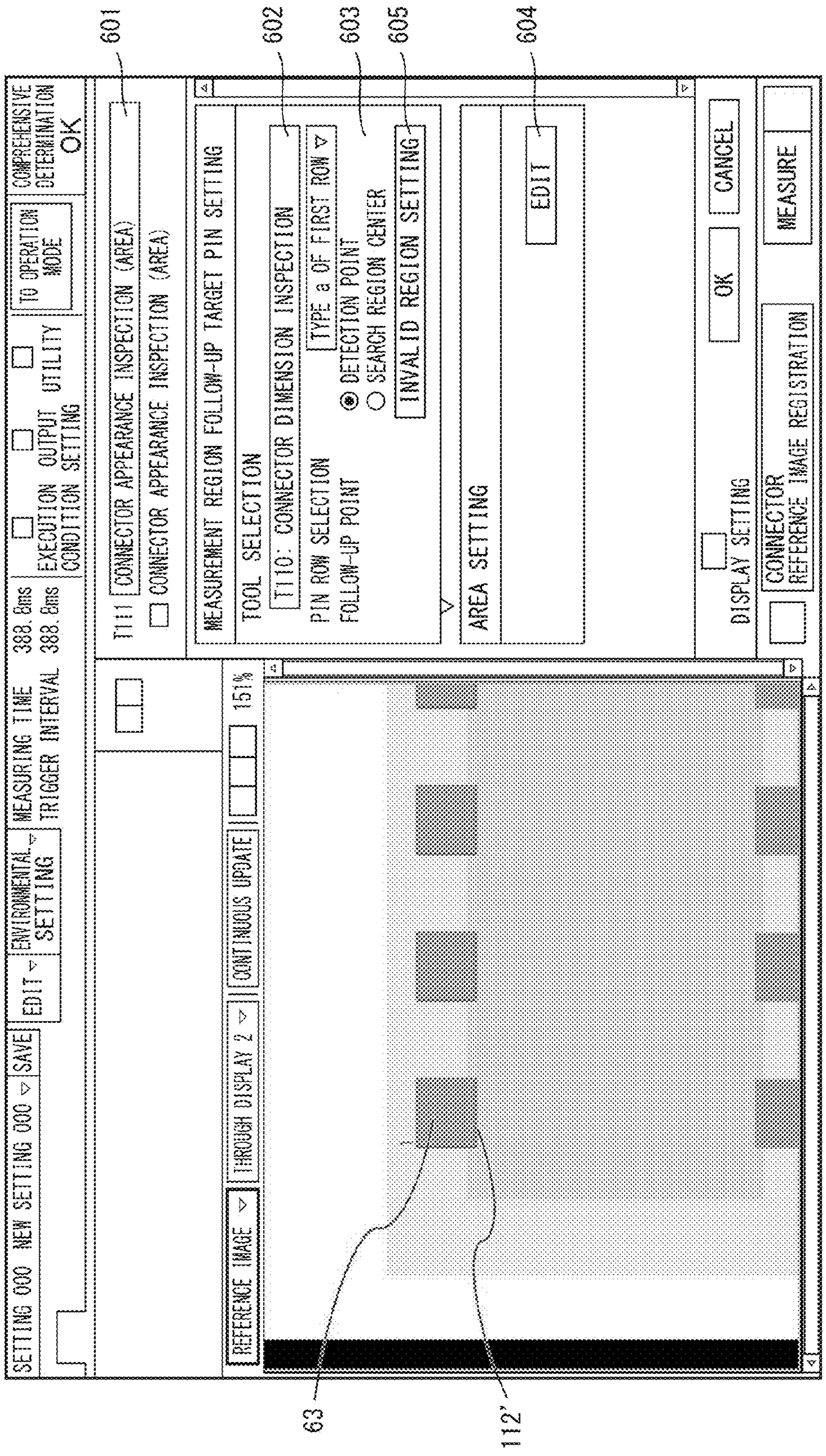
FIG. 53 is a diagram illustrating an example of a parameter setting screen for an area measurement tool which is one of connector appearance inspection tools.

FIG. 53 illustrates an example of a parameter setting screen for an area measurement tool which is one of connector appearance inspection tools. The area measurement tool, for example, is a tool which measures an area of a region sandwiched by two adjacent pins 63. By measuring the area, it is possible to determine whether a resin is placed around the pin 63 (resin fog) or whether a burr occurs in the pin 63 (metal burr). A measurement tool name field 601 indicates a name of a measurement tool which is a parameter setting target. A tool selection section 602 is a pull-down menu for selecting a measurement tool to be referred to when a measurement region 112' is set for an area measurement tool. Here, the measurement region 112' for the area measurement tool is temporarily set by copying a search region 112 for the connector appearance inspection tool. A follow-up point selection section 603 is a radio button for selecting a point (for example, a detection point or a center point of the search region) of the connector dimension inspection tool the measurement region 112' for the area measurement tool follows up.

Figure 54A:
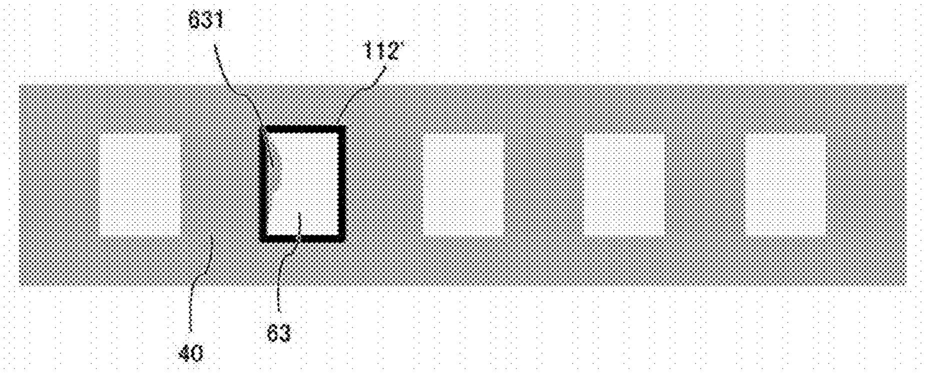
FIG. 54A is a diagram illustrating an example of fog.

FIG. 54A is a diagram illustrating an example of fog. A resin constituting the housing 40 is placed on a left-end side of the pin 63. Such fog 631 causes a contact defect, so that it is necessary to determine a product as a defective product. The area measurement tool measures the area of the pin 63 to compare the measured area to a threshold value or measures an area between two adjacent pins 63 to compare the measured area to a threshold value, thereby finding such fog 631.

Figure 54B:
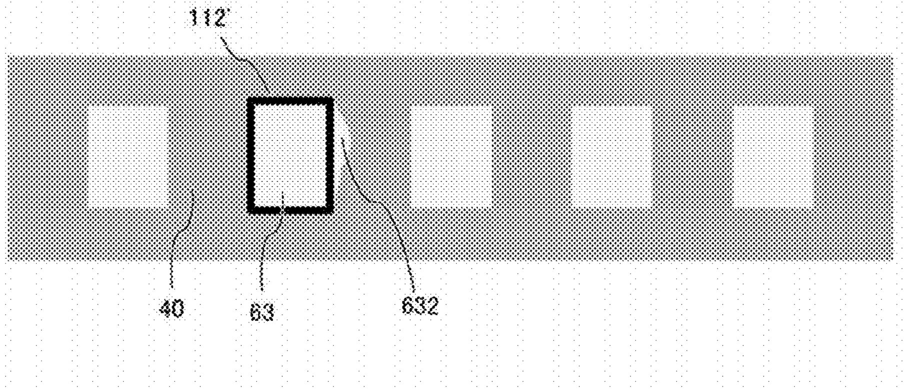
FIG. 54B is a diagram illustrating an example of a burr.

FIG. 54B is a diagram illustrating an example of a burr. The burr 632 occurs at a right end of the pin 63. Because such a burr 632 shortens an insulation distance between adjacent pins, it is necessary to determine a product as a defective product. The area measurement tool measures the area of the pin 63 to compare the measured area to a threshold value or measures an area between two adjacent pins 63 to compare the measured area to a threshold value, thereby finding such a burr 632. In order to measure the area of the pin 63, the measurement region 112' is set in conjunction with the area of the pin 63. In addition, in order to measure the area between two adjacent pins 63, the measurement region 112' is moved between the two pins 63 and a size of the measurement region 112' is adjusted if necessary.

Figure 55:
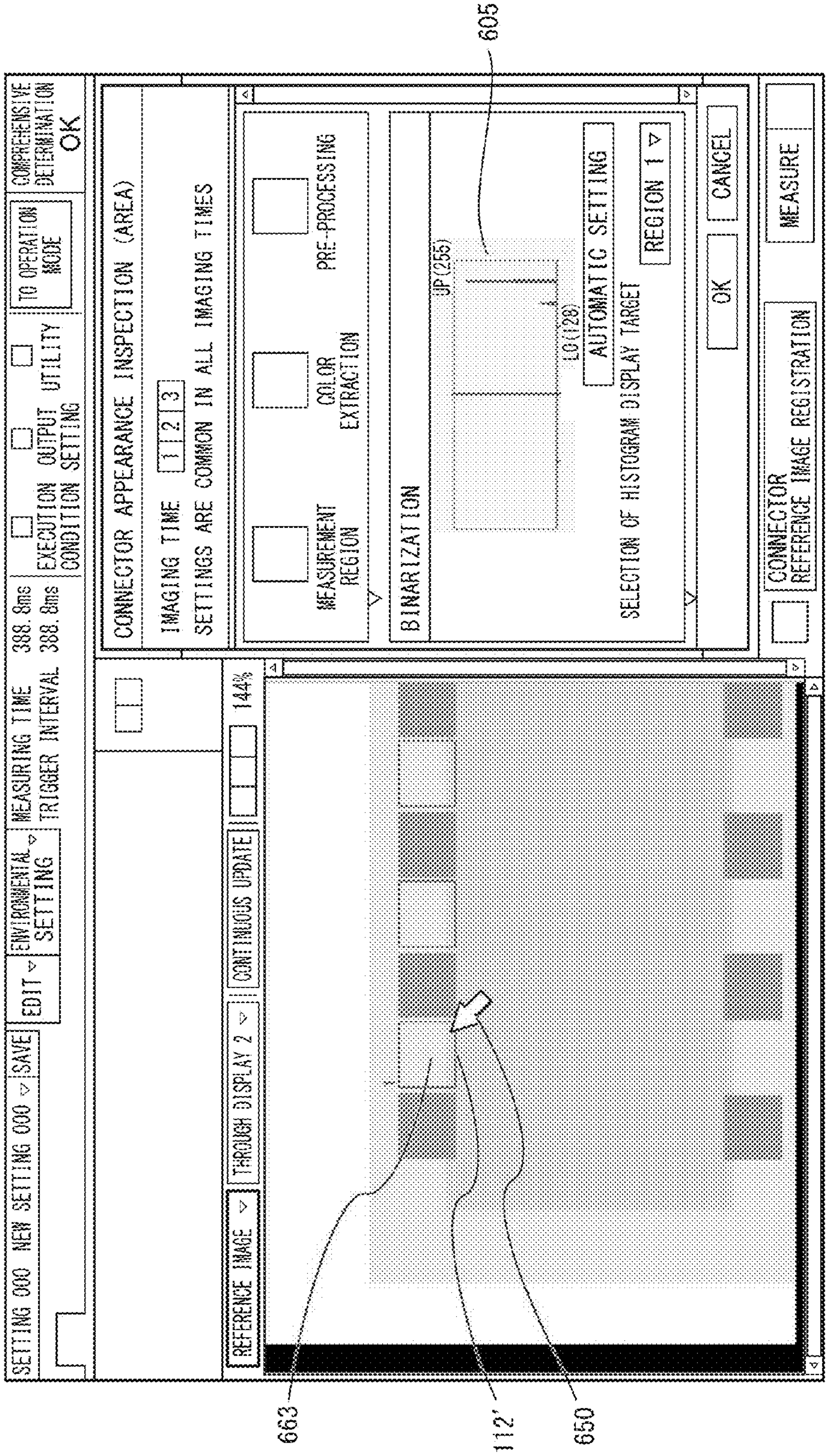
FIG. 55 is a diagram illustrating an example of the user interface for copying, finely adjusting, and setting a parameter for a certain measurement tool as a parameter of another measurement tool.

FIG. 55 illustrates a user interface for copying, finely adjusting, and setting a parameter for a certain measurement tool as a parameter of another measurement tool. As illustrated in FIG. 52, the search region 112 for the connector dimension inspection tool is set in each pin 63. In addition, as illustrated in FIG. 53, in an initial state, the measurement region 112' is set based on the search region 112 for the connector dimension inspection tool. The screen transitions to an edit screen illustrated in FIG. 55 by operating to press an edit button 604 illustrated in FIG. 53 using the mouse 9.

In FIG. 55, the user drags the measurement region 112' in a right direction by operating a pointer 650 using the mouse 9, so that the measurement region 112' is offset and set between two adjacent pins. A plurality of measurement regions 112' are offset in association with each other. That is, a drag amount of the pointer 650 serves as an offset amount. In addition, a result obtained by adding an offset amount to coordinate data of the search region 112 of the connector dimension inspection tool becomes coordinate data of the measurement region 112' for the area measurement tool. In addition, sizes of the plurality of measurement regions 112' are changed in association with each other. Sizes of all measurement regions 112' are changed in association with each other by dragging the pointer 650 to the vicinity of a corner or side of one certain search region 112 by operating the mouse 9.

The measurement result of the measurement region selected by the pointer 650 is displayed as a histogram on a histogram display section 605. The user can check whether the measurement region 112' for the area measurement tool is accurately set by checking the histogram.

Figure 56:
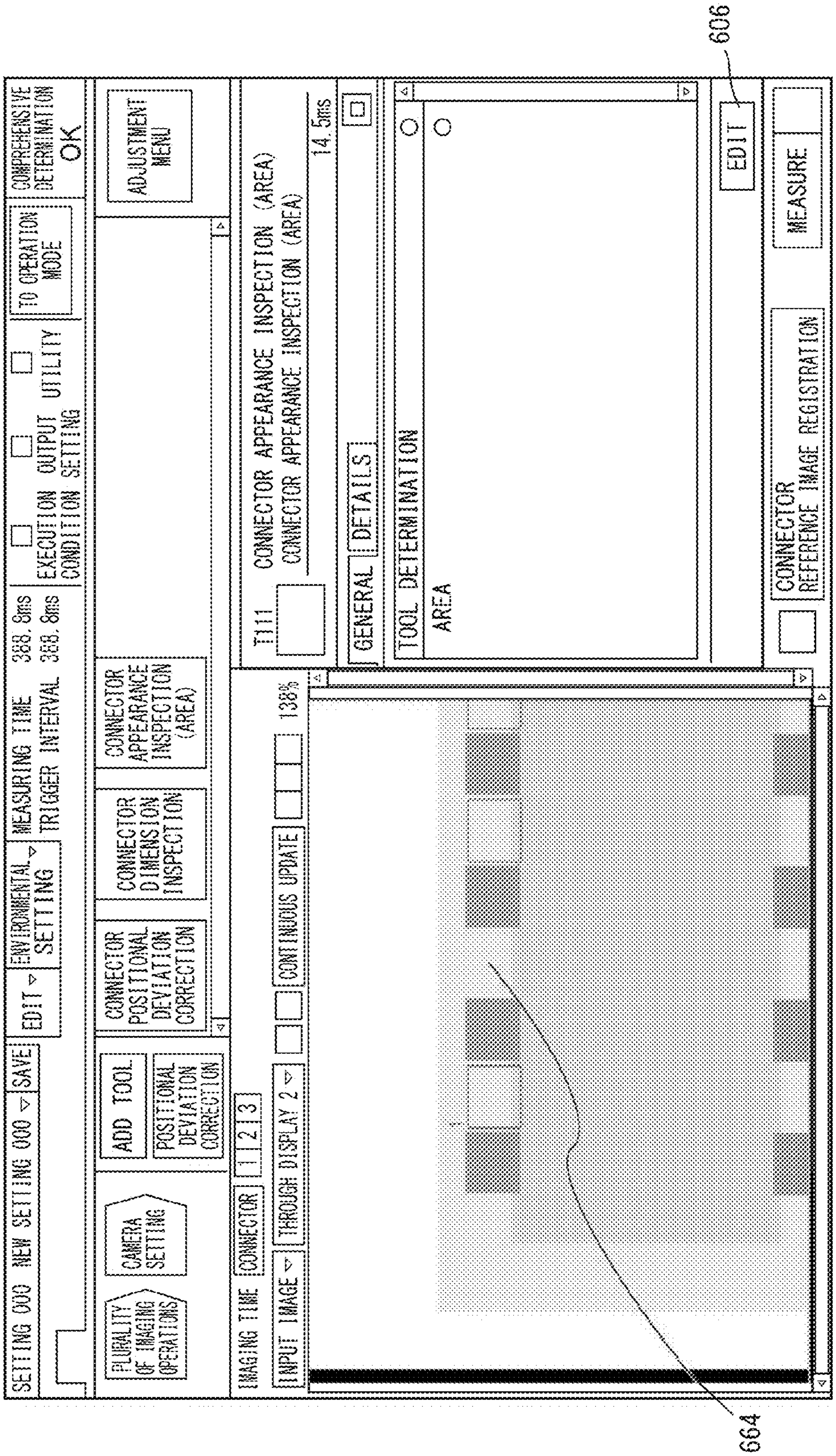
FIG. 56 is a diagram illustrating an example of a connector in which there is pin loss.

FIG. 56 is a diagram illustrating an example of a connector in which there is pin loss. In principle, pins are arranged at equal intervals in the connector. However, when it is ensured that some pins are unused, cost reduction of the connection or the like is promoted without forming the pins. In this case, a reference point 120 or the like is not set at a pin loss position in the connector dimension inspection tool. Consequently, when the area measurement for the pin loss position is necessary, the coordinate data of the reference point 120 of the connector dimension inspection tool is not referred to for the measurement region 112'. Accordingly, the screen transitions to the setting screen illustrated in FIG. 57 by operating an invalid region setting button **604*a* illustrated in FIG. 53 using the mouse 9**.

Figure 57:
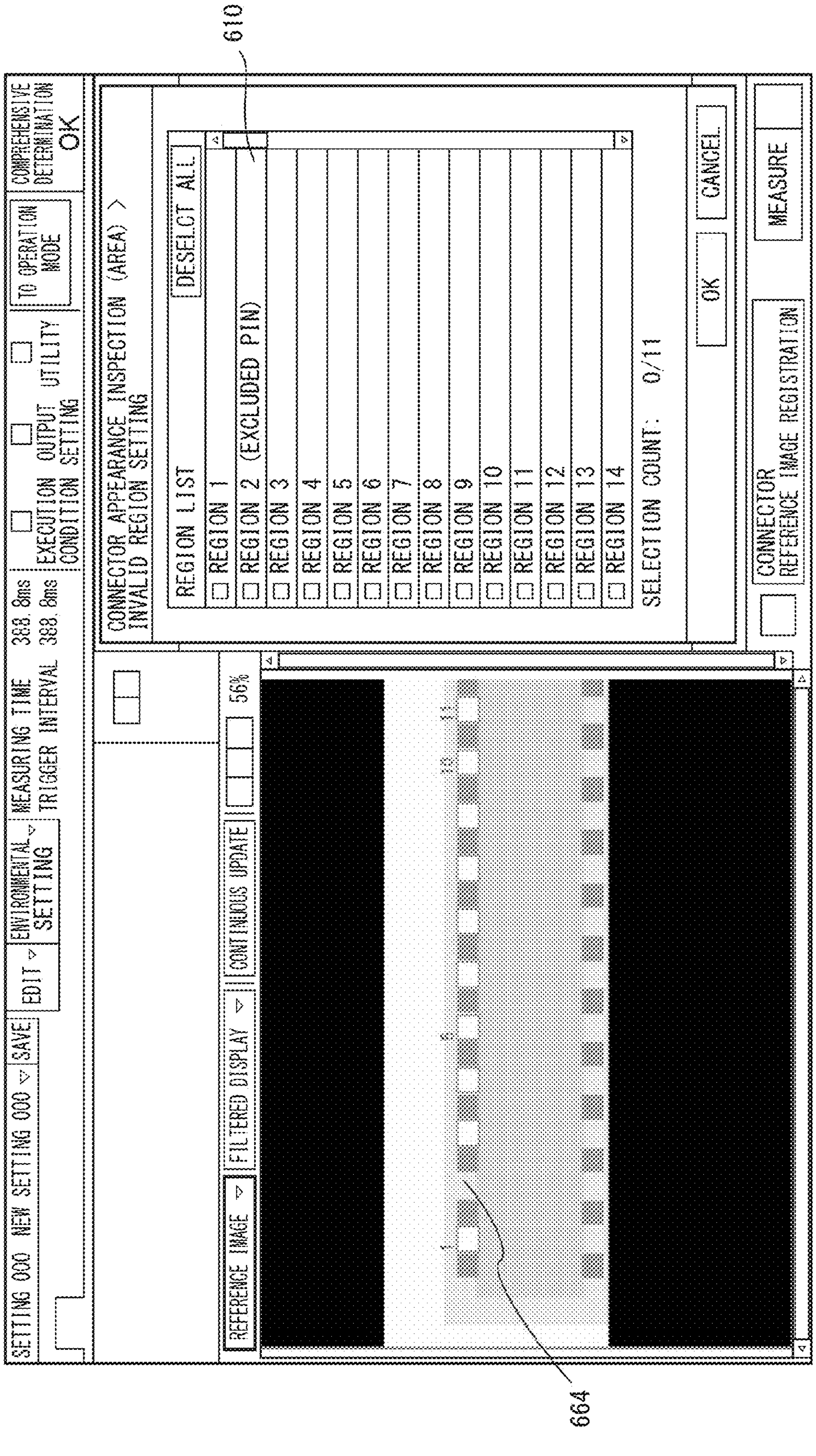
FIG. 57 is a diagram illustrating an example of an invalid region setting screen.

FIG. 57 is a diagram illustrating an example of an invalid region setting screen. According to FIG. 57, because pin loss 664 is set in the 2nd pin counted from the left, the measurement region 112' is not set between the 2nd pin and a 3rd pin. Accordingly, by checking a check box corresponding to a region between the 2nd pin and the 3rd pin in an invalid region setting section 610, the region is added as the measurement region 112'.

Figure 58:
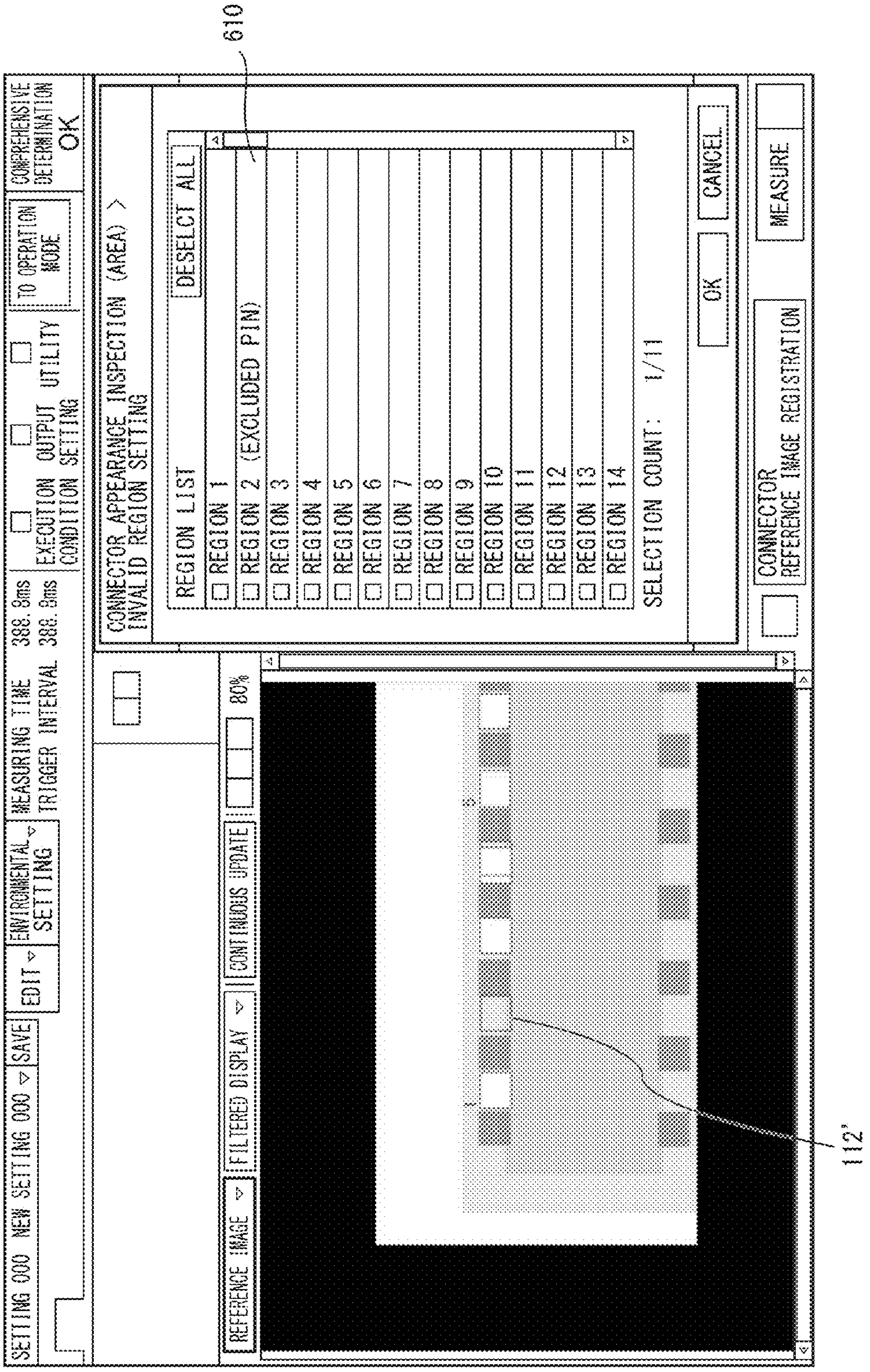
FIG. 58 is a diagram illustrating an example in which a measurement region has been set in the vicinity of a pin loss position.

FIG. 58 is a diagram illustrating an example in which the measurement region 112' has been set in the vicinity of a pin loss position. When the invalid region setting section 610 is checked, a position of the measurement region 112' for the pin loss position is determined using the fact that measurement regions 112' are arranged at equal intervals.

Detection Point Follow-Up and Search Region Center Follow-Up

Figure 59:
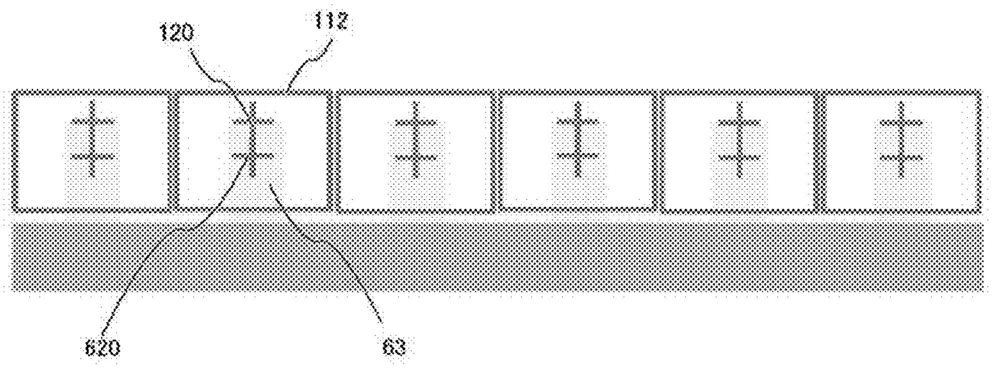
FIG. 59 is a diagram illustrating a difference between detection point follow-up and search region center follow-up.

FIG. 59 is a diagram illustrating a difference between the detection point follow-up and the search region center follow-up. As described above, in the connector dimension inspection tool, the search region 112, the inspection region 113, and the detection point (reference point 120) are set. As illustrated in FIG. 59, the center point of the search region 112 is referred to as a search region center 620. Here, in order to copy a parameter of the connector dimension inspection tool as a parameter of the area measurement tool, a method of executing a copy operation based on the reference point 120 and a method of executing a copy operation based on the search region center 620 are considered. These methods have both merits and demerits. When there is pin bending, a method of performing a copy operation based on the reference point 120 is advantageous. When the above-described pin loss is present, a method of executing a copy operation based on the search region center 620 is advantageous.

Figure 60A:
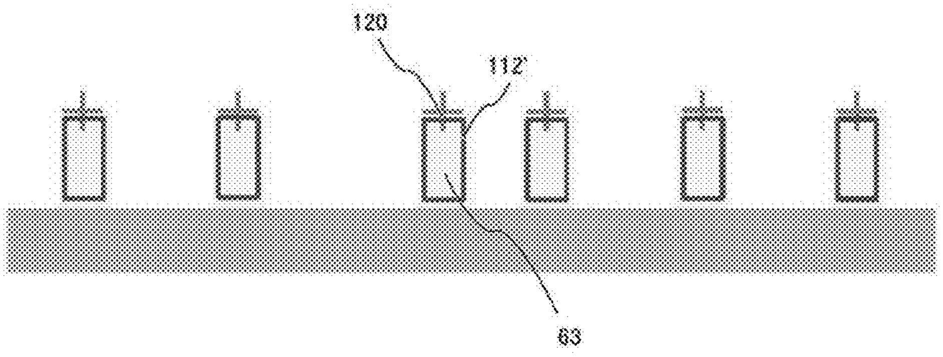
FIG. 60A is a diagram illustrating an example in which a measurement region of an area measurement tool is set based on a reference point of the connector dimension inspection tool for a connector in which there is pin bending.

FIG. 60A is a diagram illustrating an example in which the measurement region 112' of an area measurement tool is set based on the reference point 120 of the connector dimension inspection tool for a connector in which there is pin bending.

In this example, because the reference point 120 of the connector dimension inspection tool is set at a tip of an actual pin, the measurement region 112' is accurately set by detecting a pin tip through pattern recognition even when pin bending occurs.

Figure 60B:
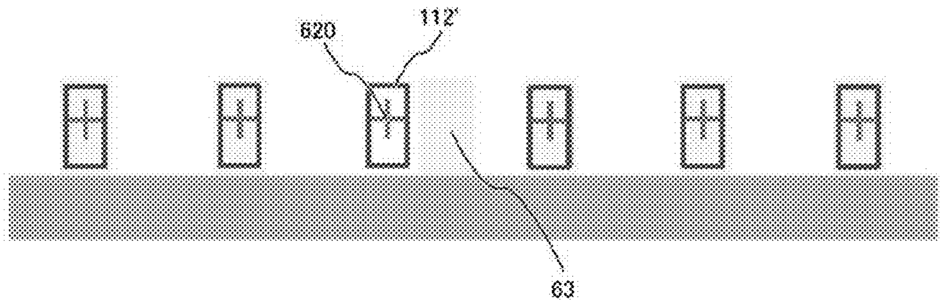
FIG. 60B is a diagram illustrating an example in which a measurement region of the area measurement tool is set based on a search region center of the connector dimension inspection tool for a connector in which there is pin bending.

FIG. 60B is a diagram illustrating an example in which a measurement region 112' of the area measurement tool is set based on a search region center 620 of the connector dimension inspection tool for a connector in which there is pin bending. In this example, because the measurement region 112' of the area measurement tool is set based on the search region center 620, the position of the measurement region 112' is deviated from the position of the actual pin 63. This is because the search region 112 serving as a source of the measurement region 112' of the area measurement tool is a fixed region. That is, this is because the reference point 120 is dynamically corrected through pattern recognition according to an actual pin position, but the search region 112 is not corrected.

Figure 61A:
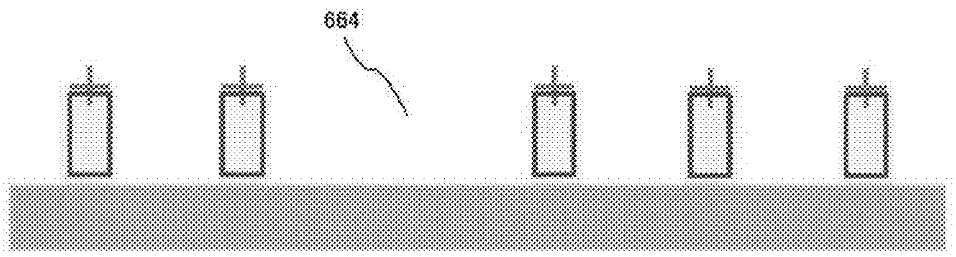
FIG. 61A is a diagram illustrating an example in which a measurement region of an area measurement tool is set based on a reference point of the connector dimension inspection tool for a connector in which there is pin loss.

FIG. 61A is a diagram illustrating an example in which the measurement region 112' of an area measurement tool is set based on the reference point 120 of the connector dimension inspection tool for a connector in which there is pin loss. As described above, when there is pin loss 664, no reference point 120 is set for a pin thereof. That is, because there is no reference point 120 serving as a reference for setting the measurement region 112' of the area measurement tool, it is difficult to simply set the measurement region 112' of the area measurement tool. Consequently, an additional setting method as described using FIGS. 57 and 58 is necessary.

Figure 61B:
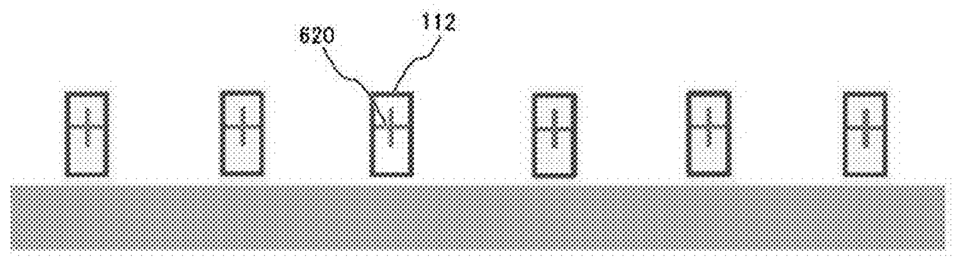
FIG. 61B is a diagram illustrating an example in which a measurement region of the area measurement tool is set based on a search region center of the connector dimension inspection tool for a connector in which there is pin bending.

FIG. 61B illustrates an example in which the measurement region 112' of the area measurement tool is set based on the search region center 620 of the connector dimension inspection tool for a connector in which there is pin bending. Because the search region 112 is fixedly set at an equal interval even when pin loss occurs, the measurement region 112' of the area measurement tool can be set as long as it is based on the search region center 620.

Thus, it is possible to detect whether a pin is erroneously formed regardless of whether a foreign object is attached to a pin loss position or the pin loss position by setting the measurement region 112' of the area measurement tool at the pin loss position.

For the search region center 620 and the reference point 120, marks such as cross-shaped marks having different colors are marked so that their positions are easily known.

<Internal Processing>

Here, functions implemented by the CPU 22 and the image processing section 30 will be described. Each function may be implemented by only the CPU 22, implemented by only the image processing section 30, or implemented by a combination operation of the CPU 22 and the image processing section 30.

Figure 62:
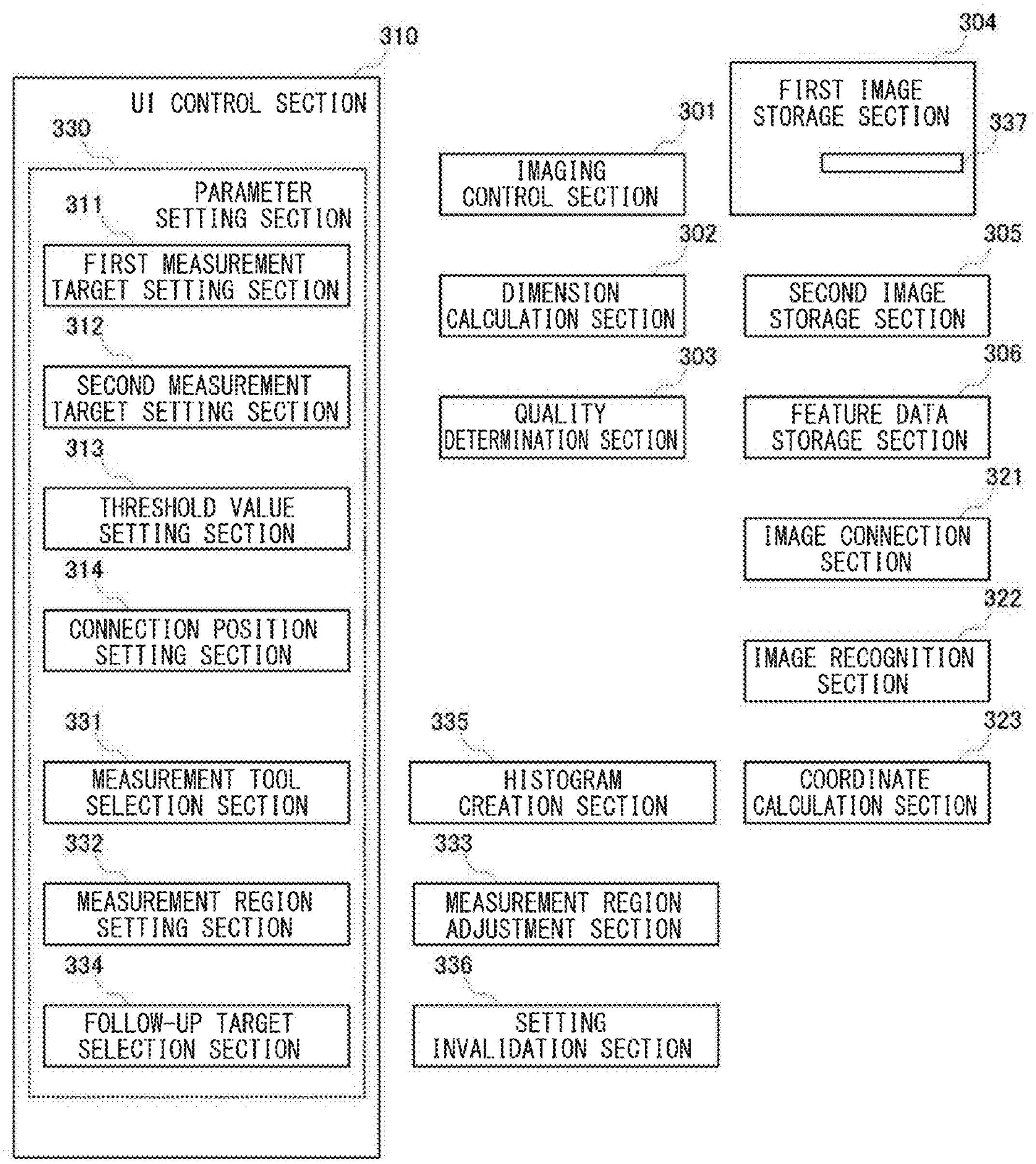
FIG. 62 is a functional block diagram of an appearance inspection device.

FIG. 62 is a functional block diagram of the appearance inspection device 1. As described above using FIG. 2, the illuminating device 5 functions as an illuminating section which radiates a plurality of different pieces of illumination light to the inspection object 8. The illumination control section 26 controls the illuminating device 5 so that the illuminating device 5 switches illumination light to be radiated according to an instruction from the CPU 22 or the image processing section 30. The camera 4 functions as an imaging section which images the inspection object 8 irradiated with illumination light using the illuminating device 5. In addition, the appearance inspection device 1 is a device which executes measurement processing on an image of the inspection object 8 acquired by the camera 4.

An imaging control section 301 is a control section which commands the illumination control section 26 to switch illumination light such as front light or back light or commands the camera 4 to perform imaging. The imaging control section 301 is also responsible for control of the camera 4 and control of the illuminating device 5 when the inspection object 8 is divided and imaged.

A first image storage section 304 stores a first image (e.g., a front-light image, its partial image, or the like) acquired by an imaging operation of the camera 4 on a predetermined region (e.g., the entire connector or a left end, a middle, or a right end of the connector) of the inspection object 8 irradiated with first illumination light (e.g., front light) using the illuminating device 5. A second image storage section 305 stores a second image (e.g., a back-light image, its partial image, or the like) acquired by an imaging operation of the camera 4 on a predetermined region of the inspection object 8 irradiated with second illumination light (e.g., back light) using the illuminating device 5. The first image storage section 304 or the second image storage section 305, for example, is implemented by the work memory 23. The display control section 28 or the monitor 10 functions as a display section which displays the first image and the second image.

A UI control section 310 controls a user interface of a display system such as the above-described UI 60 and an interface of an input system such as the mouse 9 or a keyboard. The UI control section 310 is further divided into various functional sections. The parameter setting section 330 sets a plurality of parameters including a model image, which is an image of a portion to be measured and numerical values necessary for measurement processing, for a basic image such as a reference image. The parameter setting section 330 is further divided into various functional sections. As described using FIGS. 21 to 25, a first measurement target setting section 311 sets a characteristic portion (e.g., pin detection point) serving as an initial point for measuring a dimension related to the inspection object 8 in one image of the first and second images displayed on the monitor 10.

As described using FIGS. 30 to 37, a second measurement target setting section 312 sets a characteristic portion (e.g., a detection point for detecting a corner of the housing, a reference line connected among a plurality of detection points, or the like) serving as the end point for measuring a dimension related to the inspection object 8 in the other image of the first and second images displayed on the monitor 10. Data such as a model image, a reference point, and a reference line set by the first measurement target setting section 311 or the second measurement target setting section 312 is stored in a characteristic data storage section 306. The characteristic data storage section 306 is also implemented by the work memory 23.

A dimension calculation section 302 functions as a measurement processing section which executes measurement processing on the inspection object 8 using a plurality of parameters for an image of the inspection object 8 to be conveyed on the line imaged and acquired by the camera 4. For example, the dimension calculation section 302 calculates a dimension from the characteristic portion serving as an initial point set by the first measurement target setting section 311 to the characteristic portion serving as the end point set by the second measurement target setting section 312. Here, the dimension is a distance, an area, or the like.

The UI control section 310 may have a threshold value setting section 313 which sets a threshold value for determining quality of the appearance of the inspection object 8. A quality determination section 303 determines the quality of the appearance of the inspection object 8 based on a measurement result of the measurement processing section (a comparison result between the dimension calculated by the dimension calculation section 302 and the threshold value or the like). For example, when a pin height obtained by the dimension calculation section 302 for each of the plurality of pins exceeds an upper limit obtained by the threshold value setting section 313 from a tolerance or a standard value, the quality determination section 303 determines that the pin is defective.

As described using FIG. 6 and the like, the UI control section 310 creates display data of a user interface in which the monitor 10 simultaneously displays a first image and a second image so that an end of the horizontal direction of the first image is consistent with an end of the horizontal direction of the second image, and delivers the created display data to the display control section 28. That is, the UI control section 310 creates the display data so that the monitor 10 vertically arranges and displays the first image and the second image by aligning the ends in the horizontal direction of the first image and the ends in the horizontal direction of the second image. In addition, the UI control section 310 creates display data so that an index (e.g., a cross-shaped mark or the like indicating a search region, an inspection region, or a detection point) indicating a characteristic portion serving as an initial point set for one image of the first and second images is displayed in association with the other image of the first and second images. The UI control section 310 may create display data for displaying an index indicating a characteristic portion serving as the end point set for the other image of the first and second images in association with the one image of the first and second images. Thus, in the UI 60, the cross-shaped mark or the like indicating the search region, the inspection region, or the detection point is configured to be displayed in association between the front-light image and the back-light image. For example, the UI control section 310 also directly sets and displays the search region, the inspection region, and the detection point set using the back-light image on the front-light image. When the origin of the back-light image is set at an upper-left corner of the back-light image and the origin of the front-light image is set at an upper-left corner of the front-light image, coordinates of the search region, the inspection region, and the detection point set using the back-light image are caused to be consistent with coordinates of the search region, the inspection region, and the detection point in the front-light image. Thereby, when the origin of the front-light image is set at an upper-left corner of the front-light image, the UI control section 310 causes the search region, the inspection region, and the detection point set using the back-light image to be displayed in association with the search region, the inspection region, and the detection point in the front-light image.

The first measurement target setting section 311 and the second measurement target setting section 312 set reference points 82, 85, 120, 131, 171, 172, 173, 174, 200, and 210, which are coordinates of one or more positions on an image, as characteristic portions.

As described using FIG. 21 and the like, the UI control section 310 may create display data for enabling the monitor 10 to enlarge and display one of the images. The first measurement target setting section 311 sets a characteristic portion on the one image enlarged and displayed on the monitor 10 according to an operation of the mouse 9.

As described using FIG. 30 and the like, the UI control section 310 may create display data for enabling the monitor 10 to enlarge and display the other image. The second measurement target setting section 312 sets a characteristic portion on the other image enlarged and displayed on the monitor 10 according to the operation of the mouse 9.

As described using FIGS. 35 to 37, the second measurement target setting section 312 may set the reference line 81, which is a straight line connecting two reference points designated for the other image, as a characteristic portion. In particular, when a corner of the housing 40 is set as the reference point, it is difficult to detect the corner in the front-light image. A position of the corner can be accurately detected by setting the corner of the housing 40 as a reference point for the back-light image. Accordingly, a distance from the center of the pin to the corner can also be accurately calculated. Further, the accuracy of a quality determination on a product can also be improved.

As described using FIG. 5 and the like, an image connection section 321 creates first and second images by arranging and connecting a plurality of partial images, which have been obtained by the camera 4 dividing and imaging the inspection object 8 a plurality of times, from left to right in order of imaging. Here, the image connection section 321 may connect a plurality of partial images constituting a second image using coordinates of connection positions (e.g., positions of commonly imaged pins or marks) of a plurality of partial images constituting the first image. The UI control section 310 may further include the connection position setting section 314 which sets a connection position in the first image. The connection position setting section 314 may set positions of parts (e.g., pins, metal fittings, or the like) of the inspection object commonly shown in adjacent partial images as connection positions. As described using FIGS. 45 to 49, the connection position setting section 314 may set positions of parts (e.g., marks 170) of a jig, which fixes the inspection object commonly shown in adjacent partial images, to connection positions.

The image connection section 321 may create the second image by arranging partial images of left and right ends of the inspection object 8 at both ends of the second image and omitting the image of the middle of the inspection object 8.

In FIG. 62, an image recognition section 322 compares a model image showing part of a non-defective product of the inspection object 8 set through the UI control section 310 to the image of the inspection object 8 flowing on the line acquired by the camera 4, and specifies a portion consistent with the model image through pattern recognition. The image recognition section 322 searches for the model image in a range of a preset search region. An image region having the same size as the model image becomes an inspection region. The center of the inspection region consistent with the model image serves as the reference point. The reference point may be finely adjusted through the UI control section. Coordinate data of the search region or coordinate data of the reference point (detection point) is stored in the characteristic data storage section 306, and used by the image recognition section 322, the image connection section 321 and a coordinate calculation section 323. The coordinate calculation section 323 calculates coordinates of the search region, the inspection region, and the reference point from coordinate data indicating a position of a pointer of the mouse 9 and coordinate data of the back-light image or the front-light image.

A basic image storage section 337 stores a basic image obtained by the camera 4 imaging the inspection object 8 having a plurality of characteristic portions arrayed in a specific direction (e.g., pins 63 having substantially the same shape arranged according to a fixed rule). The UI control section 310 displays the basic image of the inspection object 8 on the monitor 10 as illustrated in FIGS. 52 to 54, FIGS. 56 to 58, and the like. The first measurement target setting section 311 functions as a position detection region setting section which sets, to the basic image displayed on the monitor 10, a position detection region (e.g., the search region 112) for detecting positions of a plurality of characteristic portions of the inspection object 8 according to each characteristic portion. The first measurement target setting section 311 may set, as the position detection region, a search region for searching for a characteristic portion and a detection point serving as a reference of position detection associated with position of a characteristic portion detected within the search region. For example, the first measurement target setting section 311 may set coordinates predetermined for an inspection region such as an upper-right corner, an upper-left corner, a center, and the like of the inspection region consistent with the model image within the search region as the detection point. Position detection regions may be set by the user one by one for respective pins, or arranged at equal intervals by the first measurement target setting section 311 using the fact that the respective pins are arranged at equal intervals.

A measurement tool selection section 331 selects, from a plurality of measurement tools for performing different measurement, a measurement tool that measures the inspection object 8. When it is sensed that the tool addition button 600 illustrated in FIG. 52 has been operated with the mouse 9, the measurement tool selection section 331 displays a selection screen for selecting one measurement tool from a plurality of measurement tools and selects a measurement tool designated with the mouse 9 in the selection screen. In the example illustrated in FIG. 52, a connector appearance inspection (area) tool is already added. When a connector appearance inspection (area) tool arranged as a button in FIG. 52 is selected with the mouse 9, the measurement tool selection section 331 causes a setting screen illustrated in FIG. 53 to be displayed on the monitor 10.

A measurement region setting section 332 sets the measurement region 112' which is a region to be measured by the measurement tool selected by the measurement tool selection section 331 based on a position detection region (e.g., the reference point 120 or the search region 112) set by the first measurement target setting section 311. As described using FIG. 53 and FIGS. 55 to 58, the measurement region setting section 332 sets the measurement region 112' by copying coordinate data of the reference point 120 or the search region 112. As described using FIG. 53 and FIGS. 55 to 58, the monitor 10 displays the measurement region 112' set by the measurement region setting section 332 along with a basic image. The quality determination section 303 measures the inspection object 8 conveyed on the line according to the measurement region 112' set by the measurement region setting section 332, and determines quality of the inspection object 8 based on the measurement result.

A measurement region adjustment section 333 adjusts at least one of the position and size of the measurement region 112' set by the measurement region setting section 332 based on the position detection region set by the first measurement target setting section 311. As described using FIG. 57, the measurement region adjustment section 333 moves the position of the measurement region 112' or enlarges or reduces the size of the measurement region 112' according to an operation of the pointer 650 with the mouse 9. The measurement region adjustment section 333 may adjust each of positions or sizes of a plurality of measurement regions 112' set by the measurement region setting section 332 by an equal adjustment amount. Likewise, the measurement region adjustment section 333 may adjust angles of the plurality of measurement regions 112' set by the measurement region setting section 332 by the equal adjustment amount. The measurement region 112' is rotatable. Therefore, the plurality of measurement regions 112' may each be rotated at an equal angle. The user drags one measurement region 112' using the mouse, so that the position and size of the measurement region 112' can be adjusted, and the adjustment amount is also reflected in another measurement region 112'. That is, all the measurement regions 112' are configured to be adjusted by the equal adjustment amount. However, when pins are arranged in two rows, adjustment may be individually performed in first and second rows and the adjustment may be integrated and reflected in the first and second rows. Alternatively, adjustment by such association may not be performed. That is, the measurement region adjustment section 333 may individually adjust only one or more measurement regions 112' selected with the mouse 9 according to an operation amount of the mouse 9. Thus, a continuous tenability mode and an individual adjustment mode may be prepared and switched with the mouse 9.

As described using FIG. 59, the first measurement target setting section 311 sets a detection point (reference point 120) serving as a reference of position detection and a search region 112 for searching for an image consistent with a model image of a characteristic portion through pattern recognition as a position detection region. As described using FIGS. 60 and 61, the measurement region setting section 332 sets the measurement region 112' so as to follow up the detection point (reference point 120) or the search region center 620 of the search region 112. A follow-up target selection section 334 selects the reference point 120 or the search region center 620 as the follow-up target of the measurement region according to the user's input. As described using FIG. 53, the follow-up target selection section 334 recognizes which of the reference point 120 and the search region center 620 has been selected by the user as the follow-up target of the measurement region through the follow-up point selection section 603 for selecting the follow-up point.

As described using FIG. 55, a histogram creation section 335 creates a histogram indicating an image density of the measurement region 112' set by the measurement region setting section 332. The monitor 10 displays the histogram created by the histogram creation section 335. The user can check whether the measurement region 112' is accurately set by viewing the histogram.

As described using FIG. 57, when there is pin loss in the connector, a setting invalidation section 226 invalidates one or more search regions corresponding to pin loss among the plurality of search regions 112 as an excluded pin. In this case, the measurement region setting section 332 cancels invalidation of the search region 112 invalidated by the setting invalidation section 226. The invalidation is cancelled by checking a check box corresponding to the excluded pin as described above. The measurement region setting section 332 sets the measurement region 112' based on the search region 112 in which the invalidation has been cancelled. On the other hand, the setting invalidation section 226 may invalidate one or more position detection regions among a plurality of position detection regions validated by the position detection region setting section according to an operation of the mouse 9 of the user. A necessary region in a dimension inspection may be unnecessary in another appearance inspection. In this case, the setting invalidation section 226 invalidates its position detection region, and hence the measurement region setting section 332 cannot refer to the invalidated position detection region.

The UI control section 310 causes the monitor 10 to overlay and display a mark (a cross-shaped mark or the like) indicating a position of a characteristic portion on a basic image.

Figure 63:
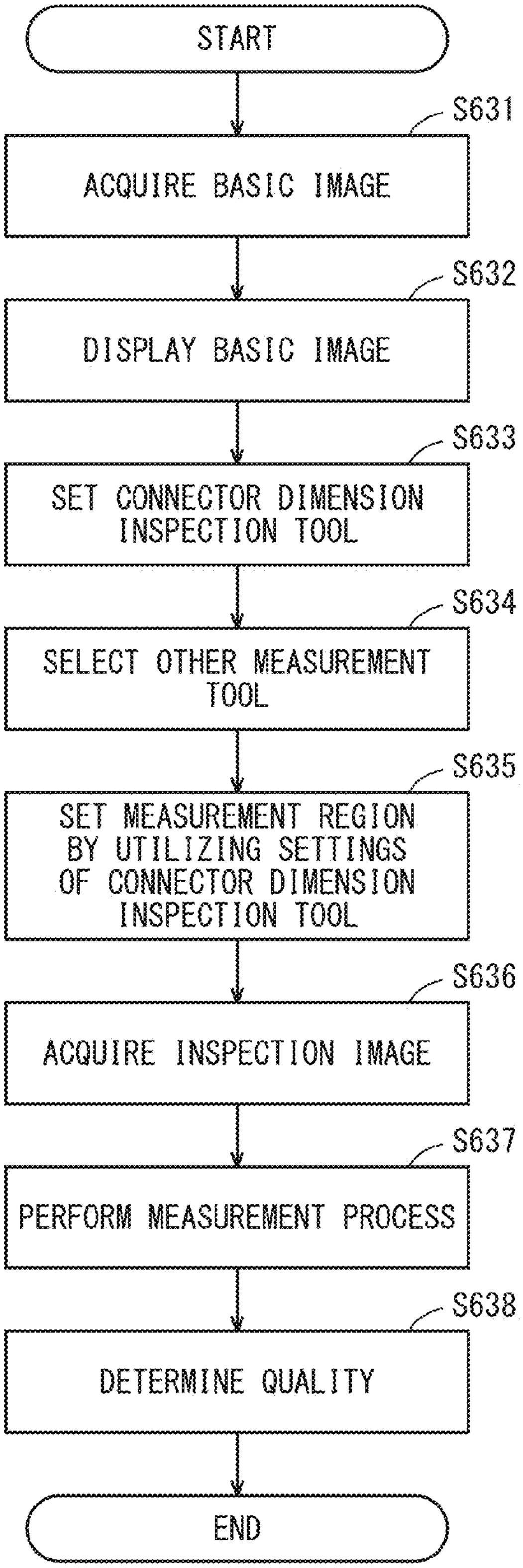
FIG. 63 is a flowchart illustrating an appearance inspection method according to this embodiment.

FIG. 63 is a flowchart illustrating an appearance inspection method according to this embodiment.

In S631, the imaging control section 301 controls the camera 4, acquires a basic image by imaging an inspection object (a non-defective inspection object 8) having a plurality of characteristic portions having substantially the same shape arranged according to a fixed rule, and stores the acquired basic image in the basic image storage section 337.

In S632, the first measurement target setting section 311 causes the monitor 10 to display the basic image through the display control section 28.

In S633, the first measurement target setting section 311 sets the reference point 120, the inspection region 113, and the search region 112 for detecting positions of a plurality of characteristic portions of the inspection object 8 for each characteristic portion included in the basic image displayed on the monitor 10. Data of the reference point 120, the inspection region 113, and the search region 112 is stored in the characteristic data storage section 306.

In S634, the measurement tool selection section 331 selects, from a plurality of measurement tools for performing different measurement, a measurement tool (e.g., area measurement tool) that measures the inspection object 8. The area measurement tool is only exemplary. The present invention is similarly applicable to any measurement tool in which a measurement region is settable by referring to the reference point 120 or the search region 112 for a connector dimension inspection tool. Data of the measurement region is stored in the characteristic data storage section 306.

In S635, the measurement region setting section 332 sets the measurement region 112' of the selected measurement tool based on the set reference point 120 or the set search region 112. This measurement region setting processing will be described in detail using FIG. 64.

In S636, the imaging control section 301 controls the camera 4 and acquires an inspection image by imaging the inspection object 8 conveyed on the line.

In S637, the dimension calculation section 302 performs measurement on the inspection image using the connector dimension inspection tool or the area measurement tool. Thereby, a pin height, a pin area, an area between pins, or the like described above are measured.

In S638, the quality determination section 303 determines quality of the inspection object 8 by comparing a measurement result output by the dimension calculation section 302 to a quality determination threshold value. For example, the quality determination section 303 determines that a certain pin is defective if the height of the pin exceeds the threshold value. If the pin area exceeds a burr detection threshold value, the quality determination section 303 determines that a metal burr has occurred in the pin (that is, the pin is defective). These threshold values are preset by the threshold value setting section 313. In addition, the quality determination section 303 determines that resin fog has occurred in the pin (that is, the pin is defective) if the measured area exceeds a resin fog detection threshold value. In addition, if an area of the resin at a position at which pin loss is set does not exceed a threshold value of a contamination detection amount, the quality determination section 303 determines that contamination has occurred or the pin has erroneously formed (that is, the portion is defective). This is because the area of the resin is less than a desired area if a foreign object is attached or if a pin is formed.

Figure 64:
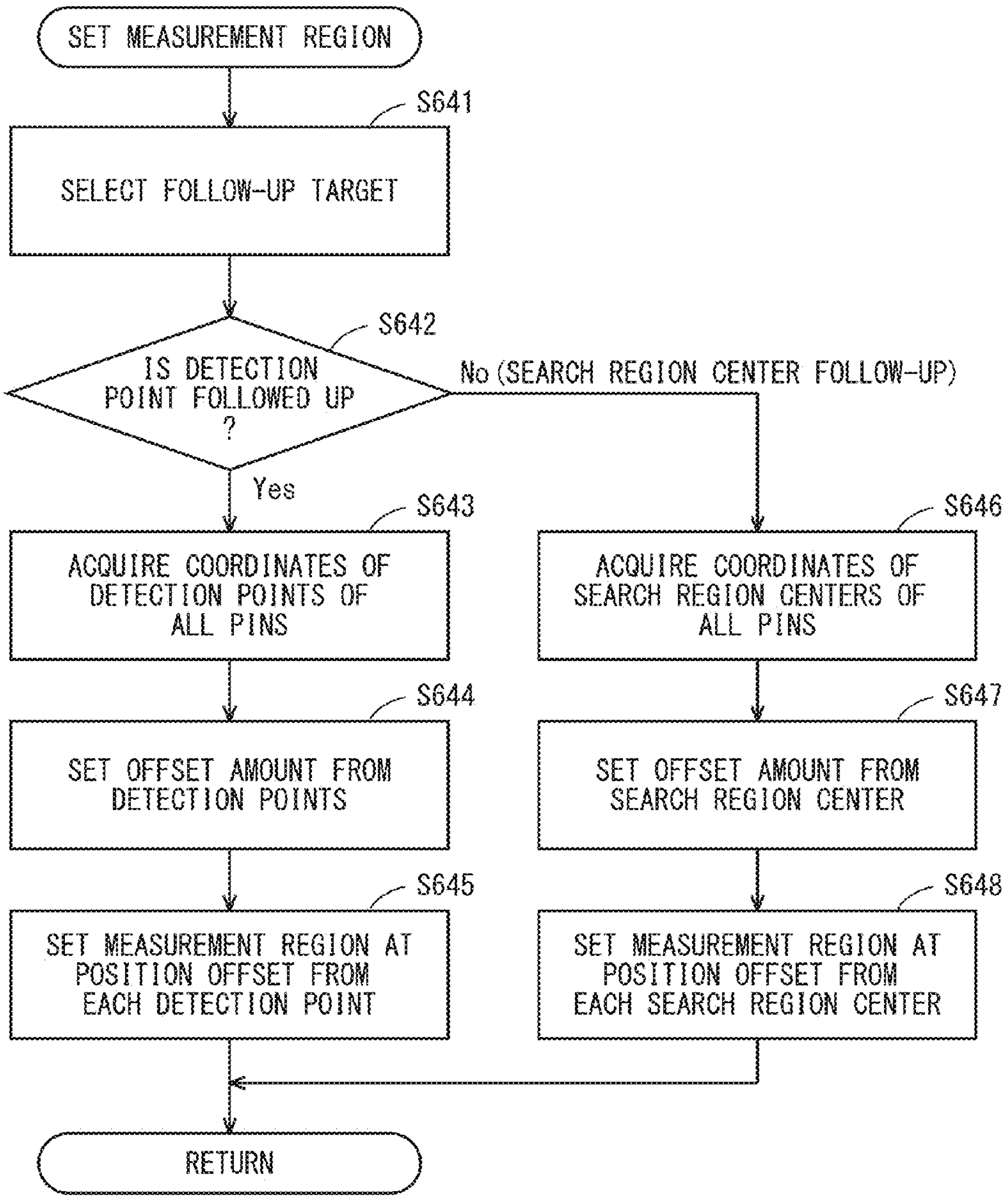
FIG. 64 is a flowchart illustrating a measurement region setting method.

FIG. 64 is a flowchart illustrating a measurement region setting method. The measurement region setting method corresponds to S635 illustrated in FIG. 63.

In S641, the follow-up target selection section 334 selects a target to be followed up by the measurement region 112' (e.g., the reference point 120 or the search region center 620) according to the operation of the mouse 9.

In S642, the measurement region setting section 332 determines whether detection point follow-up has been selected by the follow-up target selection section 334 (that is, an operation of following up the reference point 120). When the detection point follow-up has been selected, the process proceeds to S643. When the search region center follow-up has been selected, the process proceeds to S646.

Detection Point Follow-Up

In S643, the measurement region setting section 332 reads and acquires coordinate data of the reference point 120 of every pin stored in the characteristic data storage section 306. The measurement region setting section 332 temporarily sets the measurement region 112' based on the reference point 120 and causes the monitor 10 to display the temporarily set measurement region 112'. For example, in a default state, the center of the measurement region 112' is set to the reference point 120. In addition, the size of the measurement region 112' is also set to a predetermined given size. The user adjusts the size and position of one measurement region 112' displayed by operating the mouse 9.

In S644, the measurement region adjustment section 333 adjusts the position and the size of the measurement region 112' set based on the reference point 120 according to the operation of the mouse 9, and stores adjustment amounts of the position and the size at that time as offset amounts in the characteristic data storage section 306.

In S645, the measurement region adjustment section 333 sets the same offset amounts for the remaining measurement regions 112'. Thereby, each measurement region 112' is arranged at a position offset by the offset amount from each reference point 120. In addition, an adjustment result of the size is also reflected in each measurement region 112'. The layout result is displayed on the monitor 10 in real time.

Search Region Follow-Up

In S646, the measurement region setting section 332 reads and acquires coordinate data of search region centers 620 of search regions 112 of all pins stored in the characteristic data storage section 306. The measurement region setting section 332 temporarily sets the measurement region 112' based on the search region center 620, and causes the monitor 10 to display the measurement region 112'. For example, in a default state, the center of the measurement region 112' is set to the search region center 620. In addition, the size of the measurement region 112' is also set to a predetermined given size. The user adjusts the size and position of one measurement region 112' displayed by operating the mouse 9.

In S647, the measurement region adjustment section 333 adjusts the position and the size of the measurement region 112' set based on the search region center 620 according to the operation of the mouse 9, and stores adjustment amounts of the position and the size as offset amounts in the characteristic data storage section 306 at that time.

In S648, the measurement region adjustment section 333 sets the same offset amounts for the remaining measurement regions 112'. Thereby, each measurement region 112' is arranged at a position offset by the offset amount from each search region center 620. In addition, an adjustment result of the size is also reflected in each measurement region 112'. The layout result is displayed on the monitor 10 in real time.

As described above, according to this embodiment, the reference point 120 or the search region 112 serving as a reference for measurement for a first measurement tool such as a connector dimension inspection tool for a basic image acquired by imaging a non-defective product is set. Next, a second measurement tool such as an area measurement tool, which performs measurement separate from the first measurement tool, is selected by the user. For coordinate data of the measurement region 112' that is a region set for a basic image in which the second measurement tool measures a characteristic portion (e.g., a pin or the like) of the inspection object, coordinate data of the reference point 120 or the search region 112 set for the first measurement tool is adjusted if necessary and referred to. Thus, according to this embodiment, the burden on the user can be reduced by referring to a measurement region set for a certain measurement tool among a plurality of measurement tools to be used by the appearance inspection device 1 as a measurement region of another measurement tool. For example, because a region setting interval is not fixed in a connector provided with multi-row pins, the burden on the user is heavy in the related art. In the present invention, the measurement region for the appearance inspection is configured to be simply set because setting of dimension measurement or a measurement result is referred to.

For example, the reference point 120 is a detection point serving as a reference of the position detection of the characteristic portion, and the search region 112 is a region for searching for an image consistent with a model image of a characteristic portion clipped in a range of the inspection region 113 from the basic image through pattern recognition. The model image is vertically or horizontally shifted within the search region 112, and similarity is calculated. The measurement region setting section 332 sets the measurement region 112' to follow up the reference point 120 or the search region 112. When a plurality of characteristic portions have substantially the same shape and are arranged according to a fixed rule, the reference point 120 or the search region 112 is also arranged according to a fixed rule. That is, there is a correlation between coordinates of the reference point 120 or the search region 112 and coordinates of the measurement region 112'. Consequently, it is possible to accurately arrange the measurement region 112' if the measurement region 112' is set to follow up the reference point 120 or the search region 112.

When there is pin loss or pin bending in the inspection object 8 as described above, it is important which one of the reference point 120 and the search region 112 is to follow up the measurement region 112' for improving work efficiency. In this embodiment, the follow-up target selection section 334 selects the reference point 120 or the search region 112 as a follow-up target of the measurement region 112' according to the user's input. As described using FIG. 60, the user's workload can be reduced if the reference point 120 of the connector dimension inspection tool is selected as a follow-up target in order to accurately set the measurement region 112' for measuring an area of a pin when there is pin bending. On the other hand, as described using FIG. 61, the user's workload can be reduced if the search region 112 (particularly, the search region center 620) of the connector dimension inspection tool is selected as a follow-up target in order to accurately set the measurement region 112' for measuring an area of a pin when there is pin loss.

The size and position of the measurement region 112' may not be consistent with the size and position of the search region 112. That is, there is a case in which at least one of the position and size of the measurement region 112' set by the measurement region setting section 332 should be adjusted based on the position detection region for a connector dimension inspection tool set by the first measurement target setting section 311. Accordingly, the measurement region adjustment section 333 may adjust at least one of the position and size of the measurement region 112' set by the measurement region setting section 332 according to the operation of the pointer 650 using the mouse 9.

When it is necessary to finely adjust each of positions and sizes of the plurality of measurement regions 112', the user's workload for the fine adjustment on each of the plurality of measurement regions 112' through the operation of the mouse 9 is heavy. On the other hand, in this embodiment, it is assumed that the plurality of characteristic portions have substantially the same shape and are arranged according to a fixed rule. Consequently, when this regularity is used, it is possible to simply reflect an adjustment result in the remaining other measurement regions 112' by adjusting one measurement region 112'. Accordingly, in this embodiment, the measurement region adjustment section 333 may adjust each of the positions or sizes of the plurality of measurement regions 112' set by the measurement region setting section 332 by an equal adjustment amount in association with an operation amount of the mouse 9. Thereby, the user's workload can be significantly reduced.

According to this embodiment, a histogram indicating an image density of the measurement region 112' may be displayed. The user can easily determine whether the measurement region 112' is accurately set by checking the histogram in real time when the measurement region 112' is finely adjusted.

As described above, when there is pin loss, the pin position detection region of the pin is invalidated in the connector dimension inspection tool. However, it may be desired to check whether a foreign object is attached or whether a pin is erroneously formed at the pin loss position. In such a case, it is necessary to set the measurement region 112' also at the pin loss position. Consequently, the measurement region setting section 332 cancels the invalidation of a position detection region invalidated due to pin loss and sets the measurement region 112' based on the position detection region. Thereby, even when there is loss of a characteristic portion, the measurement region 112' can be set.

In addition, the UI control section 310 overlays and displays a mark indicating a position of a characteristic portion on a basic image. Thereby, the user easily recognizes a position of the characteristic portion visually.

Although an example in which the area measurement tool refers to a parameter of the connector dimension inspection tool has been described in this embodiment, the present invention is not necessarily limited thereto. Parameters are set based on characteristic portions in a plurality of measurement tools such as the edge position measurement tool, the edge angle measurement tool, the edge width measurement tool, the edge pitch measurement tool, the area measurement tool, the blob measurement tool, the pattern search measurement tool, the scratch measurement tool, the OCR recognition tool, the trend edge tool, the grayscale tool, and the density tool as described above. Consequently, a parameter of one measurement tool can be similarly referred to as a parameter of another measurement tool.

Although pattern search has been described as a pin position detection method in this embodiment, another method may be adopted. For example, a method of detecting a pin position using a geometric search, a method of detecting a pin position by applying edge detection, a method of detecting a pin position by applying blob detection, and the like may be used instead of the pattern search.

What is claimed is:

1. An appearance inspection device comprising:

a basic image storage section which stores a basic image obtained by imaging an inspection object having a plurality of characteristic portions arrayed in a specific direction;

a detection processing section which detects, from the basic image, each of positions of the plurality of characteristic portions of the inspection object;

a measurement tool selection section which selects, from a plurality of measurement tools for performing different measurement, a measurement tool to measure a measurement region of the inspection object;

a measurement region setting section which accepts position adjustment of the measurement region corresponding to at least one of the plurality of characteristic portions, the measurement region being for performing a measurement with use of the measurement tool selected by the measurement tool selection section, and sets the measurement region at a position shifted by the amount of the accepted position adjustment from each of positions of the plurality of characteristic portions detected by the detection processing section;

a display section which displays the measurement region set by the measurement region setting section along with the basic image; and a quality determination section which performs measurement according to the measurement region set by the measurement region setting section, and determines whether the inspection object is good or defective based on a measurement result.

2. The appearance inspection device according to claim 1, further comprising:

a measurement region adjustment section which adjusts at least one of a position and a size of the measurement region set by the measurement region setting section based on the position of the characteristic portion of the inspection object detected by the detection processing section, wherein, the measurement region setting section sets the measurement region at a position shifted by the amount adjusted by the measurement region adjustment section.

3. The appearance inspection device according to claim 1, further comprising:

a histogram creation section which creates a histogram indicating an image density of the measurement region set by the measurement region setting section, wherein the display section displays the histogram created by the histogram creation section.

4. The appearance inspection device according to claim 1, wherein the display section performs overlays and displays a mark indicating a position of the characteristic portion on the basic image.

5. The appearance inspection device according to claim 1, wherein the detection processing section detects each of positions of the plurality of characteristic portions of the inspection object using edge detection.

6. The appearance inspection device according to claim 1, further comprising:

a model image registration section which registers a model image of the characteristic portion, wherein the detection processing section detects each of positions of the plurality of characteristic portions of the inspection object using pattern matching with the model image.

7. The appearance inspection device according to claim 1, wherein the measurement region setting section accepts setting of the measurement region about at least one of a position and a size of the measurement region.

8. The appearance inspection device according to claim 1, further comprising:

a position detection region setting section which sets, along the specific direction, a plurality of search regions for limiting a target region to detect each of positions of the plurality of characteristic portions of the inspection object, wherein the detection processing section detects position of the characteristic portion of the inspection object within the search region set by the position detection region setting section.

9. The appearance inspection device according to claim 8, further comprising:

a selection section which selects any of a detection point associated with each of positions of the plurality of characteristic portions detected by the detection processing section and the search region set by the position detection region setting section, wherein the measurement region setting section sets the measurement region based on the detection point when the detection point is selected by the selection section, and sets the measurement region based on the search region when the search region is selected by the selection section.

10. The appearance inspection device according to claim 8, wherein when the position detection region setting section invalidates one or more search regions among a plurality of search regions, the measurement region setting section cancels the invalidation of the one or more search regions, and sets the measurement region based on the one or more search regions in which the invalidation has been cancelled.

11. The appearance inspection device according to claim 1, wherein the measurement region setting section accepts setting of the measurement region based on one of the plurality of characteristic portions detected by the detection processing section.

12. The appearance inspection device according to claim 11, wherein the measurement region adjustment section adjusts at least one of a position, a size, and an angle of each of a plurality of measurement regions set by the measurement region setting section by an equal adjustment amount.

13. An appearance inspection method comprising the steps of:

acquiring a basic image obtained by imaging an inspection object having a plurality of characteristic portions arrayed in a specific direction;

detecting, from the basic image, each of positions of the plurality of characteristic portions of the inspection object;

selecting, from a plurality of measurement tools for performing different measurement, a measurement tool that measures a measurement region of the inspection object;

accepting position adjustment of the measurement region corresponding to at least one of the plurality of characteristic portions, the measurement region being for performing a measurement with use of the selected measurement tool;

setting the measurement region at a position shifted by the amount of the accepted position adjustment from each of detected positions of the plurality of characteristic portions;

displaying the set measurement region along with the basic image on a display section;

acquiring an inspection image by imaging the inspection object; and performing measurement for the inspection image according to the set measurement region and determining quality of the inspection object based on a measurement result.

14. A non-transitory computer readable medium that stores a program which when executed by a computer performs the steps of the appearance inspection method according to claim 13.

* * * * *